United States Patent
van der Burg et al.

(10) Patent No.: US 10,426,589 B2
(45) Date of Patent: *Oct. 1, 2019

(54) SYSTEM AND METHOD FOR DELIVERING A LEFT ATRIAL APPENDAGE CONTAINMENT DEVICE

(71) Applicant: ATRITECH, INC., Plymouth, MN (US)

(72) Inventors: Erik J. van der Burg, Los Gatos, CA (US); Stewart M. Kume, Belmont, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 518 days.

This patent is subject to a terminal disclaimer.

(21) Appl. No.: 13/725,362

(22) Filed: Dec. 21, 2012

(65) Prior Publication Data

US 2013/0110154 A1 May 2, 2013

Related U.S. Application Data

(63) Continuation of application No. 11/003,696, filed on Dec. 3, 2004, now abandoned.

(Continued)

(51) Int. Cl.
*A61F 2/01* (2006.01)
*A61B 17/00* (2006.01)
(Continued)

(52) U.S. Cl.
CPC ............ *A61F 2/01* (2013.01); *A61B 17/0057* (2013.01); *A61B 17/12022* (2013.01);
(Continued)

(58) Field of Classification Search
CPC ............... A61F 2/01; A61F 2230/0076; A61F 2002/016; A61F 2002/30092;
(Continued)

(56) References Cited

U.S. PATENT DOCUMENTS 5,306,234 A 4/1994 Johnson
5,370,650 A 12/1994 Tovey et al.
(Continued)

FOREIGN PATENT DOCUMENTS

| EP | 03032818 A2 | 4/2003 |
|---|---|---|
| WO | 9640356 A1 | 12/1996 |
| WO | 0217809 A1 | 3/2002 |

OTHER PUBLICATIONS

Blackshear, Joseph L. et al., "Appendage Obliteration to Reduce Stroke in Cardiac Surgical Patients with Atrial Fibrillation," Ann Thorac Sug 1996, vol. 61, pp. 755-759.
(Continued)

*Primary Examiner* — Wade Miles
*Assistant Examiner* — Michael G Mendoza
(74) *Attorney, Agent, or Firm* — Seager, Tufte & Wickhem LLP

(57) ABSTRACT

A method of delivering and deploying the device for containing the emboli during a surgical procedure proximate to the heart. Access is gained to the heart and the left atrium such that a distal end of the delivery sheath can be located near the left atrial appendage. A distal end of a delivery catheter can be loaded with the device in a collapsed position and passed through the delivery sheath thereby delivering the device within the left atrial appendage. The device is expanded to contain emboli in the left atrium appendage.

16 Claims, 43 Drawing Sheets

Related U.S. Application Data

(60) Provisional application No. 60/526,960, filed on Dec. 4, 2003.

(51) Int. Cl.

| | | |
|---|---|---|
| *A61B 17/12* | (2006.01) | |
| *A61F 2/966* | (2013.01) | |
| *A61F 2/95* | (2013.01) | |
| *A61F 2/24* | (2006.01) | |

(52) U.S. Cl.
CPC .. *A61B 17/12122* (2013.01); *A61B 17/12172* (2013.01); *A61F 2/013* (2013.01); *A61B 2017/003* (2013.01); *A61B 2017/00575* (2013.01); *A61B 2017/00579* (2013.01); *A61B 2017/00592* (2013.01); *A61B 2017/00597* (2013.01); *A61B 2017/00615* (2013.01); *A61B 2017/00623* (2013.01); *A61B 2017/00632* (2013.01); *A61B 2017/12054* (2013.01); *A61B 2017/12095* (2013.01); *A61F 2/243* (2013.01); *A61F 2/2439* (2013.01); *A61F 2002/018* (2013.01); *A61F 2002/9505* (2013.01); *A61F 2002/9511* (2013.01); *A61F 2002/9665* (2013.01); *A61F 2230/0006* (2013.01); *A61F 2230/008* (2013.01); *A61F 2230/0071* (2013.01)

(58) Field of Classification Search
CPC ........ A61F 2210/0014; A61F 2002/011; A61F 2220/0016
See application file for complete search history.

(56) References Cited

U.S. PATENT DOCUMENTS

| | | | |
|---|---|---|---|
| 5,599,329 A | 2/1997 | Gabbay | |
| 5,865,791 A | 2/1999 | Whayne et al. | |
| 6,152,144 A | 11/2000 | Lesh et al. | |
| 6,231,561 B1 | 5/2001 | Frazier et al. | |
| 6,290,674 B1 | 9/2001 | Roue et al. | |
| 6,328,727 B1 | 12/2001 | Frazier et al. | |
| 6,379,366 B1 | 4/2002 | Fleischman et al. | |
| 6,419,669 B1 | 7/2002 | Frazier et al. | |
| 6,488,689 B1 | 12/2002 | Kaplan et al. | |
| 6,551,303 B1 | 4/2003 | VanTassel et al. | |
| 6,561,969 B2 | 5/2003 | Frazier et al. | |
| 6,641,557 B1 | 11/2003 | Frazier et al. | |
| 6,650,923 B1 | 11/2003 | Lesh et al. | |
| 6,652,555 B1 | 11/2003 | VanTassel et al. | |
| 6,652,556 B1 | 11/2003 | VanTassel et al. | |
| 6,666,861 B1 | 12/2003 | Grabek | |
| 6,689,150 B1 | 2/2004 | VanTassel et al. | |
| 6,730,108 B2 | 5/2004 | VanTassel et al. | |
| 6,830,576 B2 | 12/2004 | Fleischman et al. | |
| 7,044,134 B2 | 5/2006 | Khairkahan et al. | |
| 7,226,458 B2 | 6/2007 | Kaplan et al. | |
| 7,344,543 B2 | 3/2008 | Sra | |
| 7,735,493 B2 | 6/2010 | Van der Burg et al. | |
| 2002/0049457 A1 | 4/2002 | Kaplan | |
| 2002/0111636 A1 | 8/2002 | Fleischman et al. | |
| 2002/0111647 A1 | 8/2002 | Khairkahan et al. | |
| 2002/0151970 A1 | 10/2002 | Garrison et al. | |
| 2005/0033287 A1 | 2/2005 | Sra | |
| 2005/0038470 A1 | 2/2005 | Van der Burg et al. | |
| 2005/0273135 A1* | 12/2005 | Chanduszko ...... | A61B 17/0057 606/213 |

OTHER PUBLICATIONS

Lindsay, Bruce D.. "Obliteration of the Left Atrial Appendage: A Concept Worth Testing," Ann Thorac Surg, 1996, vol. 61, p. 515.

Ostermayer, Stefan et al., "Percutaneous Closure of the Left Atrial Appendage," Journal of Interventional Cardiology, 2003, vol. 16, No. 6, pp. 553-556.

* cited by examiner

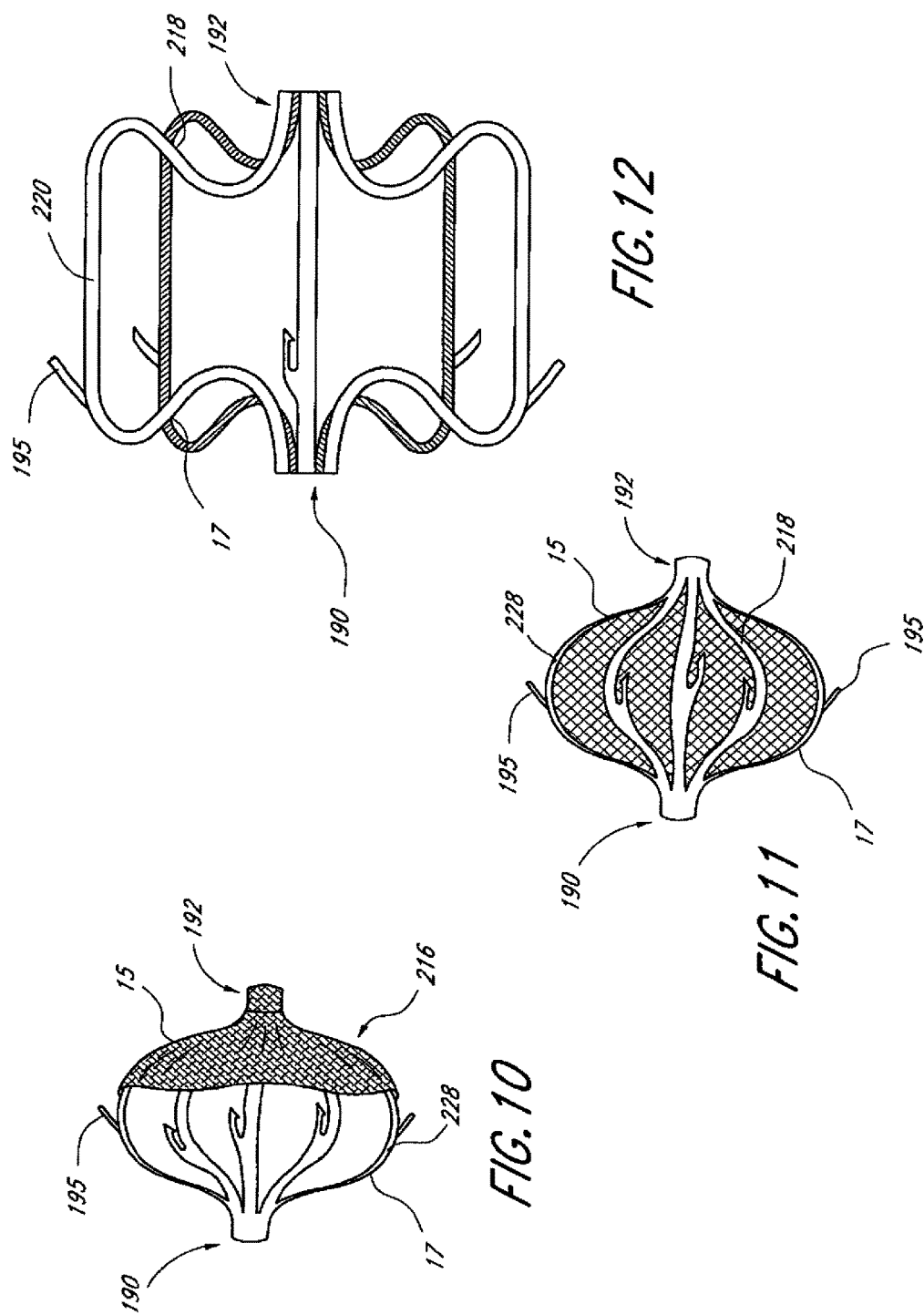

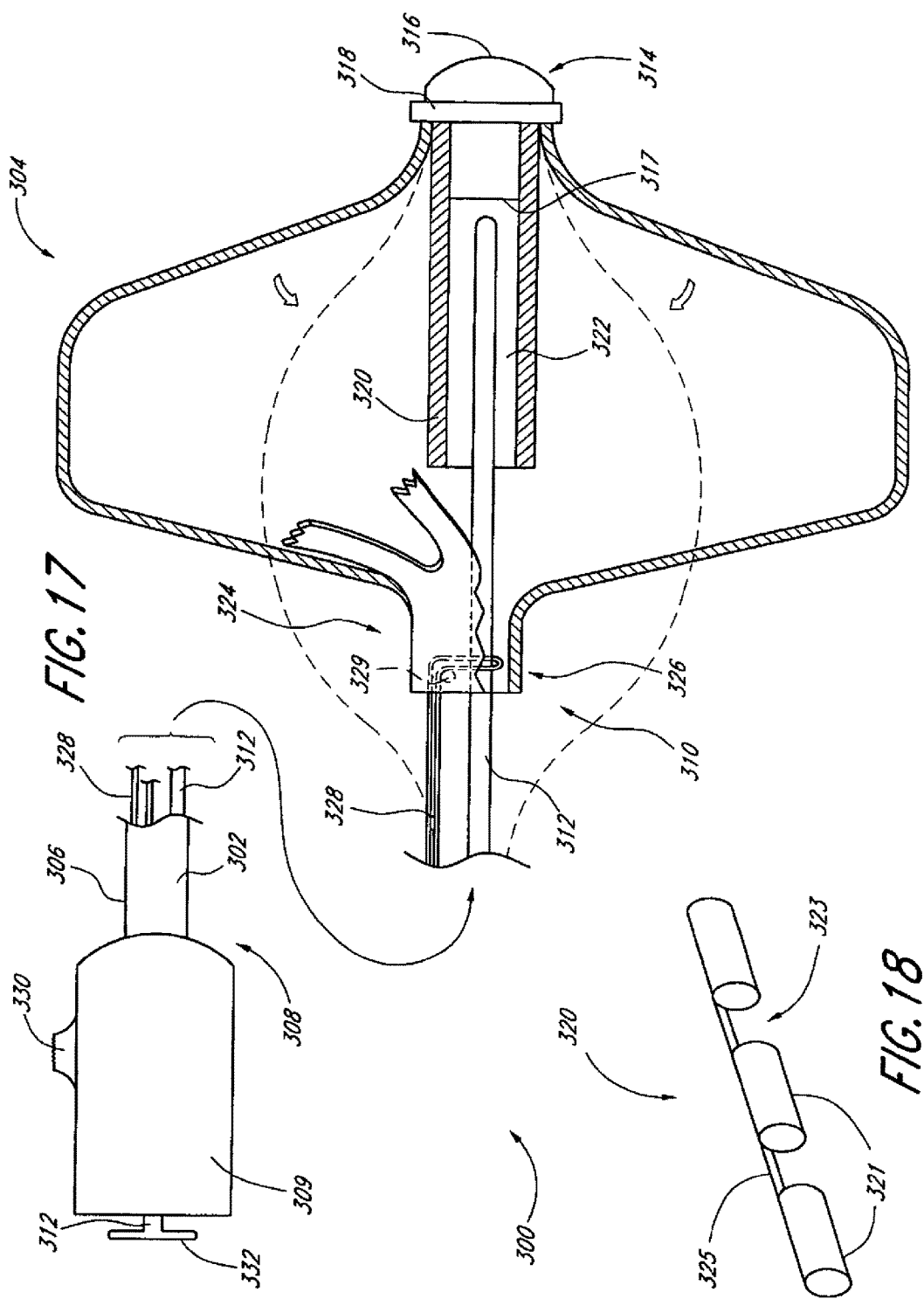

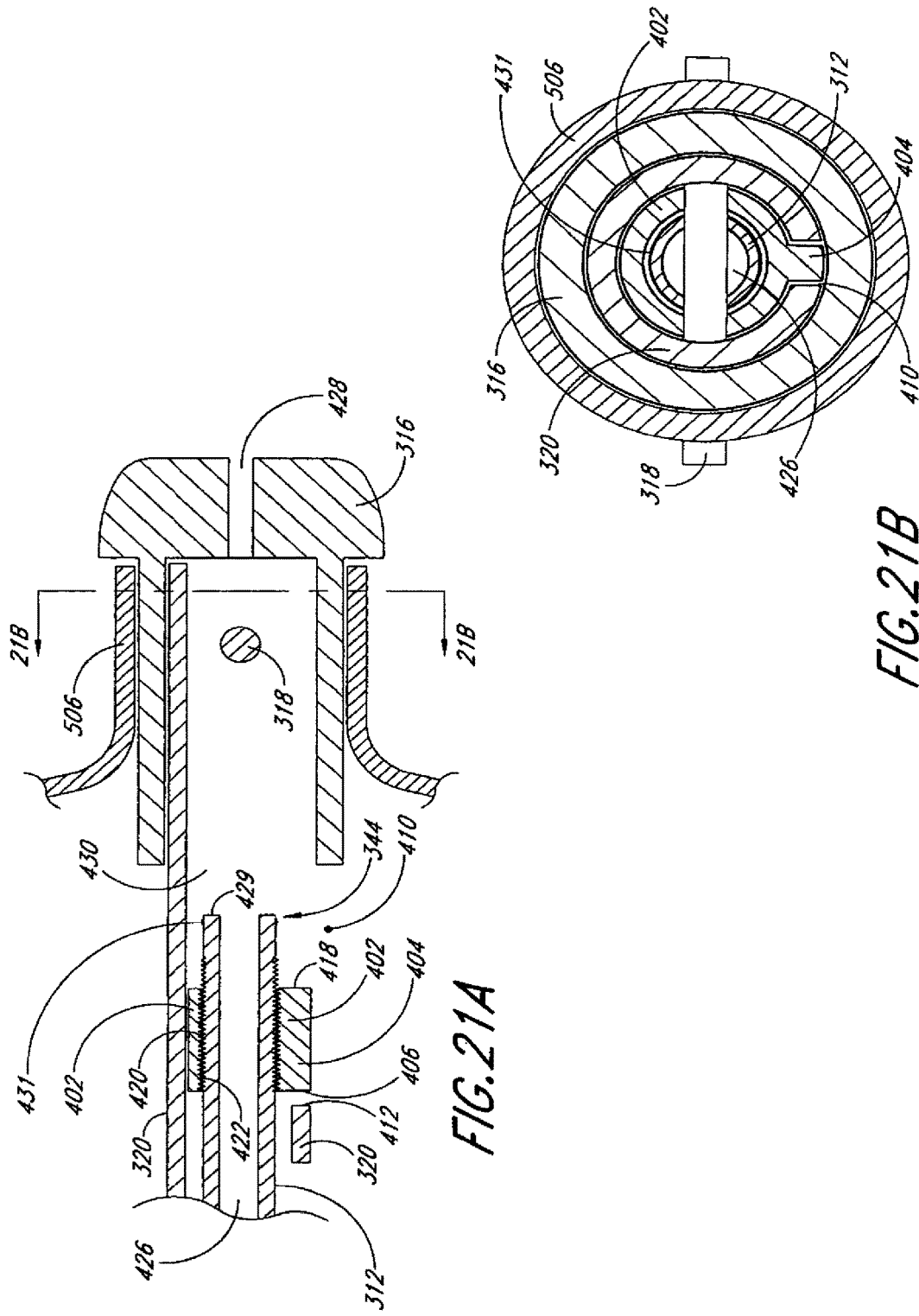

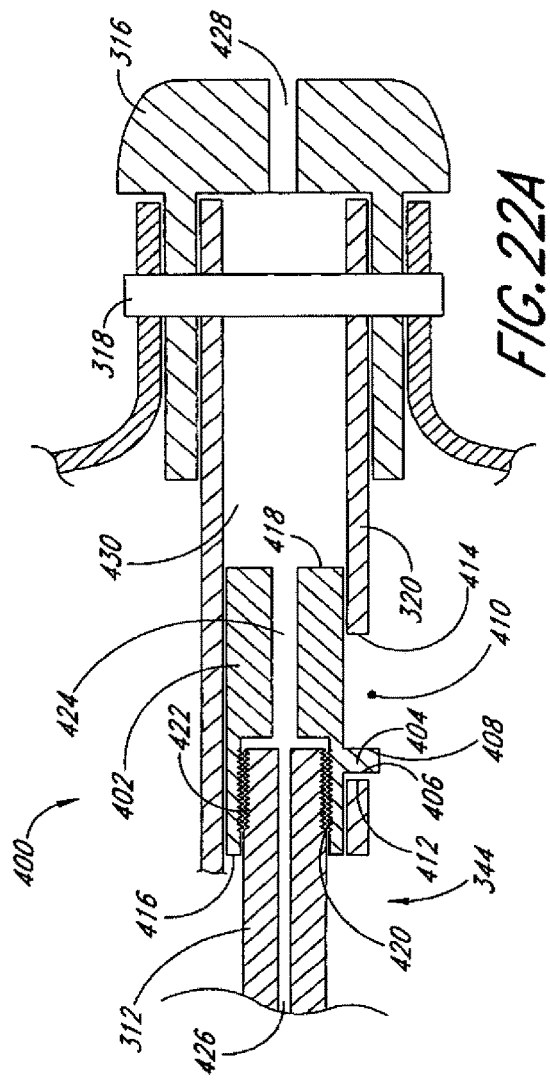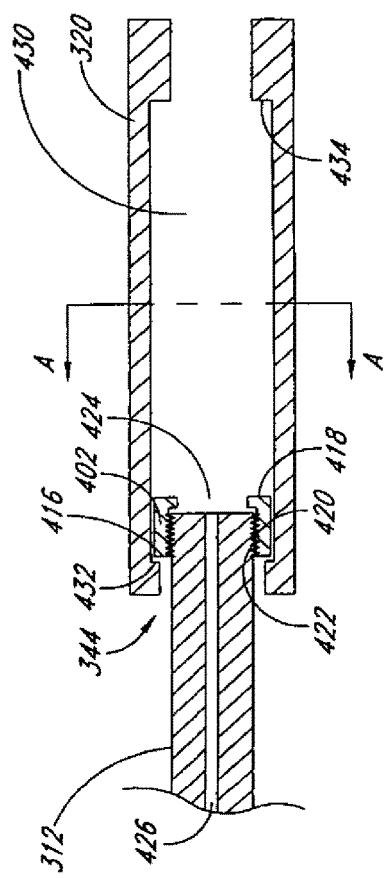

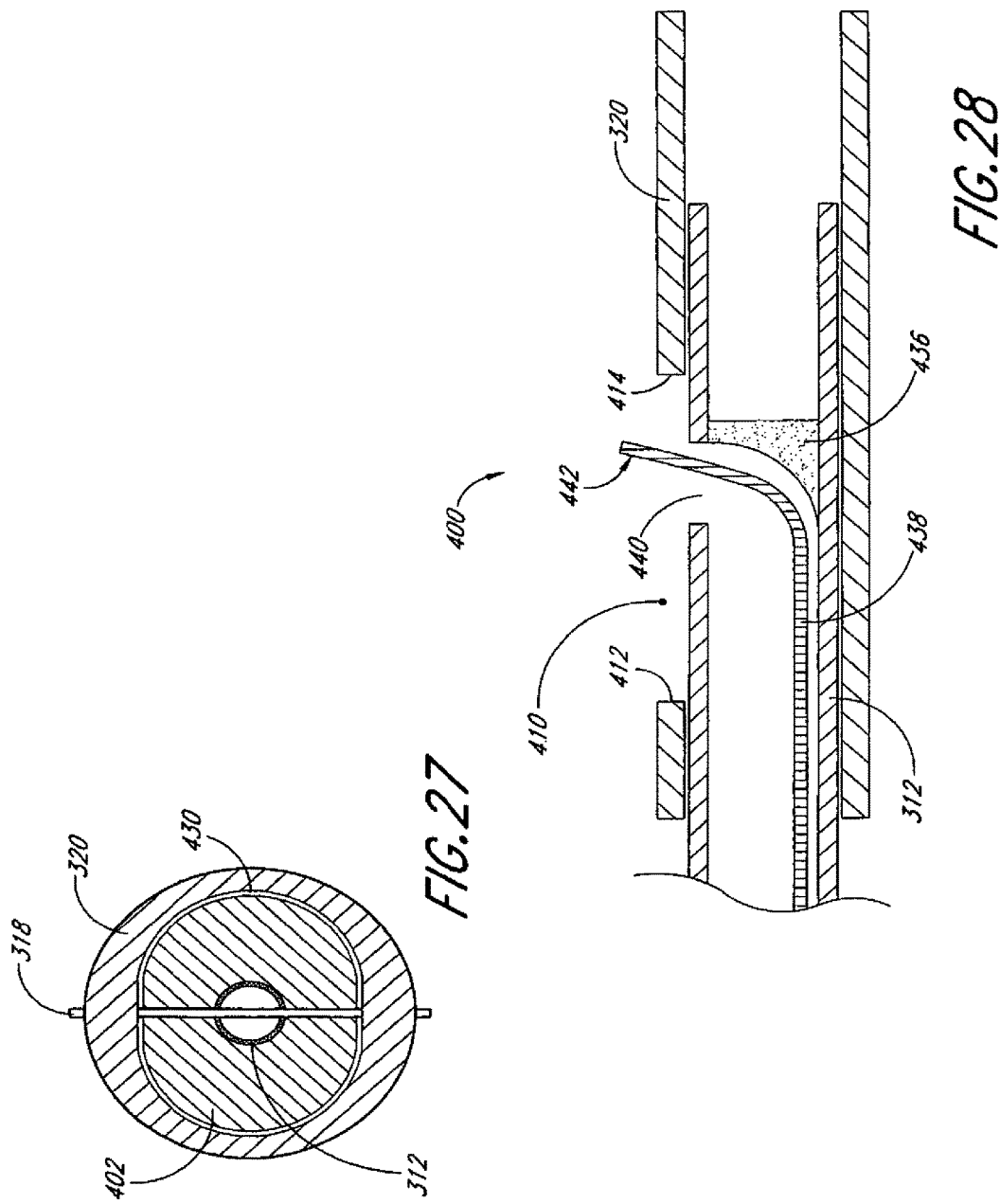

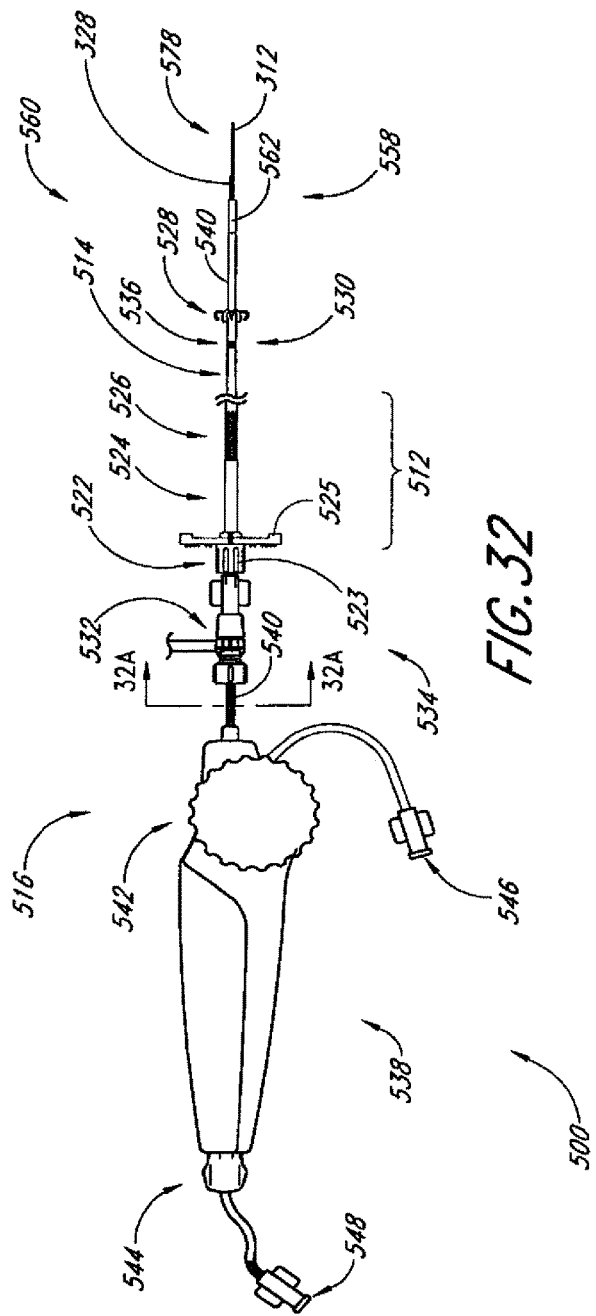
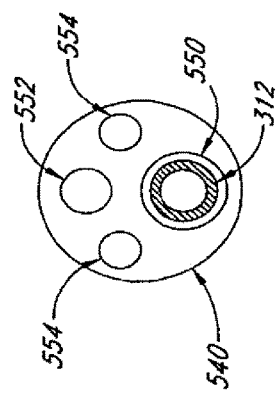
FIG. 32
FIG. 32A

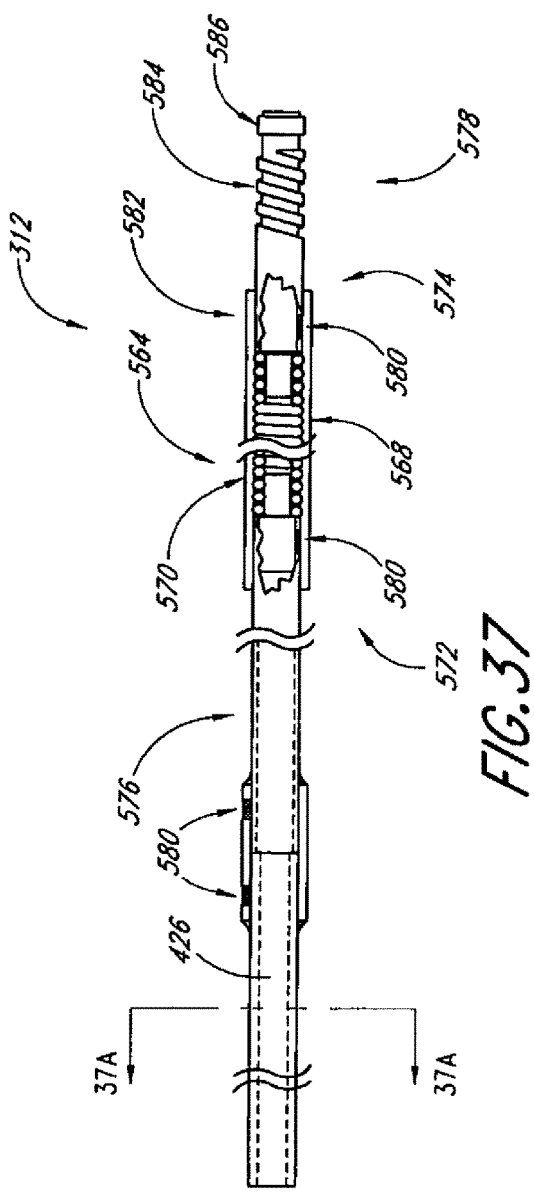
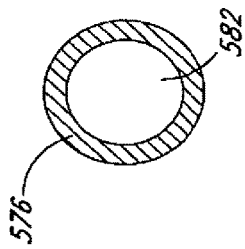
FIG. 37
FIG. 37A

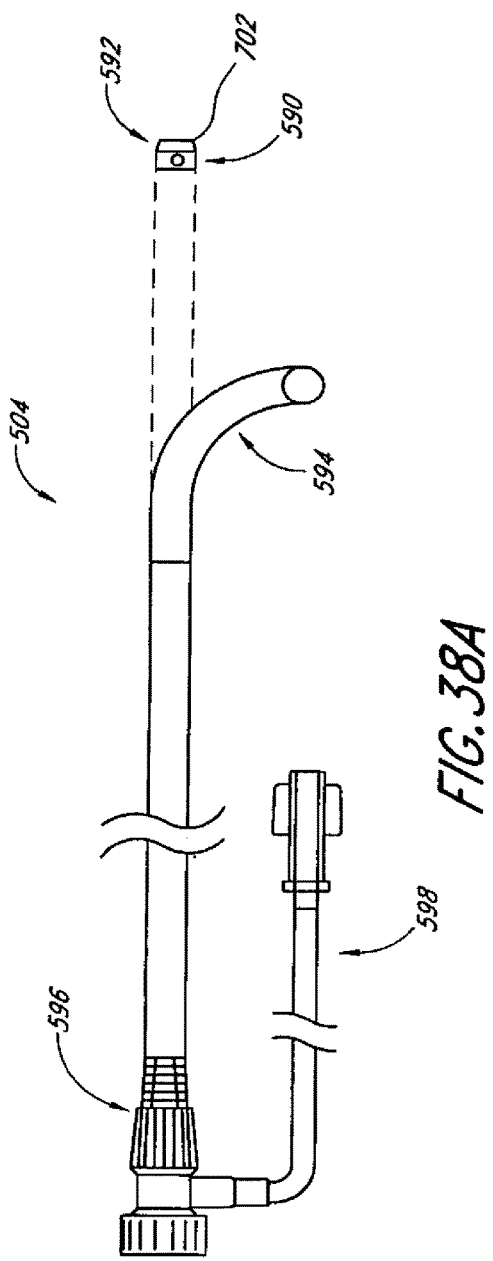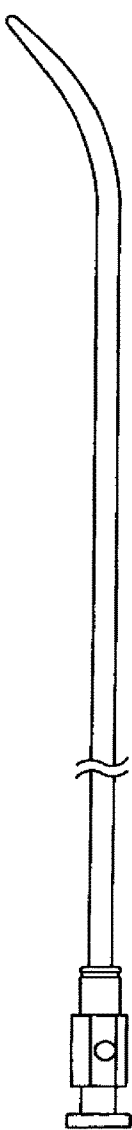
FIG. 38A
FIG. 38B
FIG. 38C

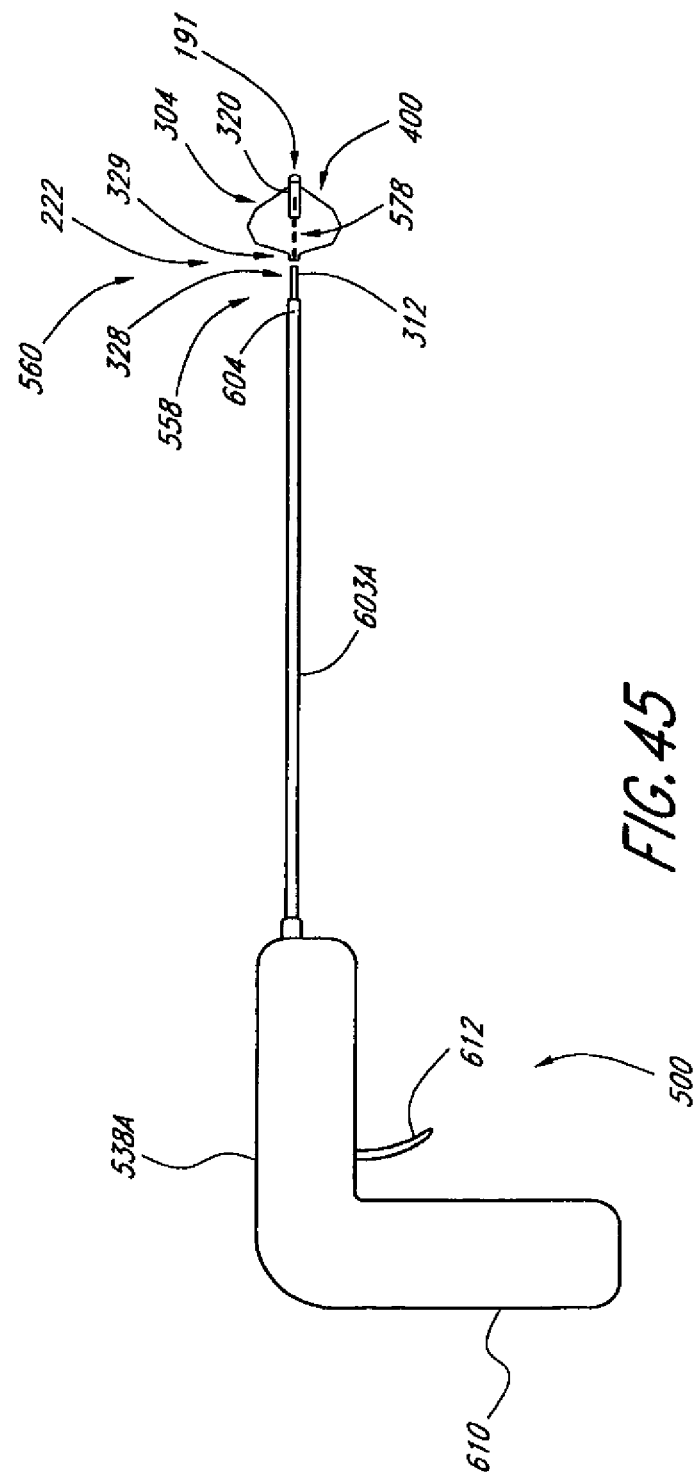

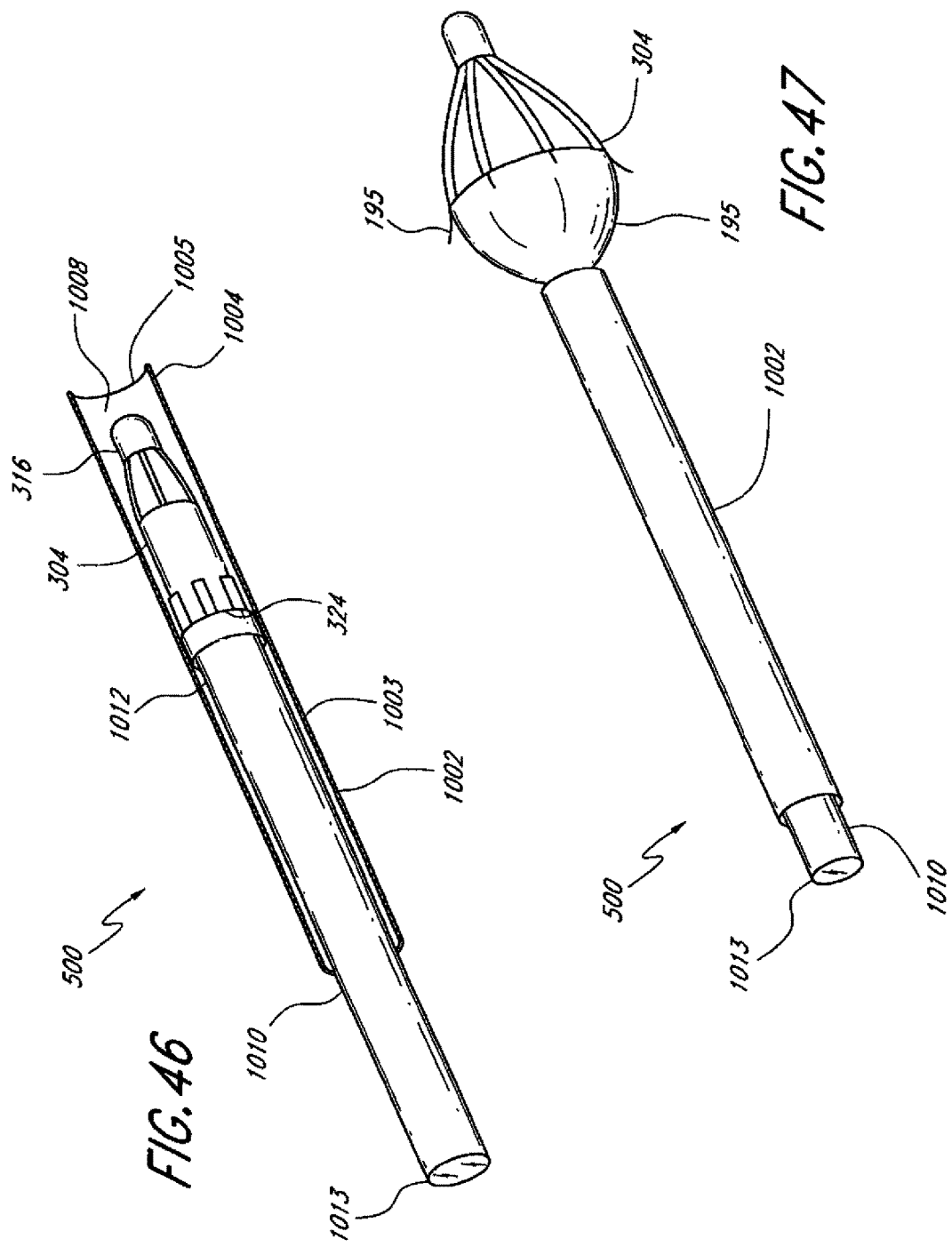

SYSTEM AND METHOD FOR DELIVERING A LEFT ATRIAL APPENDAGE CONTAINMENT DEVICE

RELATED APPLICATIONS

This application is a continuation of U.S. application Ser. No. 11/003,696, filed Dec. 3, 2004, now abandoned, which claims the priority benefit under 35 U.S.C. .sctn. 119(e) of the provisional application 60/526,960, filed Dec. 4, 2003, each of which is hereby incorporated by reference in its entirety.

BACKGROUND OF THE INVENTION

1. Field of the Invention

Embodiments of this invention relate in general to a system and method for delivering a left atrial appendage containment device.

2. Description of the Related Art

Embolic stroke is the nation's third leading killer for adults, and is a major cause of disability. There are over 700,000 strokes per year in the United States alone. Of these, roughly 100,000 are hemorrhagic, and 600,000 are ischemic (either due to vessel narrowing or to embolism). The most common cause of embolic stroke emanating from the heart is thrombus formation due to atrial fibrillation. Approximately 80,000 strokes per year are attributable to atrial fibrillation. Atrial fibrillation is an arrhythmia of the heart that results in a rapid and chaotic heartbeat that produces lower cardiac output and irregular and turbulent blood flow in the vascular system. There are over five million people worldwide with atrial fibrillation, with about four hundred thousand new cases reported each year. Atrial fibrillation is associated with a 500 percent greater risk of stroke due to the condition. A patient with atrial fibrillation typically has a significantly decreased quality of life due, in part, to the fear of a stroke, and the pharmaceutical regimen necessary to reduce that risk.

For patients who develop atrial thrombus from atrial fibrillation, the clot normally occurs in the left atrial appendage (LAA) of the heart. The LAA is a cavity which looks like a small finger or windsock and which is connected to the lateral wall of the left atrium between the mitral valve and the root of the left pulmonary vein. The LAA normally contracts with the rest of the left atrium during a normal heart cycle, thus keeping blood from becoming stagnant therein, but often fails to contract with any vigor in patients experiencing atrial fibrillation due to the discoordinate electrical signals associated with AF. As a result, thrombus formation is predisposed to form in the stagnant blood within the LAA.

Blackshear and Odell have reported that of the 1288 patients with non-rheumatic atrial fibrillation involved in their study, 221 (17%) had thrombus detected in the left atrium of the heart. Blackshear J L, Odell J A., Appendage Obliteration to Reduce Stroke in Cardiac Surgical Patients With Atrial Fibrillation. Ann Thorac. Surg., 1996.61(2):755-9. Of the patients with atrial thrombus, 201 (91%) had the atrial thrombus located within the left atrial appendage. The foregoing suggests that the elimination or containment of thrombus formed within the LAA of patients with atrial fibrillation would significantly reduce the incidence of stroke in those patients.

Pharmacological therapies for stroke prevention such as oral or systemic administration of warfarin or the like have been inadequate due to serious side effects of the medications and lack of patient compliance in taking the medication. Invasive surgical or thorascopic techniques have been used to obliterate the LAA, however, many patients are not suitable candidates for such surgical procedures due to a compromised condition or having previously undergone cardiac surgery. In addition, the perceived risks of even a thorascopic surgical procedure often outweigh the potential benefits. See Blackshear and Odell, above. See also Lindsay B D., Obliteration of the Left Atrial Appendage: A Concept Worth Testing, Ann Thorac. Surg., 1996.61(2):515.

During surgical procedures, such as mitral valve repair, thrombus in the left atrial appendage may leave the LAA and enter the blood stream of a patient. The thrombus in the blood stream of the patient can cause embolic stroke. There are known techniques for closing off the LAA so that thrombus cannot enter the patient's blood stream. For example, surgeons have used staples or sutures to close the orifice of the LAA, such that the closed off LAA surrounds the thrombus. Unfortunately, using staples or sutures to close off the LAA may not completely close the orifice of the LAA. Thus, thrombus may leave the LAA and enter the patient's blood stream, even though the LAA is closed with staples or sutures. Additionally, closing the orifice of the LAA by using staples or sutures may result in discontinuities, such as folds or creases, in the endocardial surface facing the left atrium. Unfortunately, blood clots may form in these discontinuities and can enter the patient's blood stream, thereby causing health problems. Moreover, it is difficult to place sutures at the orifice of the LAA and may result in a residual appendage. For example, an epicardial approach to ligate sutures can result in a residual appendage. Similarly, thrombus may form in the residual appendage and enter the patient's blood stream causing health problems.

Despite the various efforts in the prior art, there remains a need for a minimally invasive method and associated devices for reducing the risk of health problems (e.g., embolic stroke) related to thrombus located in the left atrial appendage.

SUMMARY OF THE INVENTION

There is provided in accordance with one embodiment of the present invention a method for containing emboli within a left atrial appendage of a patient. In one embodiment, an implant that has a frame that is expandable from a reduced cross section to an enlarged cross section is provided, the frame extending between a proximal hub and a distal hub. The frame is releasably coupled near its proximal hub to a control line extending proximally away from the proximal hub. A slider assembly is provided that is connected to the frame, the slider assembly comprising a guide tube extending proximally from the distal hub and an inner member slideably received within the guide tube, the inner member being releasably coupled to an elongate core that extends proximally through the proximal hub, wherein movement of the inner member relative to the frame is at least partially limited by interference between a portion of the inner member and a portion of the guide tube.

In one embodiment, a method provides a left atrium access path to the left atrial appendage for delivery of a device, such as the implant discussed above. However, it will be appreciated that any suitable device may be used. A delivery sheath having a distal end can be distally advanced along the left atrium access path. The distal end of the delivery sheath is distally advanced until the delivery sheath is located proximate to an orifice of the left atrial appendage. The method provides a delivery catheter having a distal end that is coupled to the implant. The distal end of the delivery catheter that is coupled the implant is distally advanced through the delivery sheath along the left atrium access path and the implant is delivered to the left atrial appendage of the patient. The frame of the implant is expanded within the left atrial appendage by providing relative movement between the control line and the elongated core, wherein the elongated core is moveable relative to the implant while coupled to the inner member when the frame is positioned within the left atrial appendage.

In one embodiment, the delivery sheath is moved along the left atrium access path, which is located within a pulmonary vein, until the distal end of the delivery sheath is located near the LAA of the heart.

In another embodiment, the delivery sheath is moved along the left atrium access path, which is located through a hole in a wall of the left atrium, until the distal end of the delivery sheath is located near the LAA of the heart.

In another embodiment, a transseptal hole is provided and the delivery sheath is moved along the left atrium path, which is located within the right atrium and through the transseptal hole, until the distal end of the delivery sheath is located near the LAA of the heart.

In another embodiment, the left atrium is accessed by a surgical heart procedure. The delivery sheath is moved along the left atrium access path, which is located through the opening in the heart, until the distal end of the delivery sheath is located near the LAA of the heart.

In another embodiment, the left atrium is accessed by surgical heart procedure. The implant can be distally advanced along the left atrium access path, and the implant can be manually delivered to the left atrial appendage of the patient.

Further, in one preferred embodiment, a user is provided with a location of the distal end of the distally advanced delivery sheath within the left atrium of the patient by using direct visualization in the form of examination of the exterior surface of the heart, visualization through the use of echocardiography, visualization through optics including through thoracoscopes, or the use of X-ray fluoroscopy.

In another embodiment, a method of delivering a containment device to a left atrial appendage of a patient is provided. The method includes providing a left atrium access path and a delivery sheath is located along the left atrium access path. The delivery sheath has both a delivery path and a distal end. The delivery path extends along and within the delivery sheath. The delivery sheath is moved to place the distal end of the delivery sheath within the LAA of a heart. An implant is passed within the delivery sheath in a distal direction to the distal end of the delivery sheath. The implant is deployed by expanding a frame that is expandable from a reduced cross section to an enlarged cross section. In one embodiment, the implant contacts a surface of the LAA of the heart and forms a seal between the implant and the surface of the LAA.

It will be appreciated that any suitable device or instrument may be delivered to the LAA along the left atrium access path. In one embodiment, a device is delivered to the LAA as an adjunct to a surgical heart procedure (e.g., during mitral valve repair).

In some embodiments, a method is provide for delivering a device to a left atrial appendage. The method comprises forming an opening in a chest of a patient suitable for surgical heart procedures. An implantable device is advanced through the opening and into a left atrium. The implantable device is passed through the left atrium and is positioned at the left atrial appendage.

In some embodiments, a method is provided for delivering a device to a left atrial appendage. The method comprises forming an aperture in the outer wall of a left atrium of a heart. A delivery sheath is advanced through the aperture and into the left atrium. A distal end of the delivery sheath is positioned proximate to an orifice of the left atrial appendage while the delivery sheath extends through the left atrium and the aperture. A device is advanced through the delivery sheath and out of the distal end. The device is implanted at the left atrial appendage.

In some embodiments, a method is provided for delivering a device to a left atrial appendage. The method comprises providing a delivery sheath having a lumen and a distal end and a transition catheter having a tip configured to reduce injury to a patient. The delivery sheath and transition catheter are advanced along the right atrium and through a transseptal hole and into the left atrium until a distal end of the delivery sheath is proximate to an orifice of a left atrial appendage. The transition catheter is removed from the delivery sheath. The device is distally advanced a through the delivery sheath. The device is implanted at the left atrial appendage while the distal end of the delivery sheath is disposed within the left atrial appendage.

In some embodiments, a method is provided for delivering a device to a left atrial appendage. The method comprises providing a left atrium access path through a pulmonary vein to a left atrial appendage. A delivery sheath is advanced along the left atrium access path until the delivery sheath is located proximate to the left atrial appendage. An implant is advanced through the delivery sheath until the implant passes out of a distal end of the delivery sheath. The device is implanted at the left atrial appendage.

In some embodiments, a system for delivering a device to the left atrial appendage comprises an implant sized and configured to prevent passage of embolic material from a left atrial appendage. A delivery sheath defines a lumen and a distal end. A transition catheter has an atraumatic tip and is configured to slide through the lumen of the delivery sheath. The transition catheter is adapted to extend from the distal end of the delivery sheath when the distal end is proximate to the left atrial appendage. A delivery catheter is removably coupled to the implant. The delivery catheter and implant are configured to pass through the lumen of the delivery sheath to the left atrial appendage.

In some embodiments, a system for delivering a device to the left atrial appendage comprises an implant sized and configured to prevent passage of embolic material from a left atrial appendage. A delivery device is configured to carry the implant to the left atrial appendage. The delivery device has a length configured to access the left atrial appendage through an opening in a chest of a patient. The delivery device has a length of about 80 cm or less.

In some embodiments, a system for delivering a device into the left atrial appendage comprises an implant sized and configured to prevent passage of embolic material from a left atrial appendage. A delivery device is configured to carry the implant to the left atrial appendage. The delivery device has a length configured to access the left atrial appendage through an opening in a chest of a patient. The system further comprises means for providing surgical access to the left atrial appendage through the chest of the patient.

In some embodiments, a system for delivering a device into the left atrial appendage of a patient comprises an implant sized and configured to prevent passage of embolic material from a left atrial appendage. A delivery device is configured to carry the implant to the left atrial appendage. The delivery device has a length configured to access the left atrial appendage through an opening in a chest of a patient. The system further comprises a means for performing a surgical heart procedure in the heart of the patient.

In some embodiments, a system for delivering a device to the left atrial appendage comprises an implant sized and configured to prevent passage of embolic material from a left atrial appendage. A delivery device is configured to carry the implant to the left atrial appendage. The delivery device is sized and configured to access the left atrial appendage through a pulmonary vein. The delivery device has a length of about 50 cm or less.

In some, embodiments, a kit can be provided suitable for delivering a device to the left atrial appendage. For example, the kit can comprise the devices, apparatuses, and/or systems described herein. The kit may optionally comprise packaging configured to receive a system configured to deliver a device to the left atrial appendage and/or instructions.

BRIEF DESCRIPTION OF THE DRAWINGS

FIGS. 10 and 11 are side elevational schematic representations of partial and complete barrier layers on the containment device of FIG. 7;

FIG. 12 is a side elevational schematic view of an alternate containment device in accordance with another embodiment of the present invention;

FIG. 17 is a schematic view of a deployment system in accordance with one embodiment of the present invention;

FIG. 18 is a perspective view of a flexible guide tube for use in the configurations of FIG. 17 and/or FIG. 19;

FIG. 21A is a schematic cross sectional view of a slider assembly for use with the adjustable implant deployment system of FIG. 21;

FIG. 21B is a cross sectional view of the slider assembly of FIG. 21A taken along cut line 21B-21B;

FIG. 22A is a schematic cross sectional view of a slider assembly for use with the adjustable implant deployment system of FIG. 22;

FIG. 23 is a schematic cross sectional view of another embodiment of a slider assembly;

FIG. 27 is a cross sectional view taken along cut line 27-27 of FIG. 26;

FIG. 28 is a schematic cross sectional view of a slider assembly incorporating quick-disconnect functionality;

FIG. 32 is a schematic view of a delivery system constructed in accordance with one embodiment of the present invention;

FIG. 32A is a cross sectional view of a deployment catheter as shown in FIG. 32, taken along cut line 32A-32A.

FIG. 37 is a partial cross sectional view of an axially moveable core used in the system of FIG. 32;

FIG. 37A is a cross sectional view of the axially moveable core of FIG. 37 taken along cut line 37A-37A;

FIGS. 38A-C are a schematic view of a delivery sheath used in combination with the system of FIG. 32;

FIG. 45 a schematic view of a delivery system attached to an implantable containment device in accordance with another embodiment;

FIG. 46 is a partial cross-sectional schematic view of a delivery system attached to an implantable containment device in accordance with another embodiment; and FIG. 47 is a schematic view of the delivery system shown in FIG. 46.

DETAILED DESCRIPTION OF THE PREFERRED EMBODIMENTS

Figure 1:
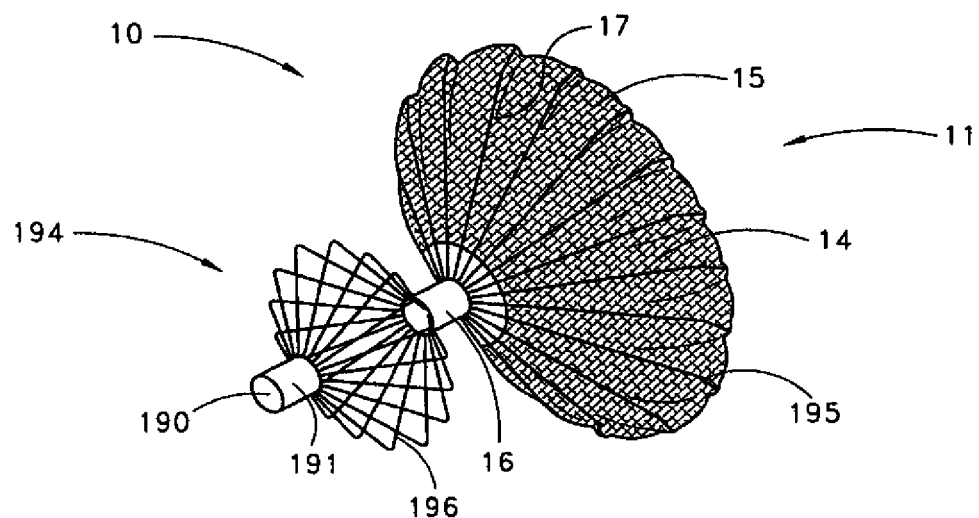
FIG. 1 is a perspective view of a containment device in accordance with one embodiment of the present invention.
Figure 2:
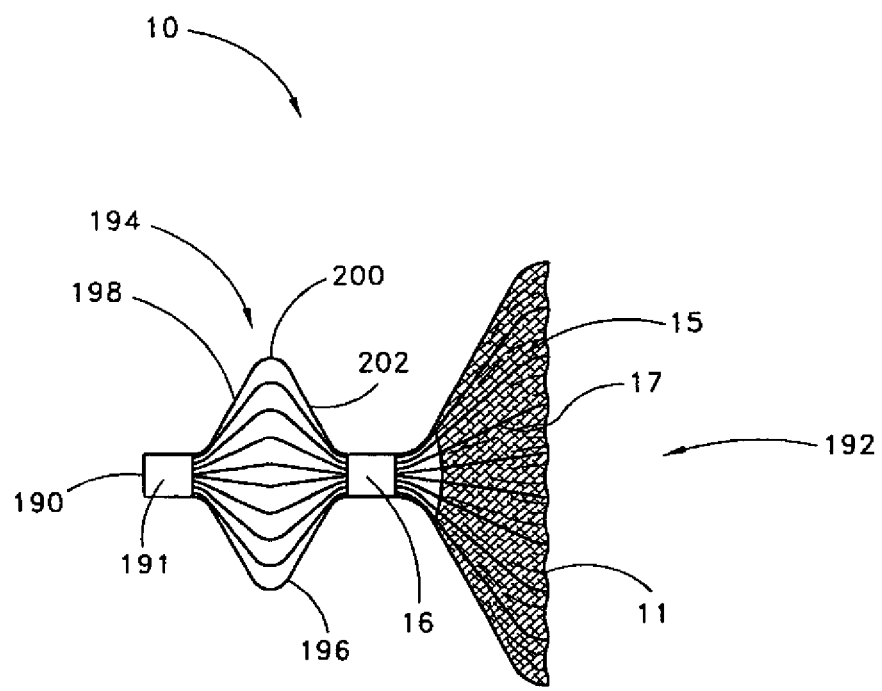
FIG. 2 is a side elevational view of the containment device shown in FIG. 1.

Referring to FIGS. 1 and 2, there is illustrated one embodiment of an occlusion or containment device 10 in accordance with the present invention. Although the present invention will be described primarily in the context of an occlusion device, the present inventors also contemplate omitting the fabric cover or enlarging the pore size to produce implantable filters or other devices which are enlargeable at a remote implantation site. The terms "occlusion device" or "containment device" are intended to encompass all such devices.

The occlusion device 10 comprises an occluding member 11 comprising a frame 14 and a barrier 15. In the illustrated embodiment, the frame 14 comprises a plurality of radially outwardly extending spokes 17 each having a length within the range of from about 0.5 cm to about 2 cm from a hub 16. In one embodiment, the spokes have an axial length of about 1.5 cm. Depending upon the desired introduction crossing profile of the collapsed occlusion device 10, as well as structural strength requirements in the deployed device, anywhere within the range of from about 3 spokes to about 40 spokes may be utilized. In some embodiments, anywhere from about 12 to about 24 spokes are utilized, and, 18 spokes are utilized in one embodiment.

The spokes are advanceable from a generally axially extending orientation such as to fit within a tubular introduction catheter to a radially inclined orientation as illustrated in FIG. 1 and FIG. 2 following deployment from the catheter. In a self-expandable embodiment, the spokes are biased radially outwardly such that the occlusion member expands to its enlarged, implantation cross-section under its own bias following deployment from the catheter. Alternatively, the occlusion member may be enlarged using any of a variety of enlargement structures such as an inflatable balloon, or a catheter for axially shortening the occlusion member, as is discussed further below.

Preferably, the spokes comprise a metal such as stainless steel, nitinol, Elgiloy, or others which can be determined through routine experimentation by those of skill in the art. Wires having a circular or rectangular cross-section may be utilized depending upon the manufacturing technique. In one embodiment, rectangular cross section spokes are cut such as by known laser cutting techniques from tube stock, a portion of which forms the hub 16.

The barrier 15 may comprise any of a variety of materials which facilitate cellular in-growth, such as ePTFE. The suitability of alternate materials for barrier 15 can be determined through routine experimentation by those of skill in the art. The barrier 15 may be provided on either one or both axially facing sides of the occlusion member. In one embodiment, the barrier 15 comprises two layers, with one layer on each side of the frame 14. The two layers may be bonded to each other around the spokes 17 in any of a variety of ways, such as by heat bonding with or without an intermediate bonding layer such as polyethylene or FEP, adhesives, sutures, and other techniques which will be apparent to those of skill in the art in view of the disclosure herein. The barrier 15 preferably has a thickness of no more than about 0.006" and a porosity within the range of from about 5 .mu.m to about 60 .mu.m.

The barrier 15 in one embodiment preferably is securely attached to the frame 14 and retains a sufficient porosity to facilitate cellular ingrowth and/or attachment. One method of manufacturing a suitable composite membrane barrier 15 is illustrated in FIGS. 13-16. As illustrated schematically in FIG. 13, a bonding layer 254 preferably comprises a mesh or other porous structure having an open surface area within the range of from about 10% to about 90%. Preferably, the open surface area of the mesh is within the range of from about 30% to about 60%. The opening or pore size of the bonding layer 254 is preferably within the range of from about 0.005 inches to about 0.050 inches, and, in one embodiment, is about 0.020 inches. The thickness of the bonding layer 254 can be varied widely, and is generally within the range of from about 0.0005 inches to about 0.005 inches. In a preferred embodiment, the bonding layer 254 has a thickness of about 0.001 to about 0.002 inches. One suitable polyethylene bonding mesh is available from Smith and Nephew, under the code SN9.

Figure 14:
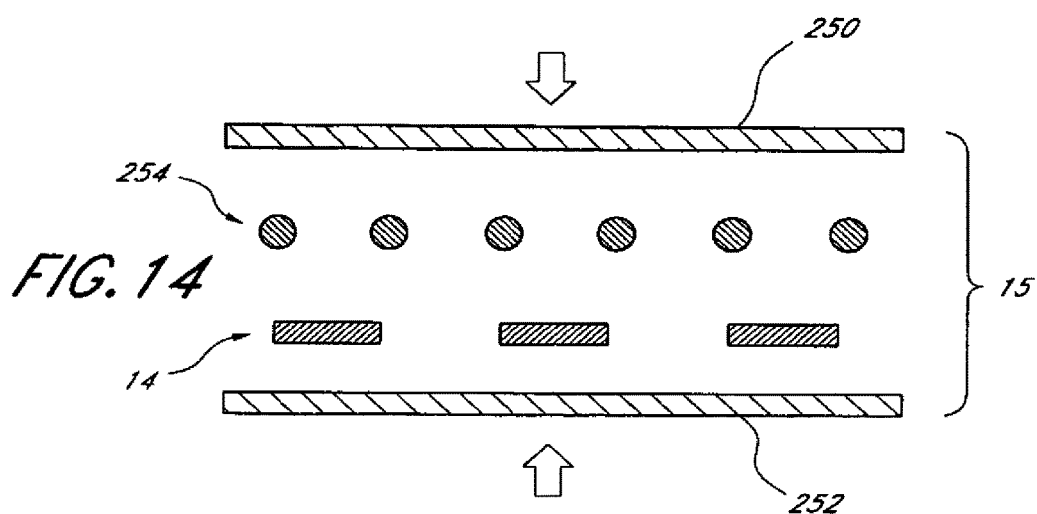
FIG. 14 is an exploded cross sectional view of the components of a composite barrier member in accordance with an embodiment of the present invention.
Figure 15:
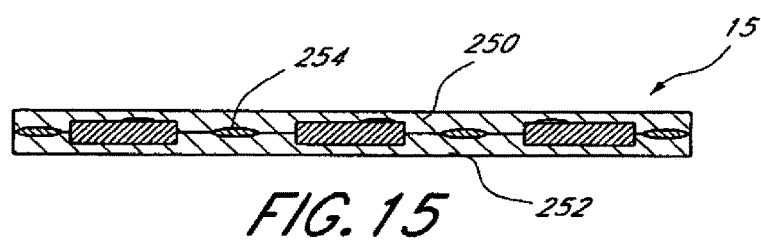
FIG. 15 is a cross sectional view through a composite barrier formed from the components illustrated in FIG. 14.

Referring to FIG. 14, the bonding layer 254 is preferably placed adjacent one or both sides of a spoke or other frame element 14. The bonding layer 254 and frame 14 layers are then positioned in-between a first membrane 250 and a second membrane 252 to provide a composite membrane stack. The first membrane 250 and second membrane 252 may comprise any of a variety of materials and thicknesses, depending upon the desired functional result. Generally, the membrane has a thickness within the range of from about 0.0005 inches to about 0.010 inches. In one embodiment, the membranes 250 and 252 each have a thickness on the order of from about 0.001 inches to about 0.002 inches, and comprise porous ePTFE, having a porosity within the range of from about 10 microns to about 100 microns.

The composite stack is heated to a temperature of from about 200.degree. F. to about 300.degree. F., for about 1 minute to about 5 minutes under pressure to provide a finished composite membrane assembly with an embedded frame 14 as illustrated schematically in FIG. 15. The final composite membrane has a thickness within the range of from about 0.001 inches to about 0.010 inches, and, preferably, is about 0.002 to about 0.003 inches in thickness. However, the thicknesses and process parameters of the foregoing may be varied considerably, depending upon the materials of the bonding layer 254 the first layer 250 and the second layer 252.

Figure 16:
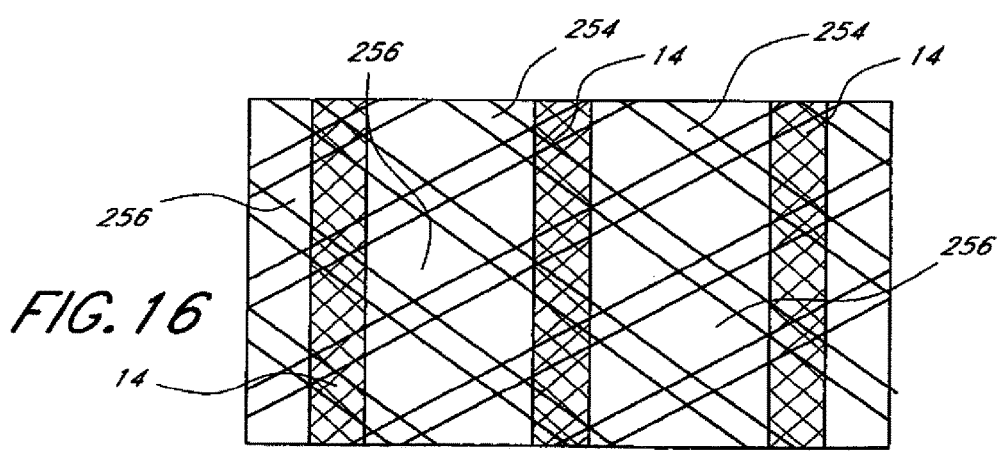
FIG. 16 is a top plan view of the composite barrier illustrated in FIG. 15.

As illustrated in top plan view in FIG. 16, the resulting finished composite membrane has a plurality of "unbonded" windows or areas 256 suitable for cellular attachment and/or ingrowth. The attachment areas 256 are bounded by the frame 14 struts, and the cross-hatch or other wall pattern formed by the bonding layer 254. Preferably, a regular window 256 pattern is produced in the bonding layer 254.

The foregoing procedure allows the bonding mesh to flow into the first and second membranes 250 and 252 and gives the composite membrane 15 greater strength (both tensile and tear strength) than the components without the bonding mesh. The composite allows uniform bonding while maintaining porosity of the membrane 15, to facilitate tissue attachment. By flowing the thermoplastic bonding layer into the pores of the outer mesh layers 250 and 252, the composite flexibility is preserved and the overall composite layer thickness can be minimized.

Referring back to FIGS. 1 and 2, the occlusion device 10 may be further provided with a bulking element or stabilizer 194. The stabilizer 194 may be spaced apart along an axis from the occluding member 11. In the illustrated embodiment, a distal end 190 and a proximal end 192 are identified for reference. The designation proximal or distal is not intended to indicate any particular anatomical orientation or deployment orientation within the deployment catheter. As shown in FIGS. 1 and 2, the stabilizer 194 is spaced distally apart from the occluding member 11.

For use in the LAA, the occluding member 11 has an expanded diameter within the range of from about 1 cm to about 5 cm, and, in one embodiment, about 3 cm. The axial length of the occluding member 11 in an expanded, unstressed orientation from the distal end 192 to the hub 16 is on the order of about 1 cm. The overall length of the occlusion device 10 from the distal end 192 to the proximal end 190 is within the range of from about 1.5 cm to about 4 cm and, in one embodiment, about 2.5 cm. The axial length of the stabilizer 194 between distal hub 191 and proximal hub 16 is within the range of from about 0.5 cm to about 2 cm, and, in one embodiment, about 1 cm. The expanded diameter of the stabilizer 194 is within the range of from about 0.5 cm to about 2.5 cm, and, in one embodiment, about 1.4 cm. The outside diameter of the distal hub 191 and proximal hub 16 is about 2.5 mm.

Preferably, the occlusion device 10 is provided with one or more retention structures for retaining the device in the left atrial appendage or other body cavity or lumen. In the illustrated embodiment, a plurality of barbs or other anchors 195 are provided, for engaging adjacent tissue to retain the occlusion device 10 in its implanted position and to limit relative movement between the tissue and the occlusion device. The illustrated anchors are provided on one or more of the spokes 17, or other portion of frame 14. Preferably, every spoke, every second spoke or every third spoke are provided with one or two or more anchors each.

The illustrated anchor is in the form of a barb, with one on each spoke for extending into tissue at or near the opening of the LAA. Depending upon the embodiment, two or three barbs may alternatively be desired on each spoke. In the single barb embodiment of FIG. 7, each barb is inclined in a proximal direction. This is to inhibit proximal migration of the implant out of the left atrial appendage. In this context, distal refers to the direction into the left atrial appendage, and proximal refers to the direction from the left atrial appendage into the heart.

Alternatively, one or more barbs may face distally, to inhibit distal migration of the occlusion device deeper into the LAA. Thus the implant may be provided with at least one proximally facing barb and at least one distally facing barb. For example, in an embodiment of the type illustrated in FIG. 12, discussed below, a proximal plurality of barbs may be inclined in a first direction, and a distal plurality of barbs may be inclined in a second direction, to anchor the implant against both proximal and distal migration.

One or more anchors 195 may also be provided on the stabilizer 194, such that it assists not only in orienting the occlusion device 10 and resisting compression of the LAA, but also in retaining the occlusion device 10 within the LAA. Any of a wide variety of structures may be utilized for anchor 195, either on the occluding member 11 or the stabilizer 194 or both, such as hooks, barbs, pins, sutures, adhesives, ingrowth surfaces and others which will be apparent to those of skill in the art in view of the disclosure herein.

In use, the occlusion device 10 is preferably positioned within a tubular anatomical structure to be occluded such as the left atrial appendage. In a left atrial appendage application, the occluding member 11 is positioned across or near the opening to the LAA and the stabilizer 194 is positioned within the LAA. The stabilizer 194 assists in the proper location and orientation of the occluding member 11, as well as resists compression of the LAA behind the occluding member 11. The present inventors have determined that following deployment of an occluding member 11 without a stabilizer 194 or other bulking structure to resist compression of the LAA, normal operation of the heart may cause compression and resulting volume changes in the LAA, thereby forcing fluid past the occluding member 11 and inhibiting or preventing a complete seal. Provision of a stabilizer 194 dimensioned to prevent the collapse or pumping of the LAA thus minimizes leakage, and provision of the barbs facilitates endothelialization or other cell growth across the occluding member 11.

The stabilizer 194 is preferably movable between a reduced cross-sectional profile for transluminal advancement into the left atrial appendage, and an enlarged cross-sectional orientation as illustrated to fill or to substantially fill a cross-section through the LAA. The stabilizing member may enlarge to a greater cross section than the (pre-stretched) anatomical cavity, to ensure a tight fit and minimize the likelihood of compression. One convenient construction includes a plurality of elements 196 which are radially outwardly expandable in response to axial compression of a distal hub 191 towards a proximal hub 16. Elements 196 each comprise a distal segment 198 and a proximal segment 202 connected by a bend 200. The elements 196 may be provided with a bias in the direction of the radially enlarged orientation as illustrated in FIG. 2, or may be radially expanded by applying an expansion force such as an axially compressive force between distal hub 191 and proximal hub 16 or a radial expansion force such as might be applied by an inflatable balloon. Elements 196 may conveniently be formed by laser cutting the same tube stock as utilized to construct the distal hub 191, proximal hub 16 and frame 14, as will be apparent to those of skill in the art in view of the disclosure herein. Alternatively, the various components of the occlusion device 10 may be separately fabricated or fabricated in subassemblies and secured together during manufacturing.

As a post implantation step for any of the occlusion devices disclosed herein, a radiopaque dye or other visualizeable media may be introduced on one side or the other of the occlusion device, to permit visualization of any escaped blood or other fluid past the occlusion device. For example, in the context of a left atrial appendage application, the occlusion device may be provided with a central lumen or other capillary tube or aperture which permits introduction of a visualizeable dye from the deployment catheter through the occlusion device and into the entrapped space on the distal side of the occlusion device. Alternatively, dye may be introduced into the entrapped space distal to the occlusion device such as by advancing a small gauge needle from the deployment catheter through the barrier 15 on the occlusion device, to introduce dye.

Figure 3:
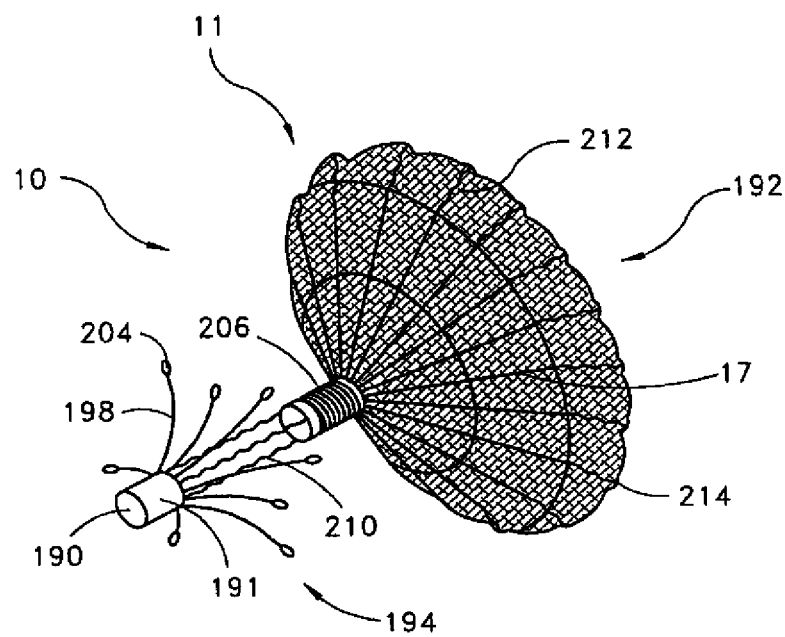
FIG. 3 is a perspective view of a containment device in accordance with an alternate embodiment of the present invention.
Figure 4:
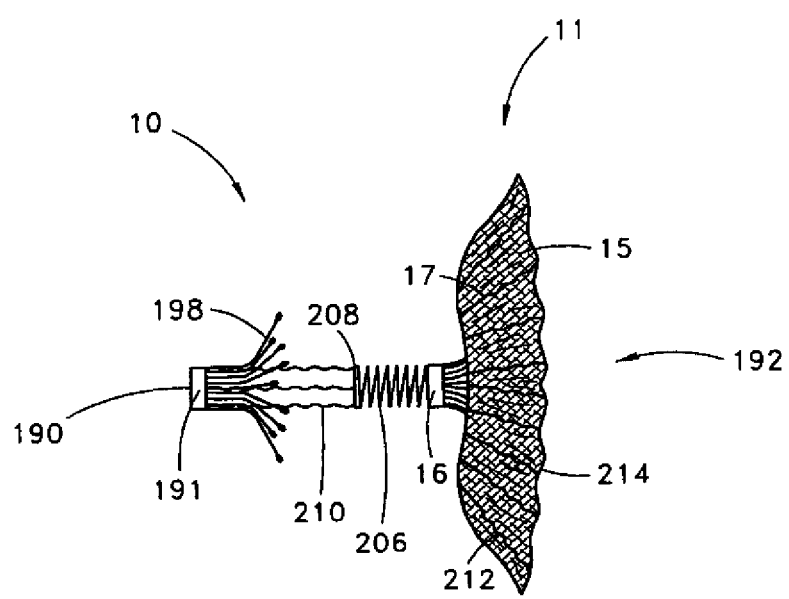
FIG. 4 is a side elevational view of the embodiment shown in FIG. 3.

Modifications to the occlusion device 10 are illustrated in FIGS. 3-4. The occlusion device 10 comprises an occlusion member 11 and a stabilizing member 194 as previously discussed. In the present embodiment, however, each of the distal segments 198 inclines radially outwardly in the proximal direction and terminates in a proximal end 204. The proximal end 204 may be provided with an atraumatic configuration, for pressing against, but not penetrating, the wall of the left atrial appendage or other tubular body structure. Three or more distal segments 198 are preferably provided, and generally anywhere within the range of from about 6 to about 20 distal segments 198 may be used. In one embodiment, 9 distal segments 198 are provided. In this embodiment, three of the distal segments 198 have an axial length of about 5 mm, and 6 of the distal segments 198 have an axial length of about 1 cm. Staggering the lengths of the distal segments 198 may axially elongate the zone in the left atrial appendage against which the proximal ends 204 provide anchoring support for the occlusion device.

The occlusion device 10 illustrated in FIGS. 3 and 4 is additionally provided with a hinge 206 to allow the longitudinal axis of the occlusion member 11 to be angularly oriented with respect to the longitudinal axis of the stabilizing member 194. In the illustrated embodiment, the hinge 206 is a helical coil, although any of a variety of hinge structures can be utilized. The illustrated embodiment may be conveniently formed by laser cutting a helical slot through a section of the tube from which the principal structural components of the occlusion device 10 are formed. At the distal end of the hinge 206, an annular band 208 connects the hinge 206 to a plurality of axially extending struts 210. In the illustrated embodiment, three axial struts 210 are provided, spaced equilaterally around the circumference of the body. Axial struts 210 may be formed from a portion of the wall of the original tube stock, which portion is left in its original axial orientation following formation of the distal segments 198 such as by laser cutting from the tubular wall.

The occlusion member 11 is provided with a proximal zone 212 on each of the spokes 17. Proximal zone 212 has an enhanced degree of flexibility, to accommodate the fit between the occlusion member 11 and the wall of the left atrial appendage. Proximal section 212 may be formed by reducing the cross sectional area of each of the spokes 17, which may be provided with a wave pattern as illustrated.

Each of the spokes 17 terminates in a proximal point 214. Proximal point 214 may be contained within layers of the barrier 15, or may extend through or beyond the barrier 15 such as to engage adjacent tissue and assist in retaining the occlusion device 10 at the deployment site.

Figure 5:
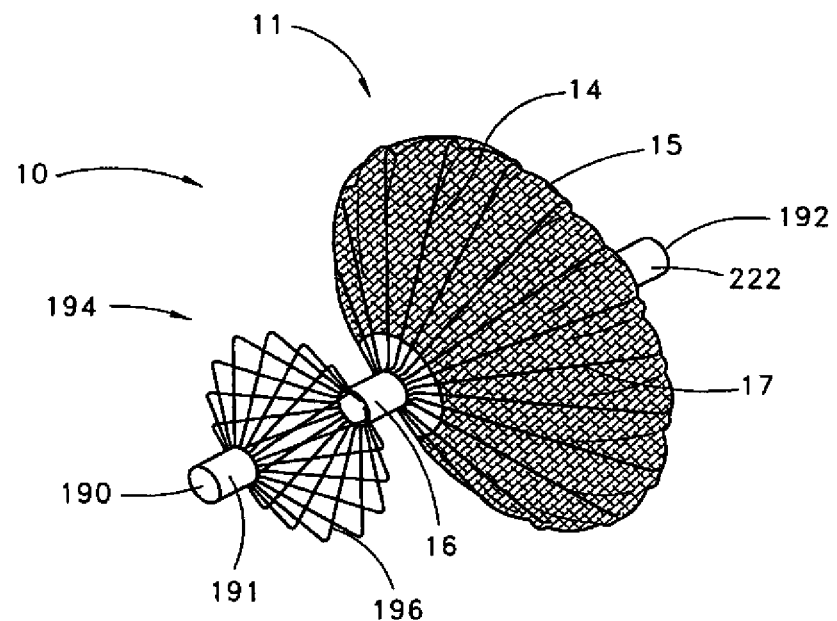
FIG. 5 is a perspective view of a containment device in accordance with a further embodiment of the present invention.
Figure 6:
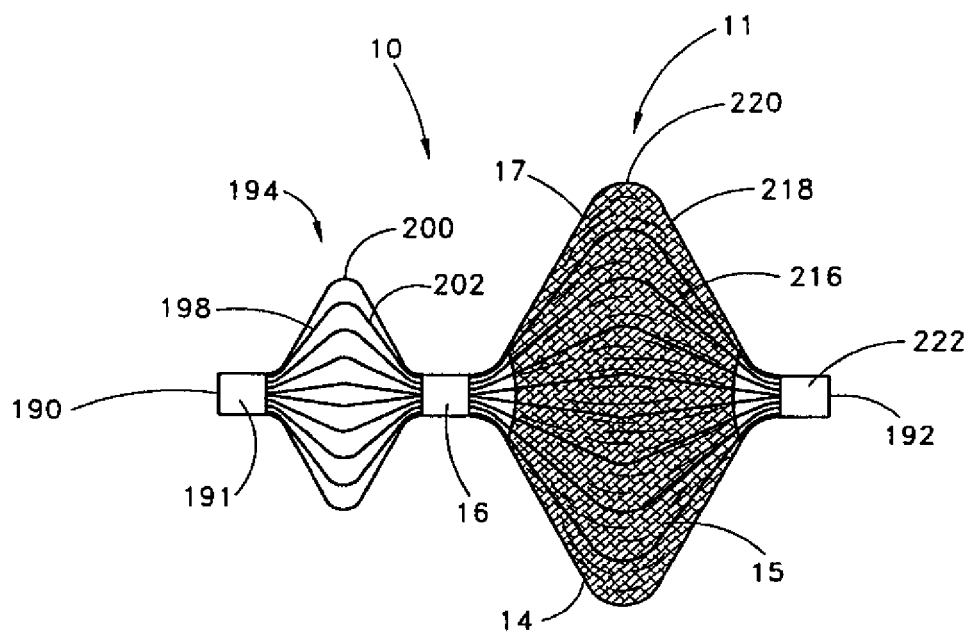
FIG. 6 is a side elevational view of the embodiment of FIG. 5.

Referring to FIGS. 5 and 6, a further variation on the occlusion device 10 illustrated in FIGS. 1 and 2 is provided. The occlusion device 10 is provided with a proximal face 216 on the occlusion member 11, instead of the open and proximally concave face on the embodiment of FIGS. 1 and 2. The proximal face 216 is formed by providing a proximal spoke 218 which connects at an apex 220 to some or all of the distal spokes 17. The proximal spoke 218, and corresponding apex 220 and distal spoke 17 may be an integral structure, such as a single ribbon or wire, or element cut from a tube stock as has been discussed.

Proximal spokes 218 are each attached to a hub 222 at the proximal end 192 of the occlusion device 10. The barrier 15 may surround either the proximal face or the distal face or both on the occlusion member 11. In general, provision of a proximal spoke 218 connected by an apex 220 to a distal spoke 17 provides a greater radial force than a distal spoke 17 alone, which will provide an increased resistance to compression if the occlusion member 11 is positioned with the LAA.

Referring to FIGS. 7-12, alternate structures of the occlusion device in accordance with the present invention are illustrated. In general, the occlusion device 10 comprises an occluding member but does not include a distinct stabilizing member as has been illustrated in connection with previous embodiments. Any of the embodiments previously disclosed herein may also be constructed using the occluding member only, and omitting the stabilizing member as will be apparent to those of skill in the art in view of the disclosure herein.

The occluding device 10 comprises a proximal end 192, a distal end 190, and a longitudinal axis extending therebetween. A plurality of supports 228 extend between a proximal hub 222 and a distal hub 191. At least two or three supports 228 are provided, and preferably at least about ten. In one embodiment, sixteen supports 228 are provided. However, the precise number of supports 228 can be modified, depending upon the desired physical properties of the occlusion device 10 as will be apparent to those of skill in the art in view of the disclosure herein, without departing from the present invention.

Each support 228 comprises a proximal spoke portion 218, a distal spoke portion 17, and an apex 220 as has been discussed. Each of the proximal spoke portion 218, distal spoke portion 17 and apex 220 may be a region on an integral support 228, such as a continuous rib or frame member which extends in a generally curved configuration as illustrated with a concavity facing towards the longitudinal axis of the occlusion device 10. Thus, no distinct point or hinge at apex 220 is necessarily provided.

At least some of the supports 228, and, preferably, each support 228, is provided with one or two or more barbs 195. In the illustrated configuration, the occlusion device 10 is in its enlarged orientation, such as for occluding a left atrial appendage or other body cavity or lumen. In this orientation, each of the barbs 195 projects generally radially outwardly from the longitudinal axis, and is inclined in the proximal direction. One or more barbs may also be inclined distally, as is discussed elsewhere herein. In an embodiment where the barbs 195 and corresponding support 228 are cut from a single ribbon, sheet or tube stock, the barb 195 will incline radially outwardly at approximately a tangent to the curve formed by the support 228.

Figure 7B:
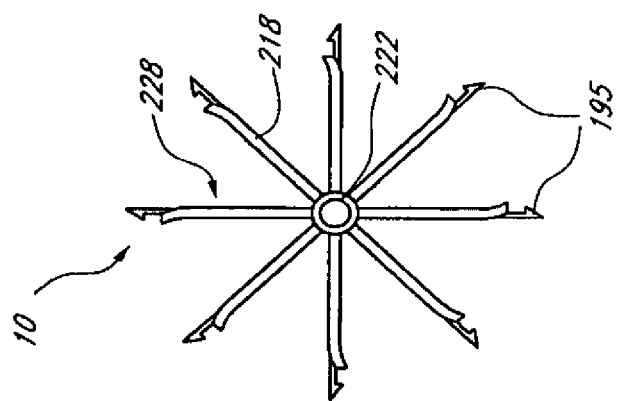
FIG. 7B is an end view taken along the line 7B-7B of FIG. 7A.
Figure 7A:
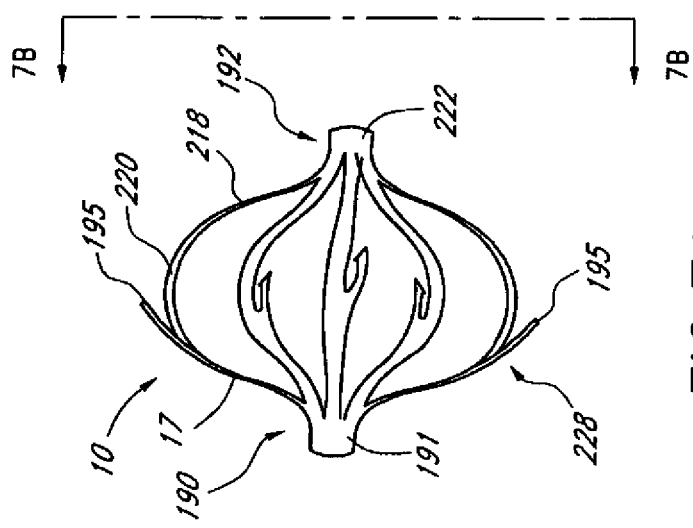
FIG. 7A is a side elevational view of the device of FIG. 7.
Figure 7:
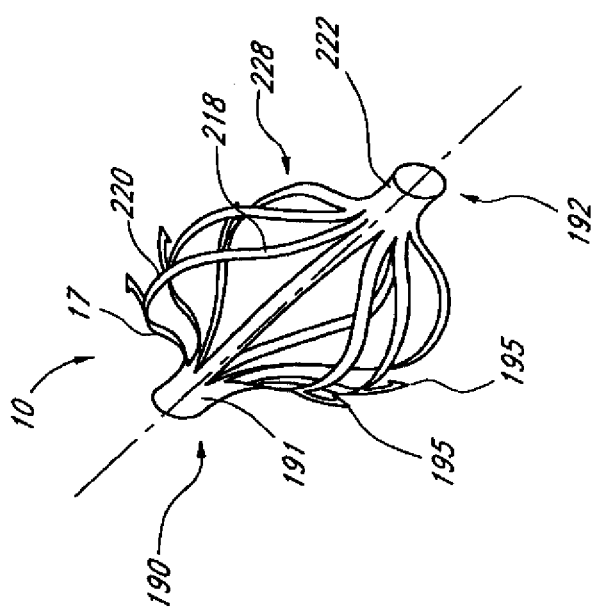
FIG. 7 is a perspective view of a support structure for a containment device in accordance with a further embodiment of the present invention.
Figure 9:
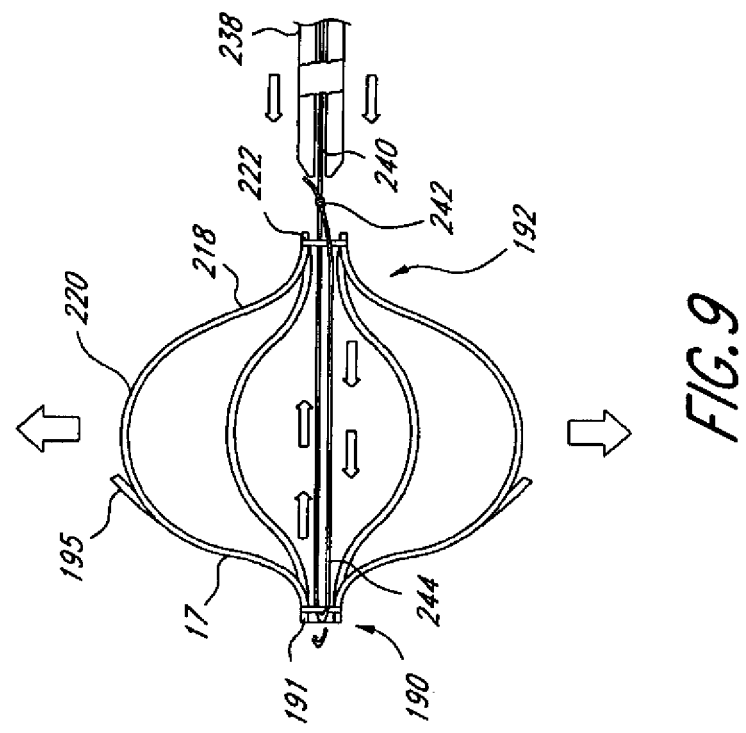
FIG. 9 is a schematic view of a pull string deployment embodiment of the containment device of FIG. 7.

The occlusion device 10 constructed from the frame illustrated in FIG. 7 may be constructed in any of a variety of ways, as will become apparent to those of skill in the art in view of the disclosure herein. In one method, the occlusion device 10 is constructed by laser cutting a piece of tube stock to provide a plurality of axially extending slots in-between adjacent supports 228. Similarly, each barb 195 can be laser cut from the corresponding support 228 or space in-between adjacent supports 228. The generally axially extending slots which separate adjacent supports 228 end a sufficient distance from each of the proximal end 192 and distal end 190 to leave a proximal hub 222 and a distal hub 191 to which each of the supports 228 will attach. In this manner, an integral cage structure may be formed. Alternatively, each of the components of the cage structure may be separately formed and attached together such as through soldering, brazing, heat bonding, adhesives, and other fastening techniques which are known in the art. A further method of manufacturing the occlusion device 10 is to laser cut a slot pattern on a flat sheet of appropriate material, such as a flexible metal or polymer, as has been discussed in connection with previous embodiments. The flat sheet may thereafter be rolled about an axis and opposing edges bonded together to form a tubular structure.

The apex portion 220 which carries the barb 195 may be advanced from a low profile orientation in which each of the supports 228 extend generally parallel to the longitudinal axis, to an implanted orientation as illustrated, in which the apex 220 and the barb 195 are positioned radially outwardly from the longitudinal axis. The support 228 may be biased towards the enlarged orientation, or may be advanced to the enlarged orientation under positive force following positioning within the tubular anatomical structure, in any of a variety of manners.

Figure 8:
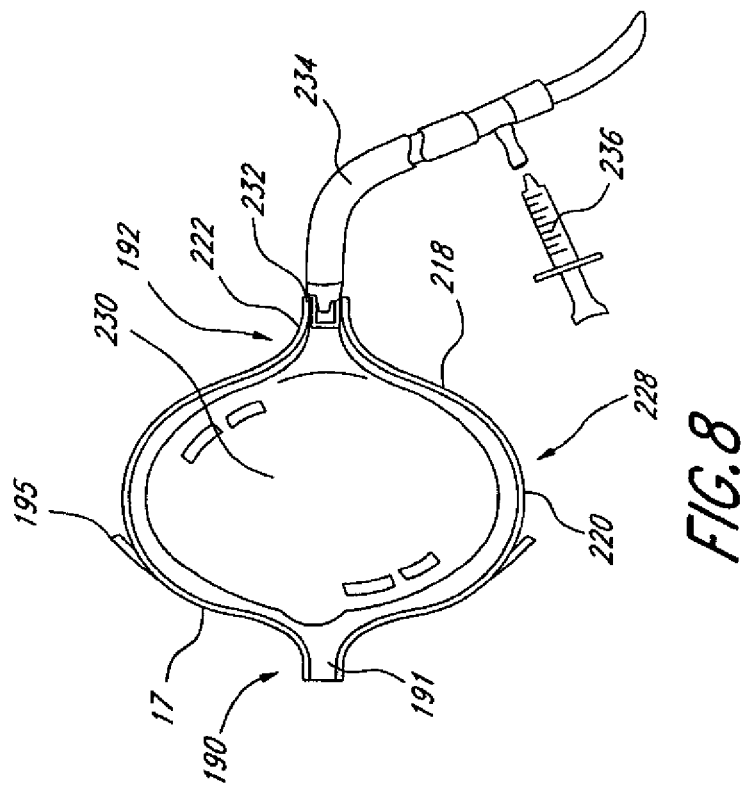
FIG. 8 is a schematic illustration of an inflatable balloon positioned within the containment device of FIG. 7.
Figure 13:
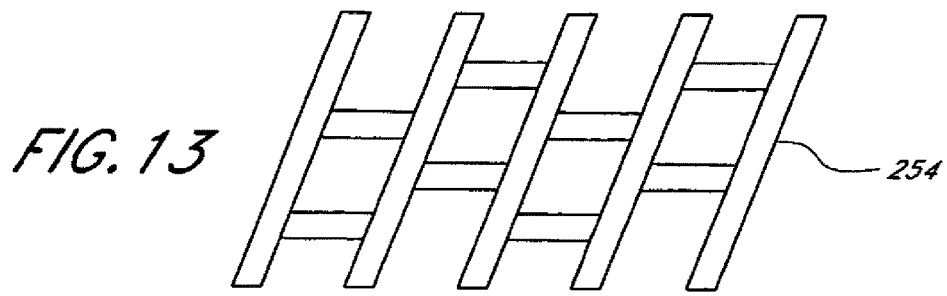
FIG. 13 is a schematic view of a bonding layer mesh for use in forming a composite barrier membrane in accordance with an embodiment of the present invention.

For an example of enlarging under positive force, referring to FIG. 8, an inflatable balloon 230 is positioned within the occlusion device 10. Inflatable balloon 230 is connected by way of a removable coupling 232 to an inflation catheter 234. Inflation catheter 234 is provided with an inflation lumen for providing communication between an inflation media source 236 outside of the patient and the balloon 230. Following positioning within the target body lumen, the balloon 230 is inflated, thereby engaging barbs 195 with the surrounding tissue. The inflation catheter 234 is thereafter removed, by decoupling the removable coupling 232, and the inflation catheter 234 is thereafter removed. The balloon 230 may be either left in place within the occlusion device 10, or deflated and removed by the inflation catheter 234.

In an alternate embodiment, the supports 228 are radially enlarged such as through the use of a deployment catheter 238. See FIG. 9. Deployment catheter 238 comprises a lumen for movably receiving a deployment element such as a flexible line 240. Deployment line 240 extends in a loop 244 formed by an aperture or slip knot 242. As will be apparent from FIG. 9, proximal retraction on the deployment line 240 while resisting proximal movement of proximal hub 222 such as by using the distal end of the catheter 238 will cause the distal hub 191 to be drawn towards the proximal hub 222, thereby radially enlarging the cross-sectional area of the occlusion device 10. Depending upon the material utilized for the occlusion device 10, the supports 228 will retain the radially enlarged orientation by elastic deformation, or may be retained in the enlarged orientation such as by securing the slip knot 242 immovably to the deployment line 240 at the fully radially enlarged orientation. This may be accomplished in any of a variety of ways, using additional knots, clips, adhesives, or other techniques known in the art.

A variety of alternative structures may be utilized, to open or enlarge the occlusion device 10 under positive force. For example, referring to FIG. 9, a pull wire 240 may be removably attached to the distal hub 191 or other distal point of attachment on the occlusion device 10. Proximal retraction of the pull wire 240 while resisting proximal motion of the proximal hub 222 such as by using the distal end of the catheter 238 will cause enlargement of the occlusion device 10 as has been discussed. The pull wire 240 may then be locked with respect to the proximal hub 222 and severed or otherwise detached to enable removal of the deployment catheter 238 and retraction of the pull wire 240. Locking of the pull wire with respect to the proximal hub 222 may be accomplished in any of a variety of ways, such as by using interference fit or friction fit structures, adhesives, a knot or other technique depending upon the desired catheter design.

Referring to FIGS. 10 and 11, the occlusion device 10 may be provided with a barrier 15 such as a mesh or fabric as has been previously discussed. Barrier 15 may be provided on only one hemisphere such as proximal face 216, or may be carried by the entire occlusion device 10 from proximal end 192 to distal end 190. The barrier may be secured to the radially inwardly facing surface of the supports 228, as illustrated in FIG. 11, or may be provided on the radially outwardly facing surfaces of supports 228, or both.

A further embodiment of the occlusion device 10 is illustrated in FIG. 12, in which the apex 220 is elongated in an axial direction to provide additional contact area between the occlusion device 10 and the wall of the tubular structure. In this embodiment, one or two or three or more anchors 195 may be provided on each support 228, depending upon the desired clinical performance. The occlusion device 10 illustrated in FIG. 12 may also be provided with any of a variety of other features discussed herein, such as a partial or complete barrier 15. In addition, the occlusion device 10 illustrated in FIG. 12 may be enlarged using any of the techniques disclosed elsewhere herein.

Figure 17A:
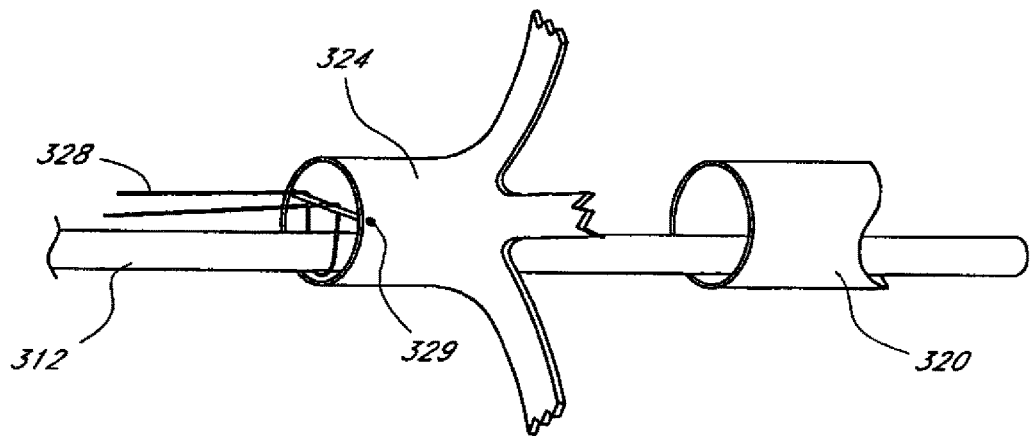
FIG. 17A is an enlarged view of the deployment system of FIG. 17, showing a releasable lock in an engaged configuration.
Figure 17B:
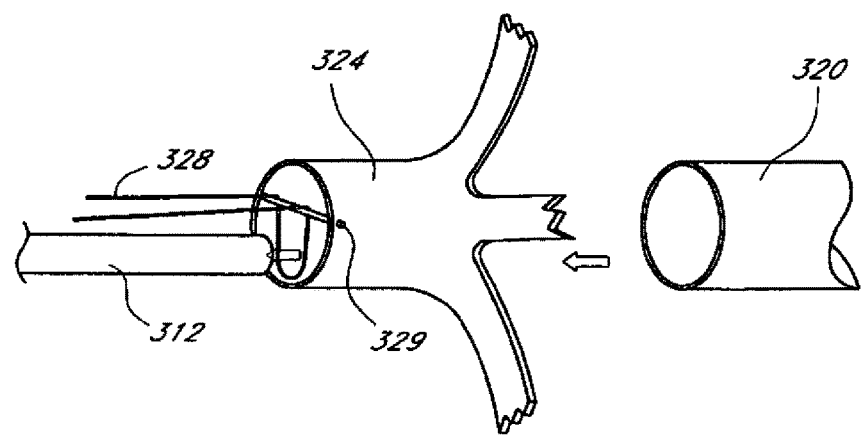
FIG. 17B is an enlarged view as in FIG. 17A, with a core axially retracted to release the implant.

Referring to FIG. 17, there is schematically illustrated a further embodiment of the present invention. An adjustable implant deployment system 300 comprises generally a catheter 302 for placing a detachable implant 304 within a body cavity or lumen, as has been discussed. The catheter 302 comprises an elongate flexible tubular body 306, extending between a proximal end 308 and a distal end 310. The catheter is shown in highly schematic form, for the purpose of illustrating the functional aspects thereof. In one embodiment, the catheter body will have a sufficient length and diameter to permit percutaneous entry into the vascular system, and transluminal advancement through the vascular system to the desired deployment site. For example, in an embodiment intended for access at the femoral vein and deployment within the left atrial appendage, the catheter 302 will have a length within the range of from about 50 cm to about 150 cm, and a diameter of generally no more than about 15 French. Those skilled in the art recognize that the implant deployment system 300 can be configured and sized for various methods of deploying implant 304, as described below. The catheter 302 can be sized and configured so that an implant 304 can be delivered using, for example, conventional transthoracic surgical, minimally invasive, or port access approaches. The deployment system 300 can be used to deploy the implant 304 using methods shown in FIGS. 40-42 and described below. Further dimensions and physical characteristics of catheters for navigation to particular sites within the body are well understood in the art.

The tubular body 306 is further provided with a handle 309 generally on the proximal end 308 of the catheter 302. The handle 309 permits manipulation of the various aspects of the implant deployment system 300, as will be discussed below. Handle 309 may be manufactured in any of a variety of ways, typically by injection molding or otherwise forming a handpiece for single-hand operation, using materials and construction techniques well known in the medical device arts.

The implant 304 may be in the form of any of those described previously herein, as modified below. In general, the implant is movable from a reduced crossing profile to an enlarged crossing profile, such that it may be positioned within a body structure and advanced from its reduced to its enlarged crossing profile to obstruct blood flow or perform other functions while anchored therein. The implant 304 may be biased in the direction of the enlarged crossing profile, may be neutrally biased or may be biased in the direction of the reduced crossing profile. Any modifications to the device and deployment system to accommodate these various aspects of the implant 304 may be readily accomplished by those of skill in the art in view of the disclosure herein.

In the illustrated embodiment, the distal end 314 of the implant 304 is provided with an implant plug 316. Implant plug 316 provides a stopping surface 317 for contacting an axially movable core 312. The core 312 extends axially throughout the length of the catheter body 302, and is attached at its proximal end to a core control 332 on the handle 309.

The core 312 may comprise any of a variety of structures which has sufficient lateral flexibility to permit navigation of the vascular system, and sufficient axial column strength to enable reduction of the implant 304 to its reduced crossing profile. Any of a variety of structures such as hypotube, solid core wire, "bottomed out" coil spring structures, or combinations thereof may be used, depending upon the desired performance of the finished device. In one embodiment, the core 312 comprises stainless steel tubing.

The distal end of core 312 is positioned within a recess or lumen 322 defined by a proximally extending guide tube 320. In the illustrated embodiment, the guide tube 320 is a section of tubing such as metal hypotube, which is attached at the distal end 314 of the implant and extends proximally within the implant 304. The guide tube 320 preferably extends a sufficient distance in the proximal direction to inhibit buckling or prolapse of the core 312 when distal pressure is applied to the core control 332 to reduce the profile of the implant 304. However, the guide tube 320 should not extend proximally a sufficient distance to interfere with the opening of the implant 304.

As will be appreciated by reference to FIG. 17, the guide tube 320 may operate as a limit on distal axial advancement of the proximal end 324 of implant 304. Thus, the guide tube 320 preferably does not extend sufficiently far proximally from the distal end 314 to interfere with optimal opening of the implant 304. The specific dimensions are therefore relative, and will be optimized to suit a particular intended application. In one embodiment, the implant 304 has an implanted outside diameter within the range of from about 5 mm to about 45 mm, and an axial implanted length within the range of from about 5 mm to about 45 mm. The guide tube 320 has an overall length of about 3 mm to about 35 mm, and an outside diameter of about 0.095 inches.

An alternate guide tube 320 is schematically illustrated in FIG. 18. In this configuration, the guide tube 320 comprises a plurality of tubular segments 321 spaced apart by an intervening space 323. This allows increased flexibility of the guide tube 320, which may be desirable during the implantation step, while retaining the ability of the guide tube 320 to maintain linearity of the core 312 while under axial pressure. Although three segments 321 are illustrated in FIG. 18, as many as 10 or 20 or more segments 321 may be desirable depending upon the desired flexibility of the resulting implant.

Each adjacent pair of segments 321 may be joined by a hinge element 325 which permits lateral flexibility. In the illustrated embodiment, the hinge element 325 comprises an axially extending strip or spine, which provides column strength along a first side of the guide tube 320. The guide tube 320 may therefore be curved by compressing or extending a second side of the guide tube 320 which is generally offset from the spine 325 by about 180.degree. A limit on the amount of curvature may be set by adjusting the axial length of the space 323 between adjacent segments 321. In an embodiment having axial spines 325, each axial spine 325 may be rotationally offset from the next adjacent axial spine 325 to enable flexibility of the overall guide tube 320 throughout a 360.degree. angular range of motion.

Alternatively, the flexible hinge point between each adjacent segment 321 may be provided by cutting a spiral groove or plurality of parallel grooves in a tubular element in between what will then become each adjacent pair of segments 321. In this manner, each tubular element 321 will be separated by an integral spring like structure, which can permit flexibility. As a further alternative, the entire length of the guide tube 320 may comprise a spring. Each of the forgoing embodiments may be readily constructed by laser cutting or other cutting from a piece of tube stock, to produce a one piece guide tube 320. Alternatively, the guide tube 320 may be assembled from separate components and fabricated together using any of a variety of bonding techniques which are appropriate for the construction material selected for the tube 320.

Various distal end 314 constructions may be utilized, as will be apparent to those of skill in the art in view of the disclosure herein. In the illustrated embodiment, the distal implant plug 316 extends within the implant 304 and is attached to the distal end of the guide tube 320. The implant plug 316 may be secured to the guide tube 320 and implant 304 in any of a variety of ways, depending upon the various construction materials. For example, any of a variety of metal bonding techniques such as a welding, brazing, interference fit such as threaded fit or snap fit, may be utilized. Alternatively, any of a variety of bonding techniques for dissimilar materials may be utilized, such as adhesives, and various molding techniques. In one construction, the implant plug 316 comprises a molded polyethylene cap, and is held in place utilizing a distal cross pin 318 which extends through the implant 304, the guide tube 320 and the implant plug 316 to provide a secure fit against axial displacement.

The proximal end 324 of the implant 304 is provided with a releasable lock 326 for attachment to a release element such as pull wire 328. Pull wire 328 extends proximally throughout the length of the tubular body 306 to a proximal pull wire control 330 on the handle 309.

As used herein, the term pull wire is intended to include any of a wide variety of structures which are capable of transmitting axial tension or compression such as a pushing or pulling force with or without rotation from the proximal end 308 to the distal end 310 of the catheter 302. Thus, monofilament or multifilament metal or polymeric rods or wires, woven or braided structures may be utilized. Alternatively, tubular elements such as a concentric tube positioned within the outer tubular body 306 may also be used as will be apparent to those of skill in the art.

In the illustrated embodiment, the pull wire 328 is releasably connected to the proximal end 324 of the implant 304. This permits proximal advancement of the proximal end of the implant 304, which cooperates with a distal retention force provided by the core 312 against the distal end of the implant to axially elongate the implant 304 thereby reducing it from its implanted configuration to its reduced profile for implantation. The proximal end of the pull wire 328 may be connected to any of a variety of pull wire controls 330, including rotational knobs, levers and slider switches, depending upon the design preference.

The proximal end 324 of the implant 304 is thus preferably provided with a releasable lock 326 for attachment of the pull wire 328 to the deployment catheter. In the illustrated embodiment, the releasable lock is formed by advancing the pull wire distally around a cross pin 329, and providing an eye or loop which extends around the core 312. As long as the core 312 is in position within the implant 304, proximal retraction of the pull wire 328 will advance the proximal end 324 of the implant 304 in a proximal direction. See FIG. 17A. However, following deployment, proximal retraction of the core 312 such as by manipulation of the core control 332 will pull the distal end of the core 312 through the loop on the distal end of the pull wire 328. The pull wire 328 may then be freely proximally removed from the implant 304, thereby enabling detachment of the implant 304 from the deployment system 300 within a treatment site. See FIG. 17B.

The implant deployment system 300 thus permits the implant 304 to be maintained in a low crossing profile configuration, to enable transluminal navigation to a deployment site. Following positioning at or about the desired deployment site, proximal retraction of the core 312, or distal movement of full wire 528, enables the implant 304 to radially enlarge under its own bias to fit the surrounding tissue structure. Alternatively, the implant can be enlarged under positive force, such as by inflation of a balloon or by a mechanical mechanism as is discussed elsewhere herein. Once the clinician is satisfied with the position of the implant 304, such as by injection of dye and visualization using conventional techniques, the core 312 is proximally retracted thereby releasing the lock 326 and enabling detachment of the implant 304 from the deployment system 300.

If, however, visualization reveals that the implant 304 is not at the location desired by the clinician, proximal retraction of the pull wire 328 with respect to the core 312 will radially reduce the diameter of the implant 304, thereby enabling repositioning of the implant 304 at the desired site. Thus, the present invention permits the implant 304 to be enlarged or reduced by the clinician to permit repositioning and/or removal of the implant 304 as may be desired.

Figure 19:
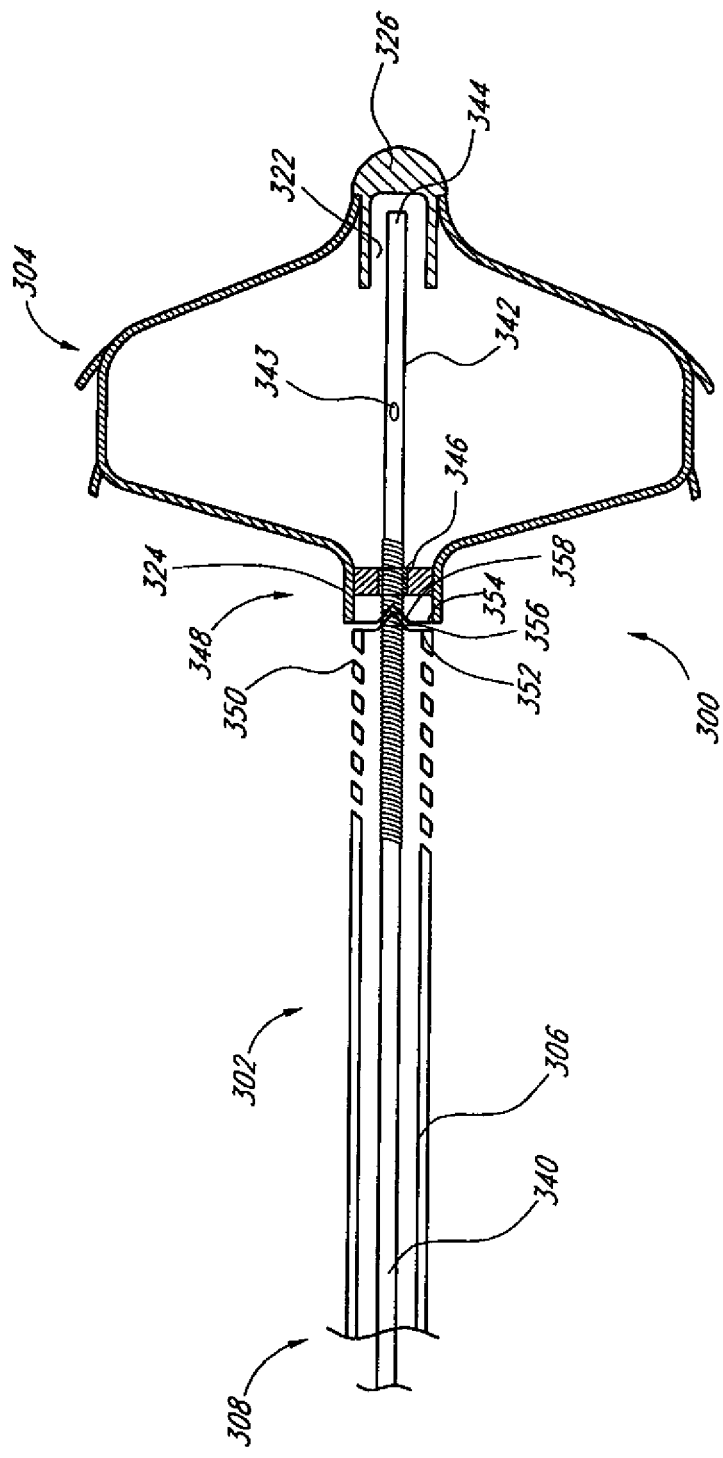
FIG. 19 is a schematic view of an alternate deployment system in accordance with one embodiment of the present invention.

In an alternate construction, the implant may be radially enlarged or reduced by rotating a torque element extending throughout the deployment catheter. Referring to FIG. 19, the elongate flexible tubular body 306 of the deployment catheter 302 includes a rotatable torque rod 340 extending axially therethrough. The proximal end of the torque rod 340 may be connected at a proximal manifold to a manual rotation device such as a hand crank, thumb wheel, rotatable knob or the like. Alternatively, the torque rod 340 may be connected to a power driven source of rotational energy such as a motor drive or air turbine.

The distal end of the torque rod 340 is integral with or is connected to a rotatable core 342 which extends axially through the implant 304. A distal end 344 of the rotatable core 342 is positioned within a cavity 322 as has been discussed.

The terms torque rod or torque element are intended to include any of a wide variety of structures which are capable of transmitting a rotational torque throughout the length of a catheter body. For example, solid core elements such as stainless steel, nitinol or other nickel titanium alloys, or polymeric materials may be utilized. In an embodiment intended for implantation over a guidewire, the torque rod 340 is preferably provided with an axially extending central guidewire lumen. This may be accomplished by constructing the torque rod 340 from a section of hypodermic needle tubing, having an inside diameter of from about 0.001 inches to about 0.005 inches or more greater than the outside diameter of the intended guidewire. Tubular torque rods 340 may also be fabricated or constructed utilizing any of a wide variety of polymeric constructions which include woven or braided reinforcing layers in the wall. Torque transmitting tubes and their methods of construction are well understood in the intracranial access and rotational atherectomy catheter arts, among others, and are not described in greater detail herein. Use of a tubular torque rod 340 also provides a convenient infusion lumen for injection of contrast media within the implant 304, such as through a port 343.

The proximal end 324 of the implant 304 is provided with a threaded aperture 346 through which the core 342 is threadably engaged. As will be appreciated by those of skill in the art in view of the disclosure herein, rotation of the threaded core 342 in a first direction relative to the proximal end 324 of the implant 304 will cause the rotatable core 342 to advance distally. This distal advancement will result in an axial elongation and radial reduction of the implantable device 304. Rotation of the rotatable core 342 in a reverse direction will cause a proximal retraction of the rotatable core 342, thus enabling a radial enlargement and axial shortening of the implantable device 304.

The deployment catheter 302 is further provided with an antirotation lock 348 between a distal end 350 of the tubular body 306 and the proximal end 324 of the implant 304. In general, the rotational lock 348 may be conveniently provided by cooperation between a first surface 352 on the distal end 350 of the deployment catheter 302, which engages a second surface 354 on the proximal end 324 of the implantable device 304, to rotationally link the deployment catheter 302 and the implantable device 304. Any of a variety of complementary surface structures may be provided, such as an axial extension on one of the first and second surfaces for coupling with a corresponding recess on the other of the first and second surfaces. Such extensions and recesses may be positioned laterally offset from the axis of the catheter. Alternatively, they may be provided on the longitudinal axis with any of a variety of axially releasable anti-rotational couplings having at least one flat such as a hexagonal or other multifaceted cross sectional configuration.

Figure 19A:
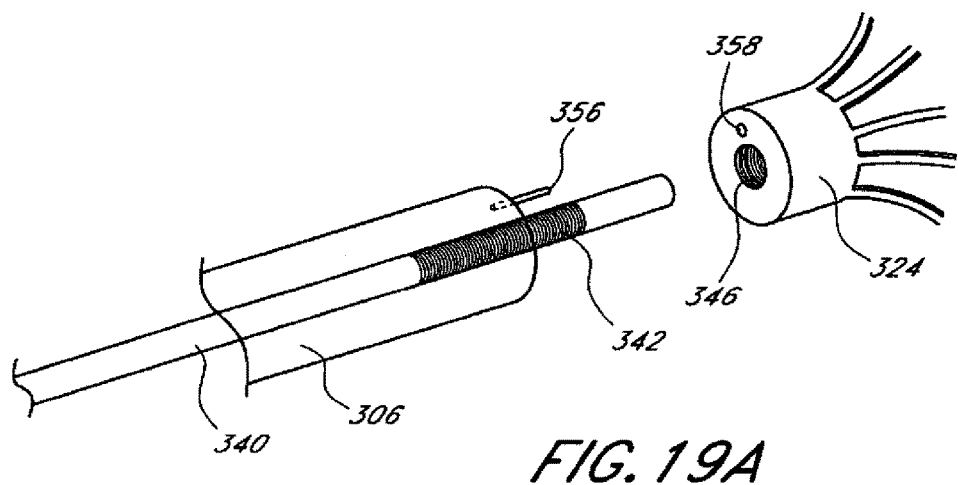
FIGS. 19A-19B illustrate a removal sequence for an implanted device in accordance with one embodiment of the present invention.
Figure 19B:
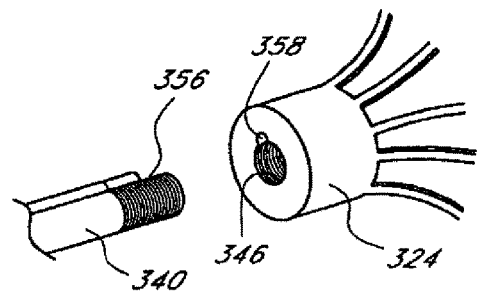

As schematically illustrated in FIGS. 19A and B, one or more projections 356 on the first surface 352 may engage a corresponding recess 358 on the second surface 354. Any of a variety of alternative complementary surface structures may also be provided, as will be apparent to those of skill in the art in view of the disclosure herein. For example, referring to FIG. 19A, the projection 356 is in the form of an axially extending pin for engaging a complimentary recess 358 on the proximal end 324 of the implant 304. FIG. 19B illustrates an axially extending spline 356 for receipt within a complimentary axially extending recess 358. The various pin, spline and other structures may be reversed between the distal end of tubular body 306 and the proximal end 324 of the implant 304 as will be apparent to those of skill in the art in view of the disclosure herein.

Upon placement of the implantable device 304 at the desired implantation site, the torque rod 340 is rotated in a direction that produces an axial proximal retraction. This allows radial enlargement of the radially outwardly biased implantable device 304 at the implantation site. Continued rotation of the torque rod 340 will cause the threaded core 342 to exit proximally through the threaded aperture 346. At that point, the deployment catheter 302 may be proximally retracted from the patient, leaving the implanted device 304 in place.

By modification of the decoupling mechanism to allow the core 342 to be decoupled from the torque rod 340, the rotatable core 342 may be left within the implantable device 304, as may be desired depending upon the intended deployment mechanism. For example, the distal end of the core 342 may be rotatably locked within the end cap 326, such as by including complimentary radially outwardly or inwardly extending flanges and grooves on the distal end of the core 342 and inside surface of the cavity 322. In this manner, proximal retraction of the core 342 by rotation thereof relative to the implantable device 304 will pull the end cap 326 in a proximal direction under positive force. This may be desirable as a supplement to or instead of a radially enlarging bias built into the implantable device 304.

In the embodiment illustrated in FIG. 19, or any other of the deployment and/or removal catheters described herein, the distal end of the tubular body 306 may be provided with a zone or point of enhanced lateral flexibility. This may be desirable in order allow the implant to seat in the optimal orientation within the left atrial appendage, and not be restrained by a lack of flexibility in the tubular body 306. This may be accomplished in any of a variety of ways, such as providing the distal most one or two or three centimeters or more of the tubular body 306 with a spring coil configuration. In this manner, the distal end of the tubular body 306 will be sufficiently flexible to allow the implant 304 to properly seat within the LAA. This distal flex zone on the tubular body 306 may be provided in any of a variety of ways, such as by cutting a spiral slot in the distal end of the tubular body 306 using laser cutting or other cutting techniques. The components within the tubular body 306 such as torque rod 340 may similarly be provided with a zone of enhanced flexibility in the distal region of the tubular body 306.

Figure 20:
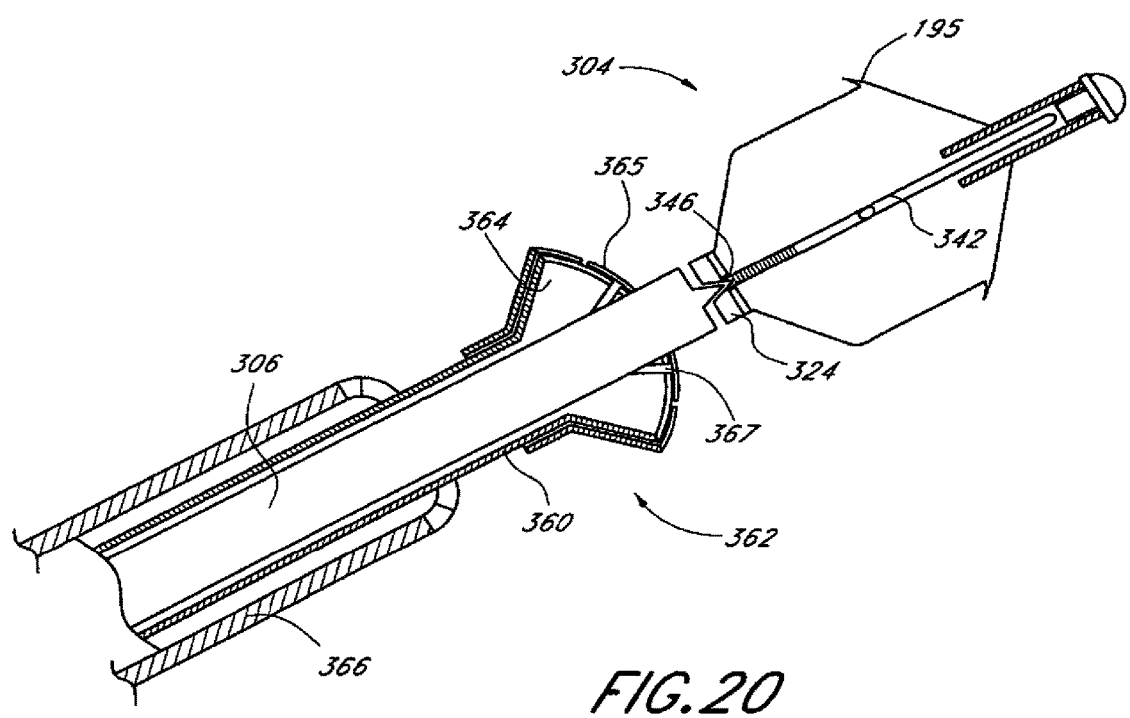
FIG. 20 is a schematic cross sectional view through the distal end of a retrieval catheter having a containment device removably connected thereto.

The implantable device 304 may also be retrieved and removed from the body in accordance with a further aspect of the present invention. One manner of retrieval and removal will be understood in connection with FIGS. 20 through 20C. Referring to FIG. 20, a previously implanted device 304 is illustrated as releasably coupled to the distal end of the tubular body 306, as has been previously discussed. Coupling may be accomplished by aligning the tubular body 306 with the proximal end 324 of the deployed implant 304, under fluoroscopic visualization, and distally advancing a rotatable core 342 through the threaded aperture 346. Threadable engagement between the rotatable core 342 and aperture 346 may thereafter be achieved, and distal advancement of core 342 will axially elongate and radially reduce the implant 304.

The tubular body 306 is axially movably positioned within an outer tubular delivery or retrieval catheter 360. Catheter 360 extends from a proximal end (not illustrated) to a distal end 362. The distal end 362 is preferably provided with a flared opening, such as by constructing a plurality of petals 364 for facilitating proximal retraction of the implant 304 as will become apparent. Petals 364 may be constructed in a variety of ways, such as by providing axially extending slits in the distal end 362 of the delivery catheter 360. In this manner, preferably at least about three, and generally at least about four or five or six petals or more will be provided on the distal end 362 of the delivery catheter 360. Petals 364 manufactured in this manner would reside in a first plane, transverse to the longitudinal axis of the delivery catheter 360, if each of such petals 364 were inclined at 90 degrees to the longitudinal axis of the delivery catheter 360.

In one application of the invention, a second layer of petals 365 are provided, which would lie in a second, adjacent plane if the petals 365 were inclined at 90 degrees to the longitudinal axis of the delivery catheter 360. Preferably, the second plane of petals 365 is rotationally offset from the first plane of petals 364, such that the second petals 365 cover the spaces 367 formed between each adjacent pair of petals 365. The use of two or more layers of staggered petals 364 and 365 has been found to be useful in retrieving implants 304, particularly when the implant 304 carries a plurality of tissue anchors 195.

The petals 364 and 365 may be manufactured from any of a variety of polymer materials useful in constructing medical device components such as the delivery catheter 360. This includes, for example, polyethylene, PET, PEEK, PEBAX, and others well known in the art. The second petals 365 may be constructed in any of a variety of ways. In one convenient construction, a section of tubing which concentrically fits over the delivery catheter 360 is provided with a plurality of axially extending slots in the same manner as discussed above. The tubing with a slotted distal end may be concentrically positioned on the catheter 360, and rotated such that the space between adjacent petals 365 is offset from the space between adjacent petals 364. The hub of the petals 365 may thereafter be bonded to the catheter 360, such as by heat shrinking, adhesives, or other bonding techniques known in the art.

Figure 20A:
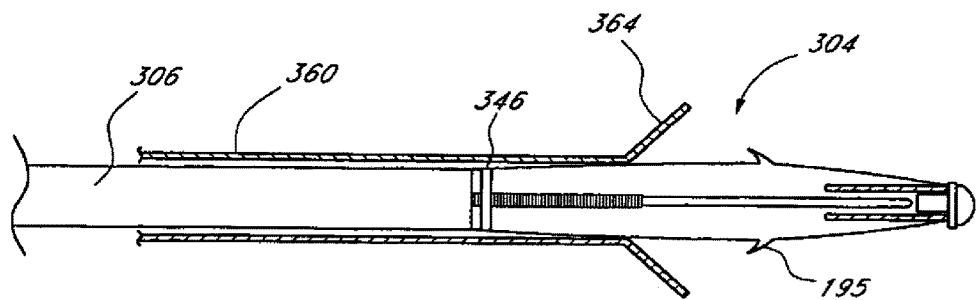
FIG. 20A is a schematic cross sectional view of the system illustrated in FIG. 20, with the containment device axially elongated and radially reduced.
Figure 20B:
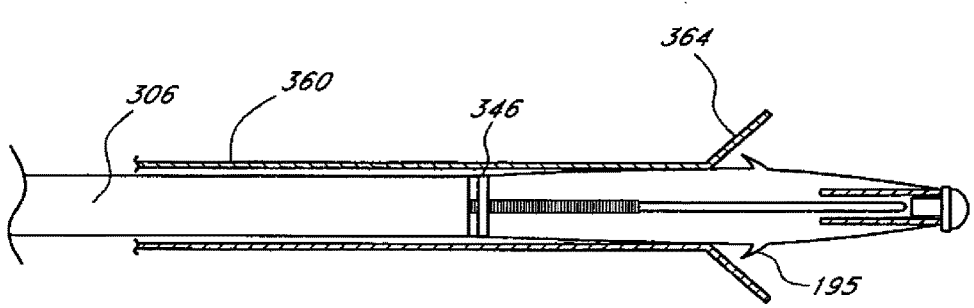
FIG. 20B is a cross sectional schematic view as in FIG. 20A, with the containment device drawn part way into the delivery catheter.
Figure 20C:
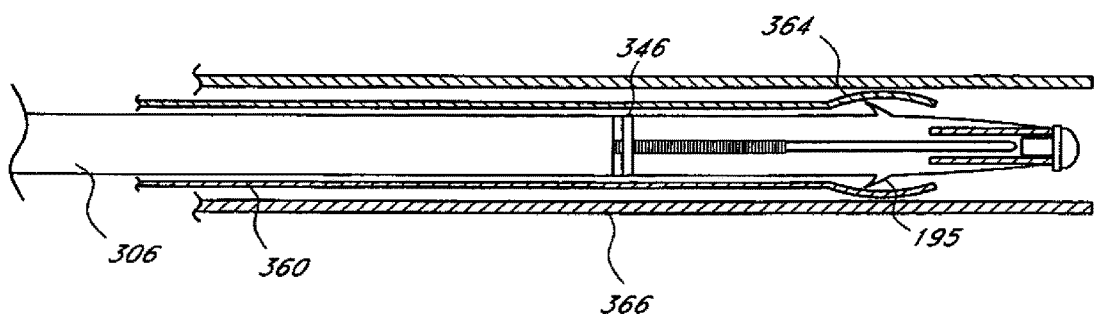
FIG. 20C is a schematic view as in FIG. 20B, with the containment device and delivery catheter drawn into a delivery sheath.

The removal sequence will be further understood by reference to FIGS. 20a through 20c. Referring to FIG. 20a, the radially reduced implant 304 is proximally retracted part way into the delivery catheter 360. This can be accomplished by proximally retracting the tubular body 306 and/or distally advancing the catheter 360. As illustrated in FIG. 20b, the tubular body 306 having the implant 304 attached thereto is proximally retracted a sufficient distance to position the tissue anchors 195 within the petals 364. The entire assembly of the tubular body 306, within the delivery catheter 360 may then be proximally retracted within the transseptal sheath 366 (e.g., delivery sheath) or other tubular body as illustrated in FIG. 20c. The collapsed petals 364 allow this to occur while preventing engagement of the tissue anchors 195 with the distal end of the transseptal sheath 366 or body tissue. The entire assembly having the implantable device 304 contained therein may thereafter be proximally withdrawn from or repositioned within the patient.

Figure 21:
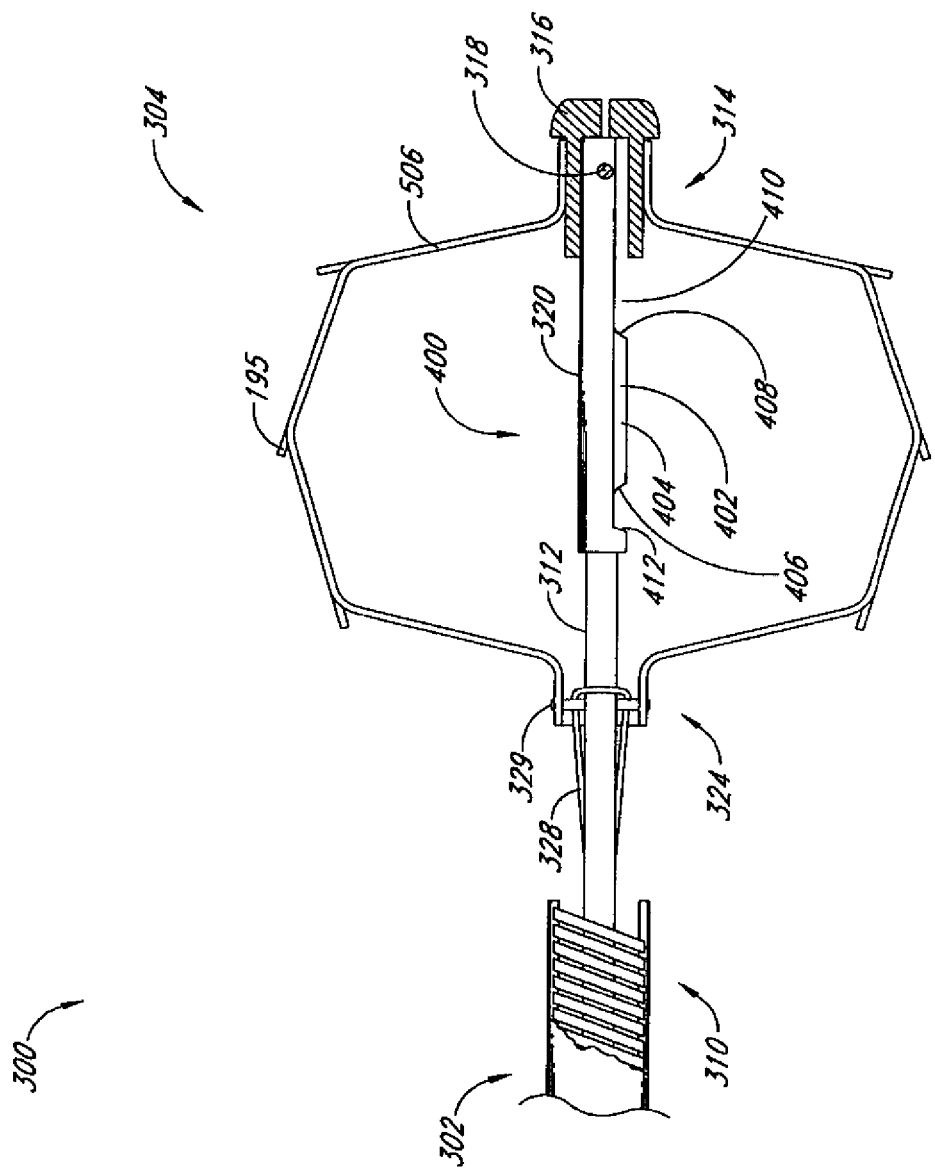
FIG. 21 is a schematic cross sectional view of a distal portion of an adjustable implant deployment system.
Figure 21C:
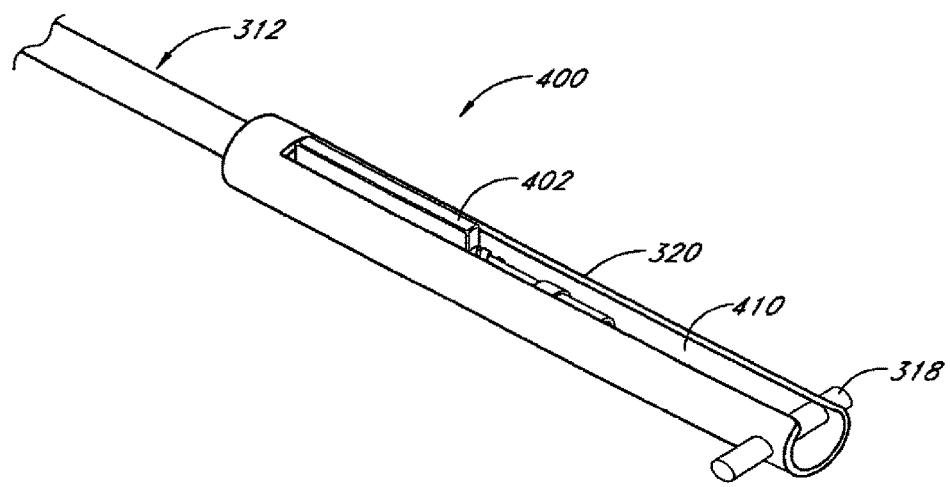
FIG. 21C is a perspective view of the slider assembly of FIG. 21 shown coupled to an axially moveable core.
Figure 21D:
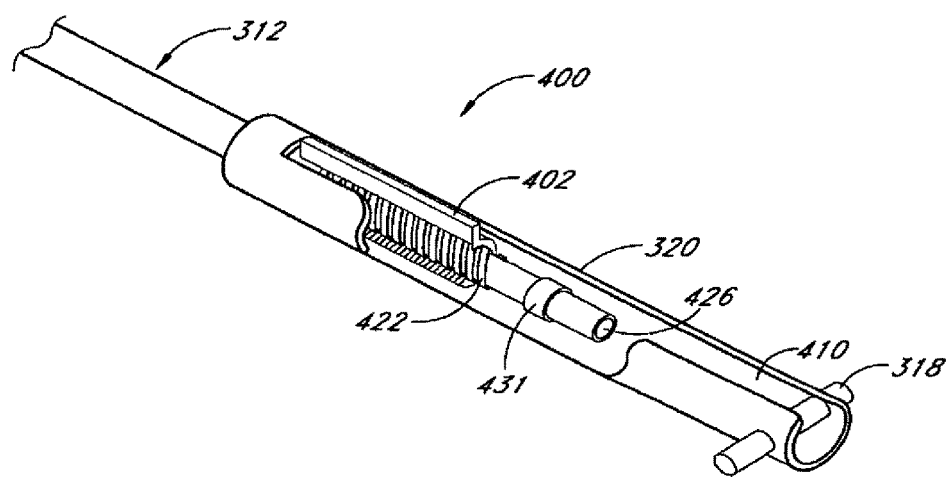
FIG. 21D is a partial cut away view of the slider assembly of FIG. 21C showing the position of the axially moveable core with respect to the slider nut of the slider assembly.
Figure 21E:
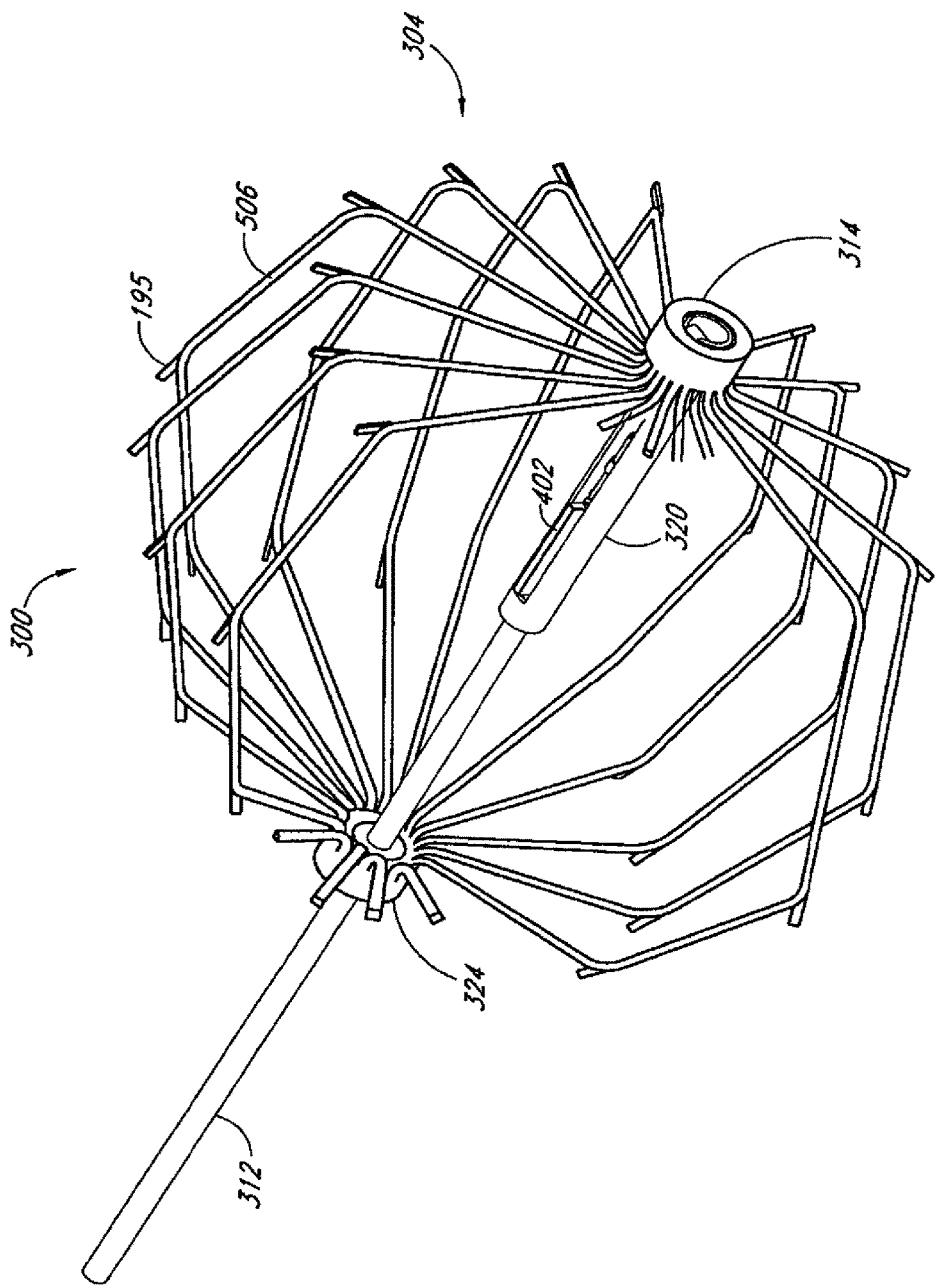
FIG. 21E is a partial cut away view of the slider assembly of FIG. 21 shown coupled to the frame of a detachable implant.

In FIGS. 21-21E there is provided another embodiment of an implant and delivery system. Adjustable implant deployment system 300 comprises catheter 302 and detachable implant 304 having a frame 506 and anchors or barbs 195, as discussed in greater detail above with respect to FIG. 17 and other figures. As illustrated in FIG. 21, the deployment system 300 also includes a slider assembly 400. In the illustrated embodiment, slider assembly 400 includes a guide tube 320 extending proximally from the distal end or distal hub 314 of the implant, and a slider nut 402 slidably received in a channel 430 of the guide tube 320. Slider nut 402 preferably includes a flange 404 operable to travel within a longitudinal slot 410 that extends at least partially along the length of guide tube 320. The flange 404 of the slider nut 402 has a proximal surface 406 and a distal surface 408. Slot 410 has a proximal surface 412, and in one embodiment, extends through the distal end of the guide tube 320. Slot 410 may have a generally rectangular shape.

In the embodiment shown in FIG. 21, proximal movement of the flange 404 within the slot 410, as well as proximal movement of the slider nut 402 within the guide tube 320, is limited by interference between the proximal surfaces 406, 412, of flange 404 and guide tube 320, respectively, as slider nut 402 is moved in the proximal direction. As shown in FIGS. 21A, 21C and 21D, distal movement of the flange 404 within the slot 410, as well as distal movement of the slider nut 402 within the guide tube 320, is limited by interference between the axially moveable core 312 and the cross pin 318, as described in greater detail with reference to FIG. 21A below. In addition, flange 404 prevents slider nut 402 from rotating within guide tube 320 due to the interference between flange 404 and the side walls of the slot 410.

In one embodiment, the slot 410 of the guide tube 320 is laser-cut, and has a length in the range between about 3 mm and 35 mm, and a width in the range between about 0.5 mm and 2 mm. In one embodiment, the length of the guide tube 320 slot 410 is in the range between about 0.4 in and about 0.826 in. In one embodiment, the width of the guide tube 320 slot 410 is in the range between about 0.02 in and about 0.04 in. In one embodiment, the slider nut 402 is a keyed polymer extrusion, and is sized so that it fits and slides at least partially within the guide tube 320. Such material is advantageous in that it provides a reduced friction interface between the slider nut 402 and the guide tube 320. In other embodiments, the slider nut 402 is made from plastic, metal, or ceramic. In another embodiment, the slider nut 402 is made from PEBAX, polyethylene, polyurethane, nickel titanium, or stainless steel. Flange 404 may be integrally formed with the slider nut 402, or may be attached to it. In one embodiment, flange 404 is made from plastic, and is sized so that it fits and slides within the slot 410 of the guide tube 320. The exact length of the flange 404 is selected based upon the dimensions of the slot 410, and will vary based upon the clinical parameters of the particular treatment.

Several views of one embodiment of the adjustable implant deployment system 300 of FIG. 21 are shown in FIGS. 21A-21E. FIG. 21A illustrates the distal end 344 of an axially moveable core 312 similar to that described above, releasably coupled to a slider assembly 400. Slider assembly 400 includes guide tube 320 and slider nut 402, as described above. Slider nut 402 includes a flange 404 as described above and a mating surface 420 for receiving the distal end 344 of axially moveable core 312. In one embodiment, mating surface 420 of nut 402 is an internally threaded surface. Mating surface 420 of nut 402 engages mating surface 422 of axially moveable core 312 to provide axial coupling between the movement of the axially moveable core 312 and the slider nut 402. In the illustrated embodiment, mating surface 422 of axially moveable core 312 is an externally threaded surface on a distal section of the axially moveable core which terminates proximal to the very distal tip of the axially moveable core 312.

In one embodiment, the axially moveable core 312 includes a proximal shaft 576, a flexible core section 564, and a distal shaft 578 as described in greater detail below with reference to FIG. 37. The distal shaft 578 includes a mating surface 584 (as shown on FIG. 37), which corresponds to the mating surface 422 of the axially moveable core 312 as shown on FIG. 21A. The mating surface 422 of axially moveable core 312 preferably is a threaded surface to facilitate releasable attachment to the mating surface 420 of the slider nut 402. In one embodiment, the mating surface 422 provides self-tapping functionality to the axially moveable core 312. The mating surface 422 of the axially moveable core 312 includes threads, and is self-tapping as it is inserted into the slider nut 402 of the slider assembly 400. In one embodiment, the slider nut 402 contains a central lumen extending axially therethrough. In one embodiment, the mating surface 420 of the slider nut 402 does not contain threads, but is tapped (e.g., mating threads are created), as the axially moveable core 312 is inserted into, and rotated with respect to the slider nut 402.

In one embodiment, the axially moveable core 312 preferably is attached to the slider nut 402 by rotating the axially moveable core 312 such that the threads of the mating surface 422 of axially moveable core 312 engage threads of the mating surface 420 of nut 402. Similarly, in one embodiment, axially moveable core 312 is detached or decoupled from the slider nut 402 of the slider assembly 400 by rotating the axially moveable core 312 in the opposite direction. In one embodiment, as the axially moveable core 312 is rotated in the detachment direction, the threads of the mating surface 422 of axially moveable core 312 disengage the threads of the mating surface 420 of nut 402, thereby releasing the axially moveable core 312 from the slider nut 402, slider assembly 400, and implant 304. Additional description of the axially moveable core 312 and contemplated alternative embodiments are provided below, including the illustration and discussion related to FIG. 37.

In the embodiment of FIGS. 21-21E, there is illustrated the axially moveable core 312 releasably coupled to the slider nut 402 of the slider assembly 400 of an implant 304. In the illustrated embodiment, the mating surface 422 of axially moveable core 312 is coupled with the mating surface 420 of nut 402 such that the distal end surface 429 of the axially moveable core 312 and a marker 431 reside distal the slider nut 402 of the slider assembly 400. In one embodiment, the axially moveable core 312 is coupled to the slider nut 402 such that the marker 431 resides approximately 1 to 3 mm distal the distal surface 418 of slider nut 402. In other embodiments, the axially moveable core 312 is coupled to the slider nut 402 of the slider assembly 400 such that the distal surface 429 of the axially moveable core 312 and/or the marker 431 reside within slider nut 402. Examples of such embodiments are provided in greater detail below with reference to FIGS. 22A, 23, and 26.

In one embodiment, axially moveable core 312 also includes a lumen 426. The lumen 426 preferably allows visualization dye to flow through the lumen 426 of the axially moveable core 312, through the lumen 428 of the implant plug 316, and into the left atrial appendage. Such usage of visualization dye is useful for clinical diagnosis and testing of the position of the implant 304 within the left atrial appendage or other body opening, as described in greater detail below.

The marker 431 as shown in FIGS. 21A, 21C and 21D advantageously assists in locating the position of the distal end 344 of the axially moveable core 312. In one embodiment, marker 431 comprises a radiopaque band press fit onto the distal end 344 of the axially moveable core 312. Marker 431 preferably is made from a material readily identified after insertion into a patient's body by using visualization techniques that are well known to those of skill in the art. In one embodiment, the marker 431 is made from gold, or tungsten, or any such suitable material, as is well known to those of skill in the art. In another embodiment, marker 431 is welded, soldered, or glued onto the distal end 344 of the axially moveable core 312. In one embodiment, marker 431 is an annular band and surrounds the circumference of the axially moveable core 312. In other embodiments, the marker 431 does surround the circumference of the axially moveable core 312. In other embodiments, marker 431 includes evenly or unevenly spaced marker segments. In one embodiment, the use of marker segments is useful to discern the radial orientation of the implant 304 within the body.

In the embodiment of FIG. 21A, with axially moveable core 312 threadingly engaged with slider nut 402, as axially moveable core 312 is moved distally, distal surface 429 of axially moveable core 312 presses against cross pin 318 to place or maintain implant 304 in a reduced diameter configuration (such as in combination with pulling proximally on pull wire 328, as discussed above). As tension on pull wire 328 is reduced, implant 304 assumes its expanded diameter configuration by bending under its own bias. Alternatively, in another embodiment, axially moveable core 312 is moved proximally, thereby relieving pressure on cross pin 318, and allowing implant 304 to assume its expanded diameter configuration. Expansion and reduction of implant 304 diameter is described in greater detail above with reference to FIG. 17, and further below.

Once implant 304 of FIG. 21A assumes the expanded configuration, the axially moveable core 312 and the slider nut 402 may be moved proximally until the proximal surface 406 of flange 404 interferes with the proximal surface 412 of slot 410, without substantially affecting the shape or position of the implant 304. Similarly, once the implant 304 assumes the expanded configuration, the axially moveable core 312 and slider nut 402 may be moved distally back until the distal surface 429 of the axially moveable core 312 interferes with the cross pin 318, or implant plug 316, without substantially affecting the shape or position of the implant 304.

Such controllable axial decoupling between the movement of the axially moveable core 312 and the implant 304 is useful during delivery and expansion of the implant 304. In addition, controllable axial decoupling is useful for testing the seal between the implant 304 and the left atrial appendage once the implant 304 has been delivered, but before releasing the implant 304 from the catheter 302.

For example, it is clinically advantageous to provide axial decoupling between the axially moveable core 312 and the implant 304. Axial decoupling assures that movement of the axially moveable core 312, as well as other components of the adjustable implant deployment system 300 that are coupled to the axially moveable core 312 (for example, but not limited to the deployment handle 538 and the catheter 302, described further below), do not substantially affect the shape or position of the implant 304. Such axial decoupling prevents inadvertent movement of the axially moveable core 312 or deployment handle 538 from affecting the shape or position of implant 304. For example, in one embodiment, if the user inadvertently pulls or pushes the axially moveable core 312 or the deployment handle, the position of the implant 304 within the left atrial appendage preferably will not be substantially affected. In addition, axial decoupling also preferably prevents the motion of a beating heart from translating into movement of the axially moveable core 312, the catheter 302, and the components coupled to the axially moveable core 312 and catheter 302, including the deployment handle. By decoupling the implant 304 from the axially moveable core 312 and other components coupled to the axially moveable core 312, the risk of accidentally dislodging the implant 304 from the left atrial appendage during testing is reduced.

Figure 22:
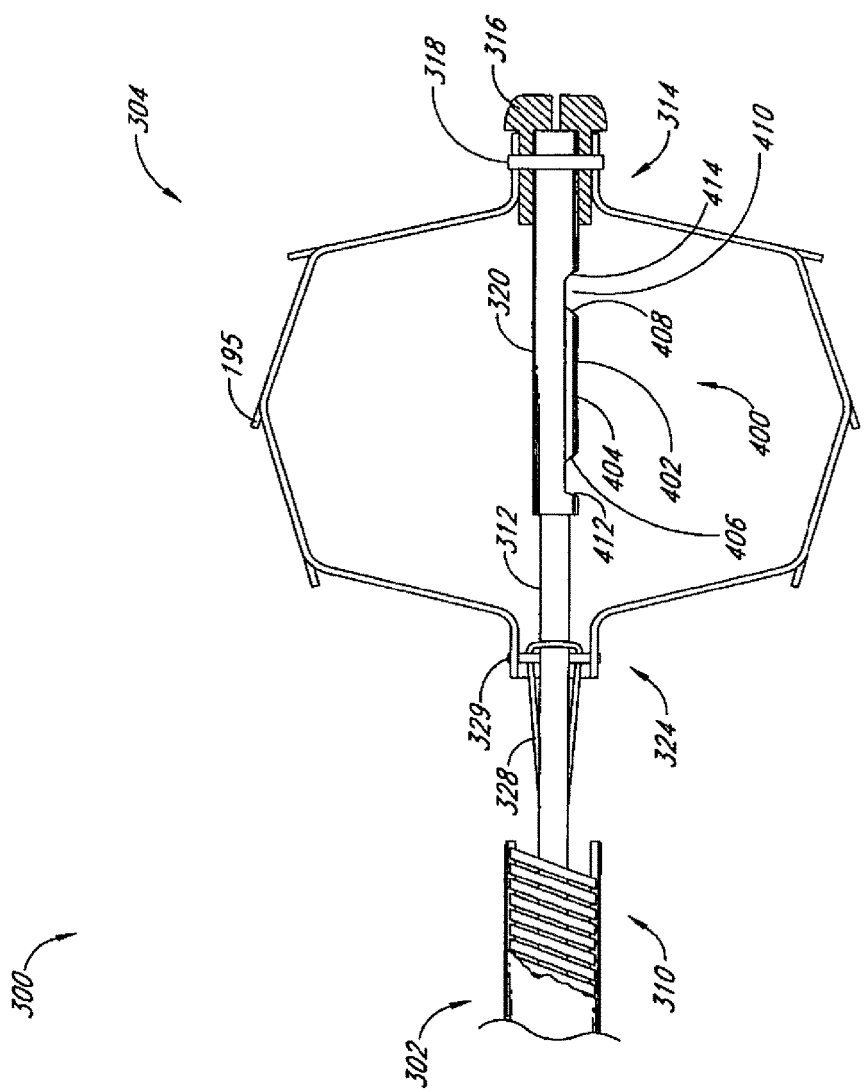
FIG. 22 is a schematic cross sectional view of a distal portion of another embodiment of an adjustable implant deployment system.

There is illustrated in FIG. 22 another adjustable implant deployment system 300 built in accordance with another embodiment of the present invention. The embodiment illustrated in FIG. 22 is similar to that illustrated in FIG. 21. Adjustable implant deployment system 300 comprises catheter 302 and detachable implant 304 as discussed in greater detail above with respect to FIG. 17. The system 300 also includes a slider assembly 400 having a guide tube 320 and slider nut 402 slidably received therein. Slider nut 402 preferably includes a flange 404 operable to travel within the longitudinal slot 410 of the guide tube 320. The flange 404 of the slider nut 402 has a proximal surface 406 and a distal surface 408. Slot 410 has a proximal surface 412 and distal surface 414, and does not extend through the distal end of the guide tube 320. Slot 410 in one embodiment has a generally rectangular shape.

The slider assembly 400 of FIG. 22 functions in a similar manner to that illustrated and described with reference to FIGS. 21-21E. However, as shown in FIG. 22A, once the implant 304 assumes the expanded configuration, the axially moveable core 312 and slider nut 402 may be moved distally until the distal surface 408 of flange 404 interferes with the distal surface 414 of slot 410 and/or the distal surface of slider nut 402 interferes with cross pin 318, without substantially affecting the shape or position of the implant 304.

In one embodiment, the axially moveable core 312 of FIG. 22A is similar to that of FIG. 21A, except for the location of mating surface 422. In the embodiment illustrated in FIG. 22A, the mating surface 422 of axially moveable core 312 extends to the distal surface 429 of axially moveable core 312. In such configuration, the mating surface 422 of axially moveable core 312 preferably is contained within the slider nut 402 of the slider assembly 400, as illustrated in FIG. 22A. The marker 431 (not shown in FIG. 22A) of the axially moveable core 312 preferably is attached to the axially moveable core 312 such that it does not interfere with the coupling of the mating surface 420 of nut 402 and mating surface 422 of axially moveable core 312. For example, in one embodiment, marker 431 is pressed, welded, soldered, glued or plated onto the lumen 426 of the axially moveable core 312, the distal surface 429 of axially moveable core 312, or circumferentially around or partially circumferentially around the axially moveable core 312 such that interference between mating surfaces 420, 422 does not occur. In addition, in the embodiment of FIG. 22A, the distal end 344 of axially moveable core 312 preferably is positioned within the slider nut 402 of the slider assembly 400, and does not extend past the distal surface 418 of slider nut 402.

In the embodiment illustrated in FIG. 22A, slider nut 402 includes a lumen 424 extending distally of core 312 that allows visualization dye to flow from the lumen 426 of axially moveable core 312 through to the lumen 428 of the implant plug 316 and into the left atrial appendage. Such usage of visualization dye is described in greater detail below.

An illustration of an alternative implementation of a slider assembly is provided in FIG. 23. FIG. 23 illustrates the distal end 344 of axially moveable core 312 coupled to a slider assembly 400 similar to that described above. In FIG. 23, slider assembly 400 includes a guide tube 320 and a slider nut 402. Guide tube 320 includes a channel 430 in which slider nut 402 travels as axially moveable core 312 is moved proximally or distally. Proximal movement of the slider nut 402 is limited by interference between proximal surface 416 of slider nut 402 and proximal ridge 432 of guide tube 320. Distal movement of the slider nut 402 is limited by interference between distal surface 418 of slider nut 402 and the distal ridge 434 of guide tube 320. Alternatively, distal movement of the slider nut 402 can be limited by interference between the distal surface 418 of slider nut 402 and the cross pin 318, or the implant plug 316, as shown in greater detail with reference to FIG. 22.

Figure 24:
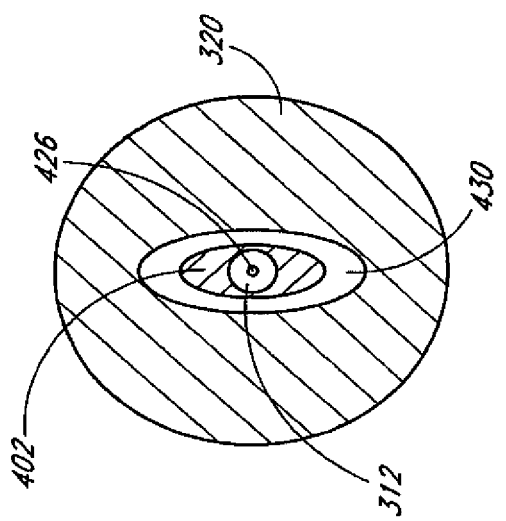
FIGS. 24 and 25 are alternative cross sectional views taken along cut line A-A of FIG. 23.
Figure 25:
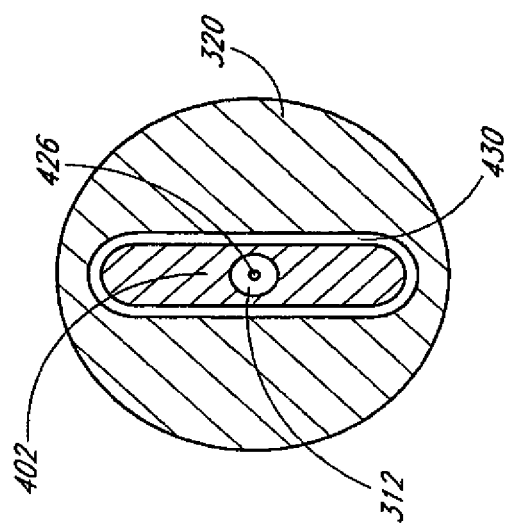

To prevent rotation of slider nut 402 within the guide tube 320, the cross-sectional shape of the channel 430 and slider nut 402 may have a non-circular shape. Examples of non-circular cross-sectional shapes of slider nut 402 are illustrated with reference to FIG. 24 and FIG. 25. FIG. 24 illustrates one implementation in which the slider nut 402 and channel 430 have an elliptical cross-sectional shape. FIG. 25 illustrates another implementation in which the slider nut 402 and the channel 430 have a rounded-rectangular cross-sectional shape. It is well understood by those skilled in the art that the slider nut 402 and channel 430 may have any non-circular shape so as to prevent rotation of slider nut 402 within the guide tube 320.

Figure 26:
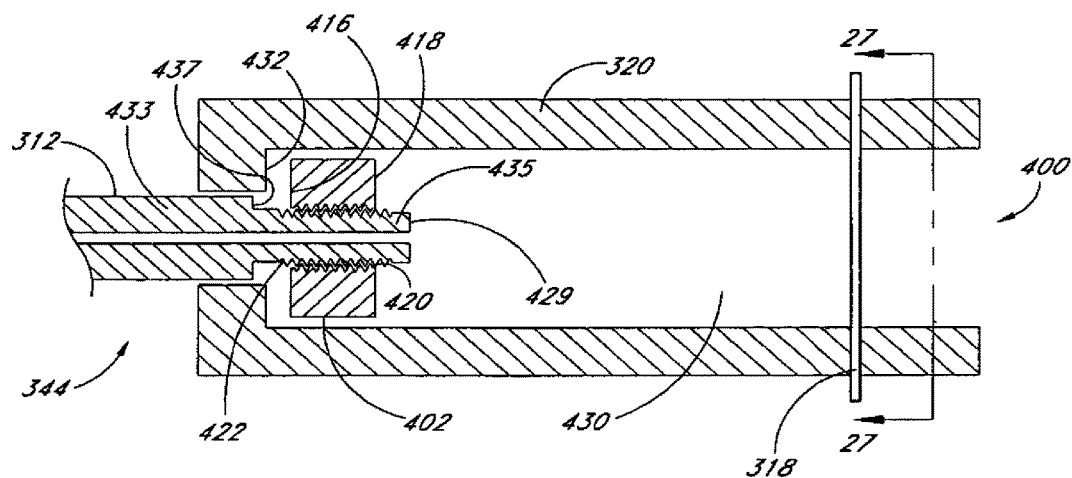
FIG. 26 is a schematic cross sectional view of another slider assembly for use with the adjustable implant deployment system of FIG. 21.

Another implementation of one embodiment of the present invention is provided with reference to FIG. 26. FIG. 26 illustrates the distal end 344 of axially moveable core 312 removably coupled to a slider assembly 400. As shown in FIG. 26, proximal movement of slider nut 402 is limited by interference between proximal surface 416 of slider nut 402 and proximal ridge 432 of guide tube 320. Distal movement of slider nut 402 is limited by interference between distal surface 429 of axially moveable core 312 and cross pin 318. The distal end 344 of the axially moveable core 312 is shown having a first diameter 433, a second diameter 435, and a step 437 therebetween. In other embodiments, the distal end 344 of the axially moveable core 312 does not include such first diameter 433, second diameter 435, and step 437. In one embodiment, the axially moveable core 312 is screwed into the slider nut 402 of the slider assembly 400 until the proximal surface 416 of slider nut 402 interferes with the step 437 of the axially moveable core 312. In another embodiment, the axially moveable core 312 is advanced distally into the slider nut 402 of the slider assembly 400 as far as the mating surface 420 of nut 402 and mating surface 422 of axially moveable core 312 permit. Axial rotation of slider nut 402 with respect to the guide tube 320 may be limited by providing slider nut 402 with a non-circular cross-sectional shape, as described in greater detail above. An example of slider nut 402 having a non-circular cross-sectional shape is illustrated in FIG. 27. FIG. 27 shows the sectional view along cut line 27-27 of FIG. 26.

In another embodiment described with reference to FIG. 26A, a slider assembly 400 does not include a slider nut 402. Instead, the distal end 600 of an axially moveable core 312 includes an externally threaded, enlarged diameter, distal portion 602, and the proximal end 604 of a guide tube 320 includes an internally threaded, reduced diameter, proximal portion 606. The axially moveable core 312 is coupled to the guide tube 320 of the implant 304 by screwing the externally threaded, enlarged diameter, distal portion 602 of the axially moveable core 312 into the internally threaded, reduced diameter, proximal portion 606 of the guide tube 320. Once coupled, the implant 304 is delivered to the desired deployment site within the patient as described in further detail herein. The axially moveable core 312 is then further manipulated (e.g., rotated in a clockwise direction), until the externally threaded, enlarged diameter, distal portion 602 of the axially moveable core 312 enters the guide tube 320 of the implant 304, and becomes decoupled from the internally threaded, reduced diameter, proximal portion 606 of the guide tube 320, as shown in FIG. 26A.

Thereafter, proximal movement of the axially moveable core 312 with respect to the implant 304 is limited by interference between a proximal surface 608 of the external threads of the enlarged diameter, distal portion 602 of the axially moveable core 312, and a distal surface 610 of the internal threads of the reduced diameter, proximal portion 606 of the guide tube 320. Distal movement of the axially moveable core 312 with respect to the implant 304 is limited by interference between a distal surface 612 of the external threads of the enlarged diameter, distal portion 602 of the axially moveable core 312, and a cross pin 318, as described in greater detail herein. Alternatively, distal movement of the axially moveable core 312 with respect to the implant 304 can be limited by interference between the distal surface 429 of axially moveable core 312 and the cross pin 318, as described in greater detail herein.

To remove the axially moveable core 312, the axially moveable core 312 is moved proximally with respect to the implant 304 and manipulated (e.g., rotated counter-clockwise), until the external threads of the enlarged diameter, distal portion 602 of the axially moveable core 312 engage the internal threads of the reduced diameter, proximal portion 606 of the guide tube 320. The axially moveable core 312 is then further manipulated (e.g., rotated counter-clockwise), until the external threads of the enlarged diameter, distal portion 602 of the axially moveable core 312 disengage the internal threads of the reduced diameter, proximal portion 606 of the guide tube 320 such that the axially moveable core 312 may thereafter be removed from the patient while leaving the implant 304 in place.

Figure 26A:
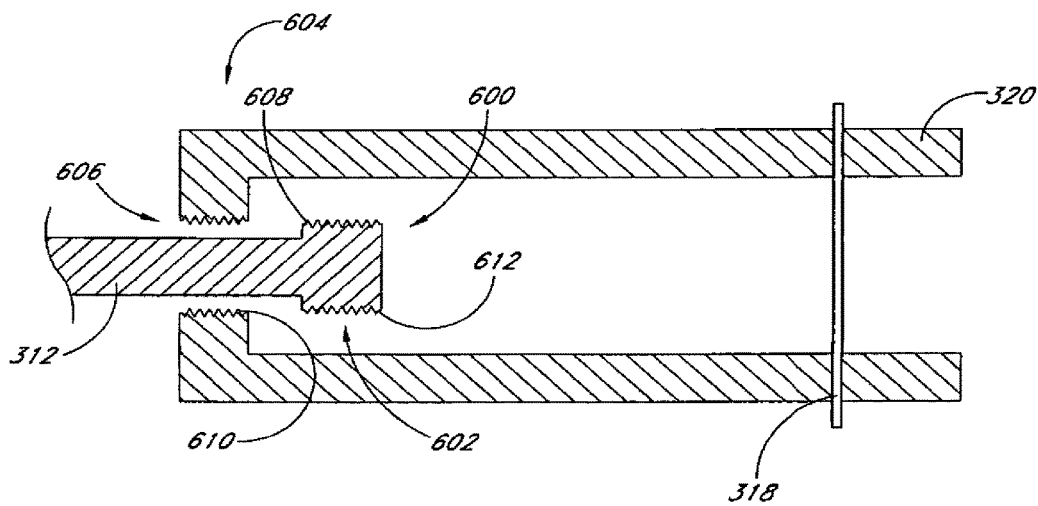
FIG. 26A is a schematic cross sectional view of another slider assembly for use with the adjustable implant deployment system of FIG. 21.

In the embodiment of FIG. 26A described above, transverse movement of at least a portion of the axially moveable core 312 with respect to the guide tube 320 and the implant 304 is decoupled over a limited range. As illustrated, transverse movement is permitted by the outside diameter of the axially moveable core 312 being substantially smaller than the inside diameter of the proximal portion of the guide tube 320. This permits the core 312 to move transversely within the space defined by the proximal portion of the guide tube. In other embodiments, transverse movement is permitted by controlling the relative dimensions of the inside diameter of the guide tube 320, the inside diameter of the proximal portion of the guide tube 320, the outside diameter of the axially moveable core 312, the outside diameter of the slider nut 402, or a combination of any of the above, to provide space between corresponding parts of the device. It will be appreciated by those of skill in the art that transverse movement may be provided with any of the embodiments described herein, including those that incorporate a slider nut 402 as part of the slider assembly 400. In one embodiment, as at least a portion of the axially moveable core 312 is moved in a direction transverse to the guide tube 320, the axially moveable core 312 can also be positioned at an angle with respect to the longitudinal axis of the guide tube 320 and implant 304.

FIG. 28 illustrates another implementation of a slider assembly 400. The slider assembly 400 provides quick-disconnect functionality, and the ability to release the axially moveable core 312 from the guide tube 320 without using rotational forces. Such configuration is advantageous in that rotational forces applied to the axially moveable core 312 to unscrew it from the guide tube 320 can, in some clinical situations, cause the implant 304 to rotate within or dislodge from the left atrial appendage. By using quick-disconnect functionality, such as that illustrated in the embodiment of FIG. 28, the operator may decouple the axially moveable core 312 from the guide tube 320 of the slider assembly 400 by applying axial force instead of rotational force. An axial force may be particularly advantageous because in certain embodiments, the anchors 195 of the implant may provide greater resistance to axial movement than to rotational movement, and thus be better able to withstand axial decoupling of the axially moveable core 312 from the slider assembly 400 than rotation decoupling.

In the illustrated embodiment of FIG. 28, slider assembly 400 includes a guide tube 320, shown coupled to an axially moveable core 312. Guide tube 320 includes a slot 410, as described in greater detail above with reference to FIG. 21. Axially moveable core 312 is preferably hollow and includes a bending plug 436 near its distal end, a port 440 provided in the core 312 adjacent plug 436, with a retractable lock 438 extending through the lumen of the core 312. After axially moveable core 312 is inserted into the guide tube 320, retractable lock 438 is advanced distally relative to the core 312 until it is guided by bending plug 436 through the port 440 of axially moveable core 312. When properly positioned, a distal tip 442 of retractable lock 438 extends into the slot 410 of the guide tube 320. The distal tip 442 of retractable lock 438 limits axial movement of the axially moveable core 312 relative to the guide tube 320 by interference between the distal tip 442 of retractable lock 438 and the proximal and distal surfaces 412, 414 of slot 410. Retractable lock 438 is made from a material or materials flexible enough to bend as provided by bending plug 436, yet stiff enough to limit the motion of the axially moveable core 312 by interfering with proximal and distal surfaces 412, 414 of slot 410. In one embodiment, retractable lock 438 includes a spiral cut, transverse slots, or changes in material or thickness to control flexibility. In one embodiment, the distal tip 442 of retractable lock 438 comprises a material that is stiffer, or less flexible than the retractable lock 438.

In one embodiment, the retractable lock 438 is made from a flexible wire, such as a nickel titanium or stainless steel. Alternatively, retractable lock 438 is made from metal hypotube, plastic, or other biocompatible material. In one embodiment, bending plug 436 is made from metal, such as nickel titanium or stainless steel. Alternatively, bending plug 436 is made from plastic, or other biocompatible material.

Figure 29:
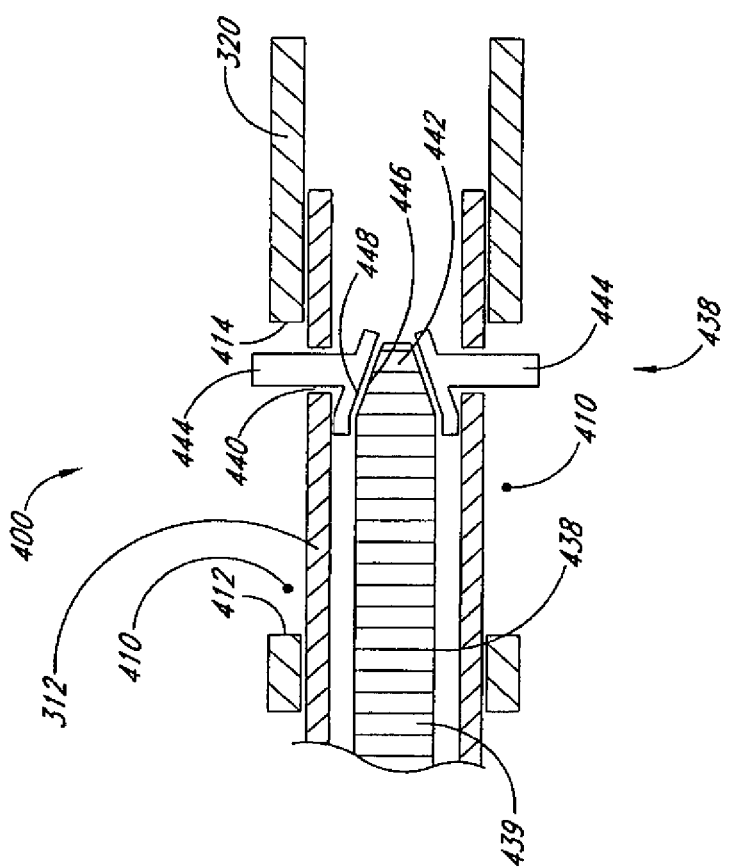
FIG. 29 is a schematic cross sectional view of another slider assembly incorporating quick-disconnect functionality, constructed in accordance with another embodiment of the present invention.
Figure 29A:
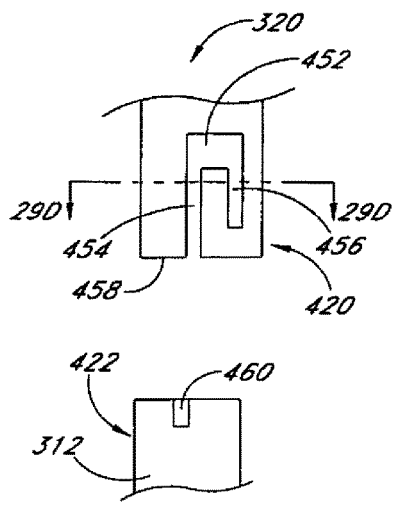
FIG. 29A is a side elevational view of a bayonet mount coupling the guide tube of the slider assembly of an implant to an axial moveable core, in accordance with one embodiment of the present invention.

An alternative embodiment of a slider assembly 400 is shown in FIG. 29. The slider assembly 400 of FIG. 29 also provides quick-disconnect functionality for release of axially moveable core 312 from guide tube 320 by using non-rotational forces. As illustrated, slider assembly 400 includes a guide tube 320, which comprises at least one slot 410. Two opposing slots 410 are shown in the embodiment of FIG. 29. Axially moveable core 312 is coupled to guide tube 320 by quick-disconnect functionality.

Axially moveable core 312 in this embodiment includes a retractable lock 438 in the form of an elongate key 439 extending through the lumen of the core 312, and two opposing ports 440 in axially moveable core 312 through which two tabs 444 extend. The distal tip 442 of the key 439 includes a contact surface 446 operable to engage contact surfaces 448 of the tabs 444. The key 439 is moveable relative to the axially moveable core 312, and can be moved distally such that contact surface 446 engages contact surfaces 448 of tabs 444, translating into radial movement of tabs 444. Radial movement of tabs 444 causes them to project into slots 410 of the guide tube 320 by bending radially outwardly, and extending in a substantially radial direction. In one embodiment, the key 439 is secured in place relative to the axially moveable core 312, so that the tabs 444 remain projected into the slots 410 of the guide tube 320. With the tabs 444 secured in place, axial movement of axially moveable core 312 preferably is limited by interference between the tabs 444 and the proximal and distal surfaces 412, 414 of guide tube 320.

In one embodiment, the key 439 is made from an elongate wire, rod, or tube flexible enough for delivery through the adjustable implant deployment system 300 described above, and strong enough to apply enough force to tabs 444 to achieve the functionality described above. In one embodiment, the key 439 is made from stainless steel. The key 439 preferably is locked in place relative to the axially moveable core 312 by using a control, such as a thumbswitch or other such device as is well known to those of skill in the art. For example, in one embodiment, the axially moveable core 312 is secured to the proximal portion of a deployment handle (not shown) such that the position of the axially moveable core 312 is fixed with respect to the deployment handle. A key 439 preferably is inserted inside of the axially moveable core 312 such that it may slide axially within the axially moveable core 312. The proximal portion of the key 439 preferably is coupled to a control, such as, for example, a thumbswitch. The thumbswitch preferably is provided such that it may slide axially with respect to the deployment handle (and therefore with respect to the axially moveable core 312) over a predetermined range. By coupling the thumbswitch to the proximal portion of the key 439, axial movement of the key 439 with respect to the axially moveable core 312 is achieved over the predetermined range. In addition, by locking the thumbswitch in place (by using mechanisms well known to those of skill in the art, such as release buttons, tabs, or their equivalents), the key 439 may be locked in place with respect to the axially moveable core 312. Alternatively, switches, levers, buttons, dials, and similar devices well known to those of skill in the art may be used instead of a thumbswitch as the control for the retractable lock 438.

To decouple axially moveable core 312 from the guide tube 320, retractable lock 438 is released by moving key 439 proximally relative to axially moveable core 312, thereby removing radial forces from contact surfaces 448 of tabs 444. In one embodiment, tabs 444 are biased to bend inward upon the removal of the radial forces from their contact surfaces 448. For example, tabs 444 preferably are constructed from a spring material, or a shape memory metal, such as, for example, nickel titanium. Alternatively, in another embodiment, key 439 is moved distally to decouple axially moveable core 312 from the guide tube 320. For example, in one embodiment, key 439 includes a cutout, notch, or slot along at least a portion of its distal end. In one embodiment, as the key 439 is moved distally, the cutout, notch, or slot is moved such that it engages the tabs 444, allowing them to flex inwardly preferably under their own bias. In another embodiment, tabs 444 are biased to bend outward upon removal of a radial force from a contact surface 448, and bend inward upon application of a radial force to contact surface 448. In such embodiment, the key 439 preferably is advanced distally to apply force on a contact surface 448 such that tabs 444 are directed inward. In one embodiment, the key 439 is advanced proximally to apply force on a contact surface 448 such that tabs 444 are directed inward.

Alternative mechanisms for coupling the axially moveable core 312 to the slider assembly 400 may be used in addition to or instead of those described above. In one embodiment, the mating surface 420 of nut 402 and mating surface 422 of axially moveable core 312 may include at least one slot and at least one pin, respectively, such that axially moveable core 312 couples with the slider nut 402 by a bayonet mount. In one such embodiment, axially moveable core 312 is proximally advanced until the at least one slot of its mating surface 422 receives the at least one pin of the mating surface 420 of the nut 402. Axially moveable core 312 is subsequently rotated to lock the axially moveable core 312 with respect to the slider nut 402. Axially moveable core 312 may be decoupled from slider nut 402 by rotating it in the opposite direction.

Figure 29B:
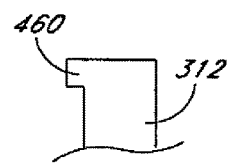
FIG. 29B is a side elevational view of the axially moveable core of FIG. 29A.

Referring to FIGS. 29A-G, in one embodiment, the axially moveable core 312 is coupled to the guide tube 320 of the slider assembly 400 with a bayonet mount 450. In one embodiment, the bayonet mount 450 includes a guide tube 320, which includes an un-threaded channel 430, and a maze-type slot 452. In one embodiment, the maze-type slot 452 includes at least one entry portion 454 extending in an axial direction, and at least one keyed portion 456 extending at least partially in a non-axial direction. In one embodiment, the maze-type slot 452 extends from the proximal edge 458 of the guide tube 320 in the distal direction, then extends in a direction substantially transverse the axis of the guide tube 320, and then extends axially, either in the proximal or distal direction, or both, such as shown for example, in FIGS. 29E and 29F. The mating surface 422 of the axially moveable core 312 includes a flange 460, pin, or equivalent structure, which engages the maze-type slot 452 of the guide tube 320. An example of one such flange 460 is illustrated in FIG. 29B. By manipulating the flange 460 of the axially moveable core 312 with respect to the maze-type slot 452 of the guide tube 320 according to a predetermined sequence, the axially moveable core 312 may be coupled to the detachable implant 304. In addition, the shape of the maze-type slot 452 may provide limited axial decoupling between the axially moveable core 312 and the detachable implant 304 along the keyed portion 456 of the maze-type slot 452, such as described above with respect to the slider assembly 400 of FIGS. 21-21E.

Figure 29C:
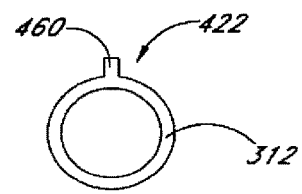
FIG. 29C is an end view of the axially moveable core of FIG. 29A.
Figure 29D:
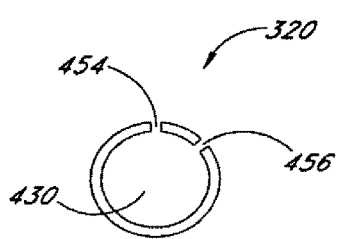
FIG. 29D is an end view of the guide tube of the slider assembly of the implant of FIG. 29A.
Figure 29E:
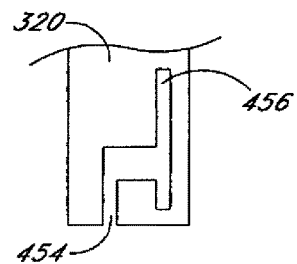
FIG. 29E is a side elevational view of one embodiment of a maze-type slotted guide tube in accordance with one embodiment of the present invention.
Figure 29F:
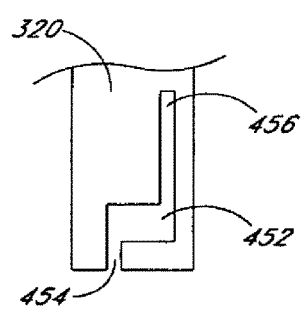
FIG. 29F is a side elevational view of another embodiment of a maze-type slotted guide tube in accordance with one embodiment of the present invention.
Figure 29G:
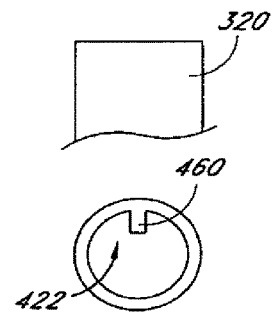
FIG. 29G is an end view of an axially moveable core in accordance with another embodiment of the present invention.

In another embodiment, the maze-type slot 452 of the bayonet mount 450 is provided on the axially moveable core 312, and the flange 460 of the bayonet mount 450 is provided on the guide tube 320 of the slider assembly 400. The flange 460 may extend in a radial outward direction, such as shown in FIG. 29C, or may extend in a radial inward direction, such as shown in FIG. 29G. In another embodiment, the flange 460 extends in both radial outward and radial inward directions.

In other embodiments, a slider assembly need not be connected to the implant, and for example, can be provided as part of the axially moveable core, or even the deployment handle in order to decouple axial movement between the implant and delivery system. For example, in one embodiment, an axially moveable core may include two concentric or axially aligned tubes, slidably moveable with respect to one another, such as, for example, an outer tube and an inner tube. The outer tube may include a mating surface on or near its distal end to engage a mating surface on the distal hub, or elsewhere on the implant. The outer tube slidably engages an inner tube, which enters the outer tube at the outer tube's proximal end. In one embodiment, a solid core is used instead of an inner tube. Relative proximal and distal movement of the inner and outer tube is preferably limited by a motion limit. In one embodiment, the motion limit includes at least one cross pin. In other embodiments, the motion limit includes at least one flare, annular ring, bump, or other suitable mechanism as is well known to those of skill in the art. The inner tube extends preferably to a handle as described above for operating the axially moveable core. The engagement of the outer tube and the inner tube of the axially moveable core may occur anywhere between the handle and the implant along the length of the core.

In another embodiment, the inner tube includes a mating surface on its distal end to engage a mating surface on the distal hub of the implant. The inner tube slidably engages an outer tube, which at least partially covers the inner tube at the inner tube's proximal end. Relative proximal and distal movement of the inner and outer tube is preferably limited by a motion limit as described above, with the outer tube extending outside of the patient and operably connected to a handle.

Figure 29H:
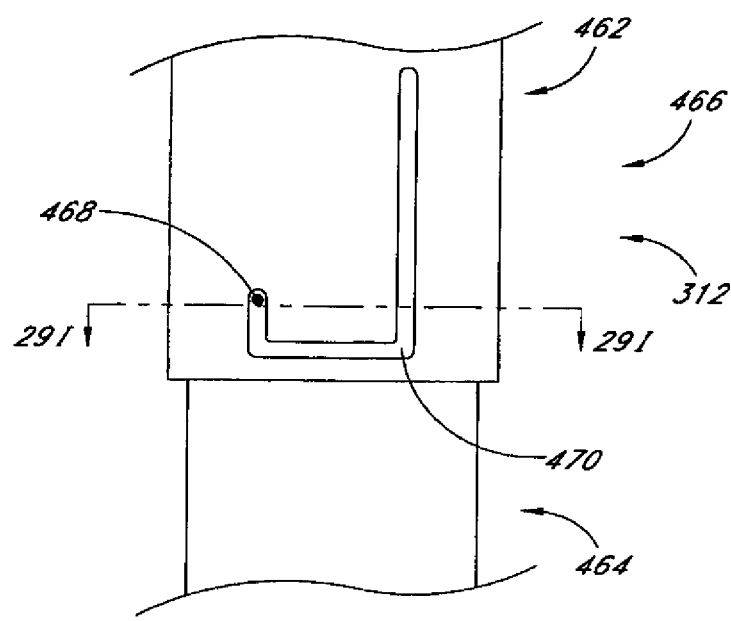
FIG. 29H is one embodiment of a key mount coupling a first and second portion of an axially moveable core in accordance with one embodiment of the present invention.
Figure 29I:
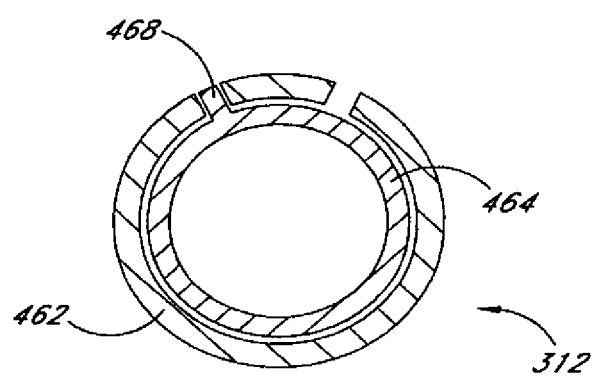
FIG. 29I is a schematic cross sectional view of the key mount of FIG. 29H taken along cut line 29I-29I.

In another embodiment as shown in FIGS. 29H-I, a first portion 462 of the axially moveable core 312, and a second portion 464 of the axially moveable core 312 are coupled to one another with a key mount 462. The second portion 464 includes a flange 468, pin, or equivalent structure, which engages a maze-type slot 470 of the first portion 462 of the axially moveable core 312. By pulling, rotating, and pushing the first portion 462 with respect to the second portion 464 according to a predetermined sequence, limited axial decoupling between the first portion 462 and second portion 464 is achieved.

In one embodiment, the first portion 462 comprises a proximal portion of the axially moveable core 312, and the second portion 464 comprises a distal portion of the axially moveable core 312. In another embodiment, the first portion 462 comprises a distal portion of the axially moveable core 312, and the second portion 464 comprises a proximal portion of the axially moveable core 312. In one embodiment, the flange 468 extends in an outward radial direction, such as shown in FIG. 29I. In another embodiment, the flange 468 extends in an inward radial direction, or in both, radially outward and inward directions.

Alternatively, in another embodiment, a slider assembly can be provided as part of a deployment handle. In one embodiment, the distal portion of an axially moveable core includes a mating surface to engage a mating surface of the distal hub of the implant. The deployment handle can include a guide tube and an internally slideable nut, or other slider assembly such as described above, for receiving the proximal end of the axially moveable core.

Figure 30:
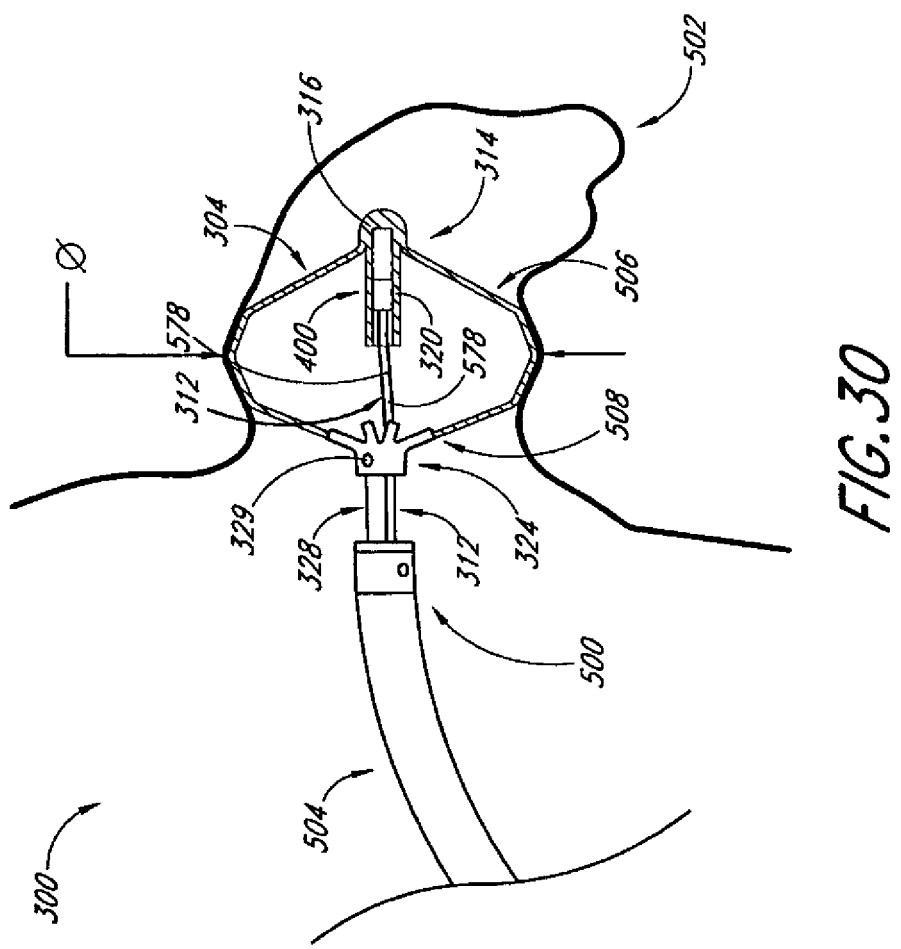
FIG. 30 is a schematic view of a deployment system delivering an implantable containment device to the left atrial appendage.

FIG. 30 illustrates a deployment system 300, having an implant 304 and a delivery system 500, in accordance with one embodiment of the present invention. In a preferred embodiment, the implant 304 is a transluminally delivered device designed to occlude or contain particles within the left atrial appendage 502 (LAA 502) and prevent thrombus from forming in, and emboli from originating from, the LAA 502. The deployment system as described herein incorporates a slider assembly 400 such as described with respect to FIGS. 21-21E above.

The delivery system 500 preferably may be used to deliver the implant 304 to occlude or block the LAA 502 in a patient with atrial fibrillation. The delivery system 500 preferably is compatible for use with a delivery sheath 504 (e.g., a transseptal sheath), shown in FIGS. 38A-38C. The delivery system 500 and implant 304 preferably are designed to allow the implant 304 to be positioned, repositioned, and retrieved from the LAA 502 if necessary. Injection ports 546, 548, as shown in FIGS. 32 and 33, preferably are provided in the delivery system 500 to allow contrast injection proximally and distally of the implant 304 to facilitate in-vivo assessment of the positioning and seal quality of the implant 304.

Figure 31:
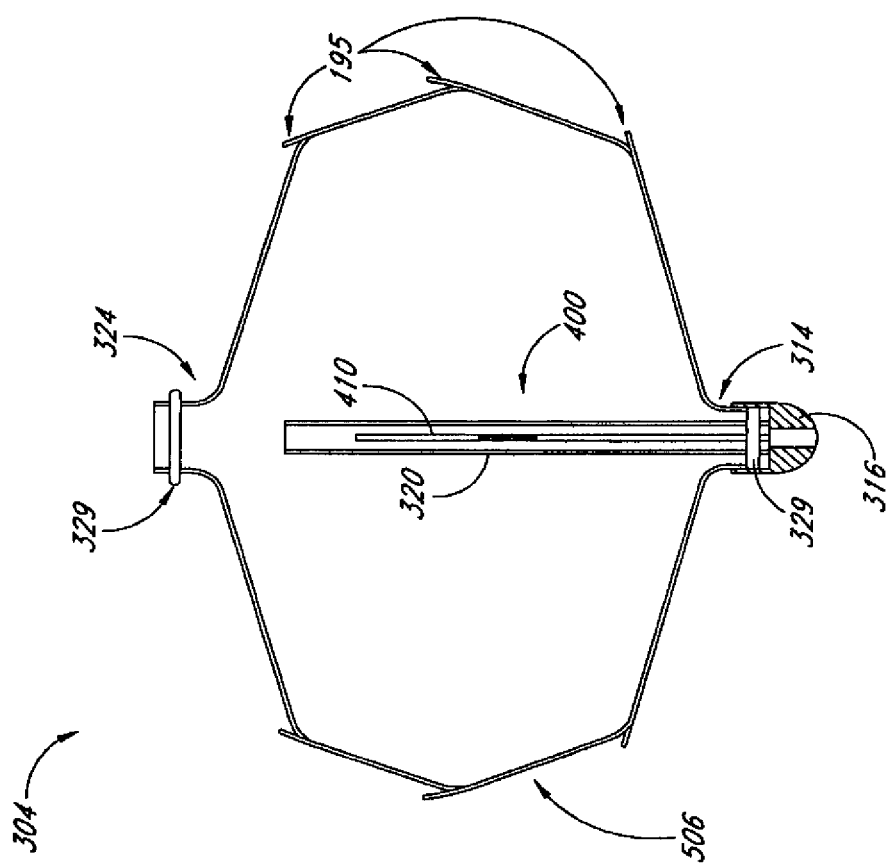
FIG. 31 is a schematic cross sectional view of an implantable containment device built in accordance with one embodiment of the present invention.

As shown in FIG. 31, the implant 304 preferably is available in a range of sizes to accommodate the anatomy of a patient's LAA 502. The implant 304 preferably comprises a frame 506 and a membrane (not shown) on a proximal face of the implant, such as described above. The frame 506 preferably is constructed of self-expanding nitinol supports. The membrane preferably is constructed of a fabric covering, such as one made of ePTFE, or an ePTFE/PE laminate. To attach the membrane to the frame 506, a PE mesh preferably is placed against the supports, with one sheet of ePTFE preferably placed over the PE mesh and another sheet of ePTFE preferably placed on an opposite side of the supports. The membrane preferably is heated on both sides causing the PE to melt into both sheets of ePTFE, thereby surrounding a portion of the frame 506. The nitinol supports allow the implant 304 to self-expand in the appendage 502, covering the orifice with the laminated fabric. The porous ePTFE/PE lamination facilitates rapid endothelialization and healing.

As shown in FIGS. 30 and 31, the implant 304 preferably extends from a proximal end or hub 324 to a distal end or hub 314. In some embodiments, the proximal hub 324 is coupled with a crosspin 329 as described above. In some embodiments the distal hub 314 is coupled with a slider assembly 400 as described above. The distal hub 314 preferably is coupled with an implant plug 316. In one embodiment, the implant plug 316 comprises an atraumatic tip, such that contact between the atraumatic tip and the inside surface of the LAA 502 does not cause significant damage to the LAA 502. The implant 304 preferably is expandable and collapsible. The implant 304 preferably comprises anchors 195 that extend from the frame 506 when the implant 304 is expanded as described above.

Figure 33:
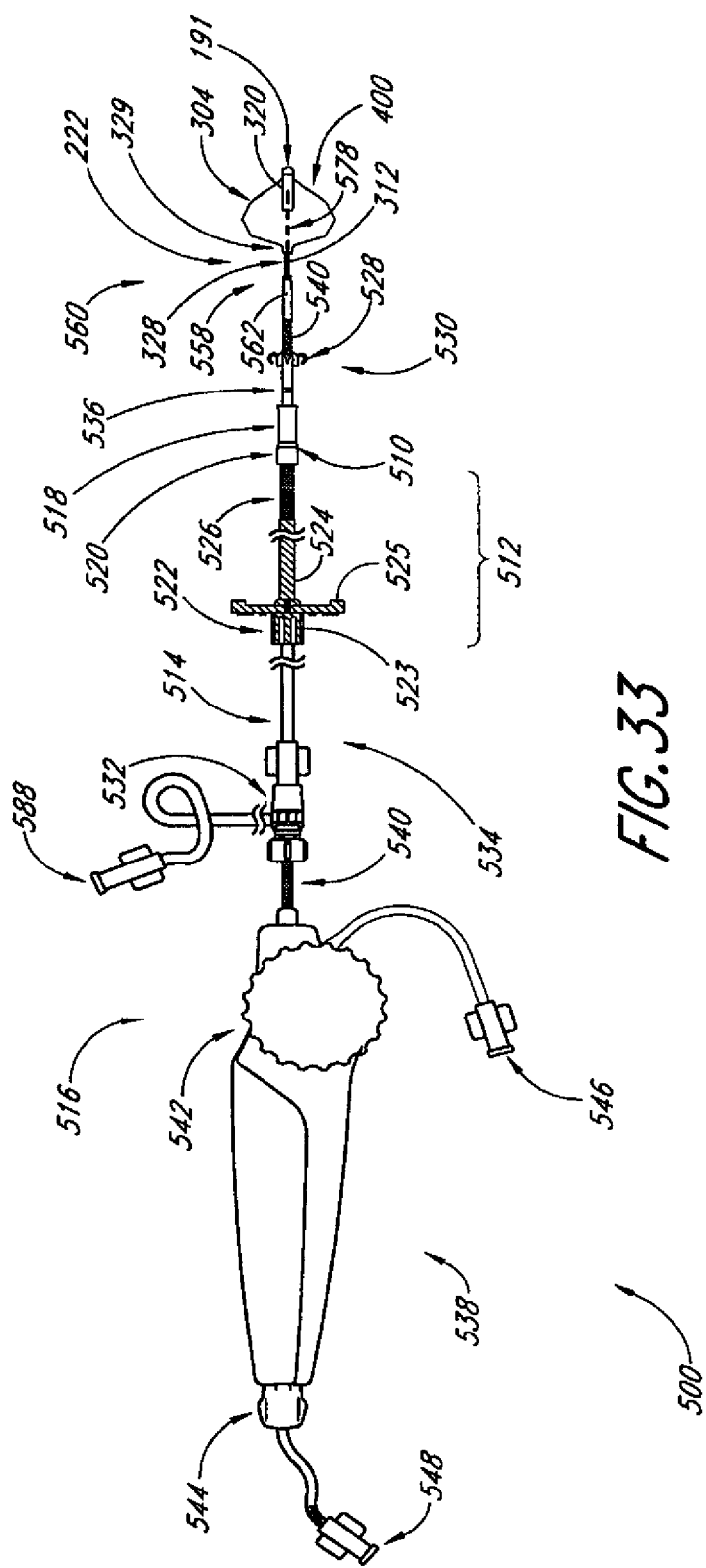
FIG. 33 is a schematic view of the delivery system of FIG. 32, shown attached to an implantable containment device.

As shown in FIGS. 32 and 33, the delivery system 500 preferably comprises a peel-away sheath 512, a recapture sheath 514, a deployment catheter 516, and an axially moveable core 312, each described further below. In addition, FIG. 32 illustrates the deployment system without a loading collar 510, and FIG. 33 illustrates the deployment system with a loading collar 510, with the system operably connected to an implant 304.

The deployment catheter 516, which is analogous to deployment catheter 302 described above, preferably comprises a deployment handle 538 and a multi-lumen shaft 540. As shown in FIGS. 32 and 33, the deployment handle 538 preferably comprises a control knob 542, a release knob 544, a proximal injection port 546 and a distal injection port 548. The multi-lumen shaft 540 preferably comprises a four-lumen shaft shown in FIG. 32A. The multi-lumen shaft 540 preferably comprises a core lumen 550 for holding an axially moveable core 312, a control line lumen 552 and two proximal injection lumens 554 in communication with proximal injection port 546.

Figure 36:
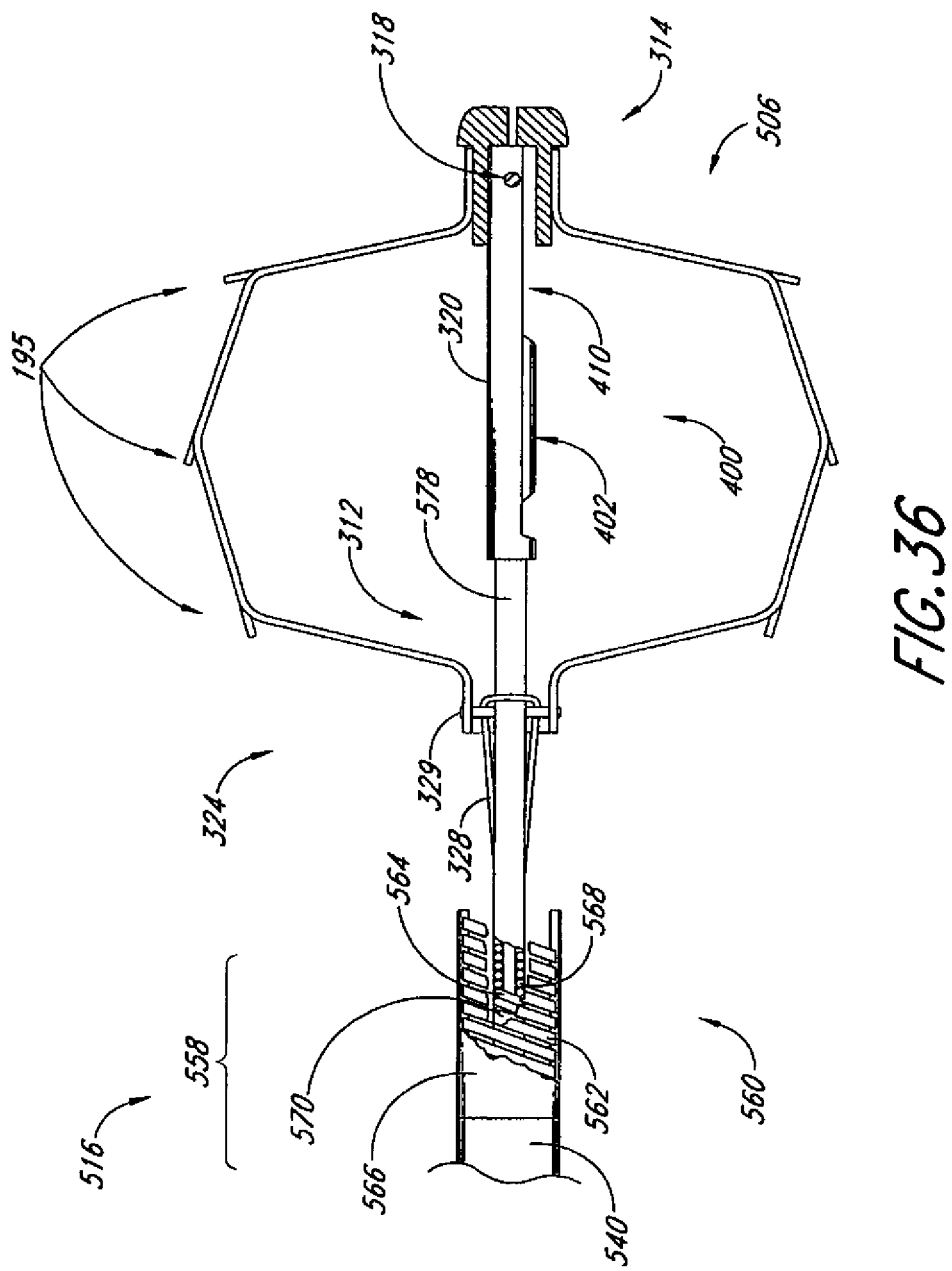
FIG. 36 is an enlarged partial cross sectional view of the deployment system of FIG. 32.

An axially moveable core 312 preferably extends from the deployment handle 538 through the core lumen 550 of the catheter 516 and couples the implant 304 to the delivery system 500 through a slider assembly 400 as described above. Referring to FIGS. 30, 33 and 36, a control line 328 (referred to previously as a pull wire 328) preferably extends through the control line lumen 552 and preferably couples a proximal hub 324 of the implant 304 to the deployment handle control knob 542, allowing for implant 304 expansion and collapse. The control line 328 preferably extends around a portion of the axially movable core 312 near the proximal hub 324 of the implant 304, and is coupled to the implant 304 by crosspin 329, as described above.

As shown in FIG. 36 (which is similar to FIG. 21), the deployment catheter 516 preferably comprises a flexible catheter section 562 at its distal end, which in some embodiments is a spiral cut tubular section housed in a polymer sleeve 566. The flexible catheter section 562 may be coupled to a distal end of multilumen shaft 540.

As shown in FIGS. 36 and 37, the axially moveable core 312 preferably includes a hollow proximal shaft 576 and a hollow distal shaft 578 with a flexible hollow core section 564 therebetween, all co-axially aligned and connected. In one embodiment, the proximal end of the distal shaft 578 is attached to the distal end of the flexible core section 564, and the proximal end of the flexible core section 564 is attached to the distal end of the proximal shaft 576. In some embodiments, the flexible core section 564 has a spring coil section 568 housed in a polymer sleeve 570, the spring coil section 568 preferably coupled with the shafts 576 and 578 on first and second ends 572, 574.

The axially moveable core 312 preferably is disposed within the deployment catheter 516 such that the flexible core section 564 may be linearly co-located with the flexible catheter section 562 at a distal portion 560 of the delivery system 500 during appropriate times during a procedure, as shown in FIG. 36. When the flexible core section 564 is aligned and linearly co-located with the flexible catheter section 562, the sections preferably cooperate to form a delivery system flexible segment 558. As shown in FIGS. 32, 33, and 36, the delivery system flexible segment 558 preferably is located toward a distal end 560 of the delivery system 500.

In one embodiment, shown in FIG. 37, the distal shaft 578, flexible core section 564, and proximal shaft 576 are attached by welding. Small windows 580 may be provided to allow welding materials to flow between the shafts 564, 576 and 578 and provide stronger bonding therebetween. In another embodiment, solder, glue, or press-fitting is used to attach shafts 564, 576, and 578 to one another, as is well known to those of skill in the art. In another embodiment, the shafts 564, 576 and 578 are formed from a single tube, for example, a laser-cut tube. In other embodiments, more than one tube may be used to form each of the shafts 564, 576 and 578. For example, FIG. 37 illustrates proximal shaft 576 comprising two tubes connected by welding such as described above.

Referring to FIG. 37A, distal contrast media preferably can be injected through a lumen 582 in the shafts 576 and 578 for determining the placement of the implant 304. This lumen may be in fluid communication with distal injection port 548, shown in FIGS. 32 and 33. The distal shaft 578 preferably comprises a mating surface 584 and a radiopaque marker 586, such as described above. In one embodiment, the mating surface 584 is a threaded surface. The distal shaft 578 preferably is releasably coupled through the implant 304 with the slider assembly 400, such as described above.

When the delivery system 500 is assembled, the recapture sheath 514 is preferably loaded over the deployment catheter 516, distal to the handle 538, as shown in FIGS. 32 and 33. The recapture sheath 514 preferably is designed to allow recapture of the implant 304 prior to its final release such as described with respect to retrieval catheter 360 above. Recapture petals or flares 528 preferably are provided on the distal end 530 of the recapture sheath 514 to cover the anchors 195 of the implant 304 during retrieval into the delivery sheath 504, as described above with respect to FIGS. 20A-20C, and further below. A Touhy-Borst adapter or valve 532 preferably is attached to the proximal end 534 of the recapture sheath 514. The recapture sheath 514 preferably comprises a radiopaque marker 536 on its distal end 530 near the recapture flares 528. The recapture sheath 514 preferably comprises a recapture sheath injection port 588 for delivering fluid proximal the implant 304.

The peel-away sheath 512 preferably is provided over a portion of the recapture sheath 514, between Touhy-Borst valve 532 and recapture flares 528. The peel-away sheath 512 preferably is used to introduce the delivery system 500 into a delivery sheath 504 shown in FIGS. 38A-38C, described below. As shown in FIGS. 32 and 33, the peel-away sheath 512 preferably comprises a locking collar 522, a peel-away section 524, and a reinforced section 526. The locking collar can be unlocked relative to peel-away section 524, and preferably includes a threaded hub 523 that releasably engages tabs 525 of the peel-away section 524.

Figure 34B:
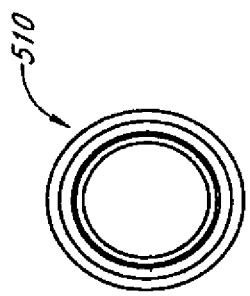
FIGS. 34A and 34B are a schematic cross sectional view and an end view, respectively, of a loading collar used in the system of FIG. 32.
Figure 34A:
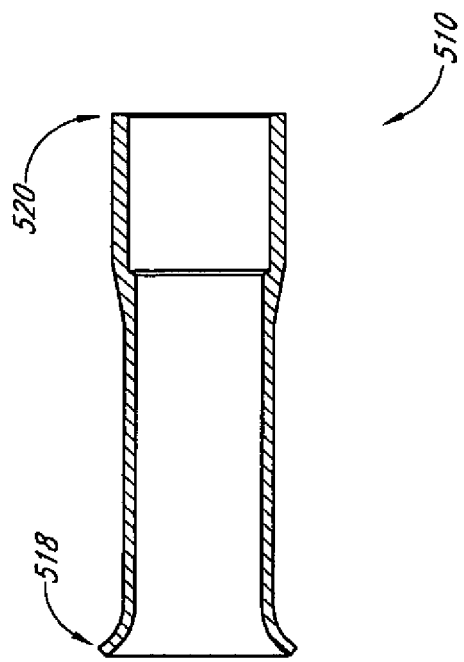
Figure 35:
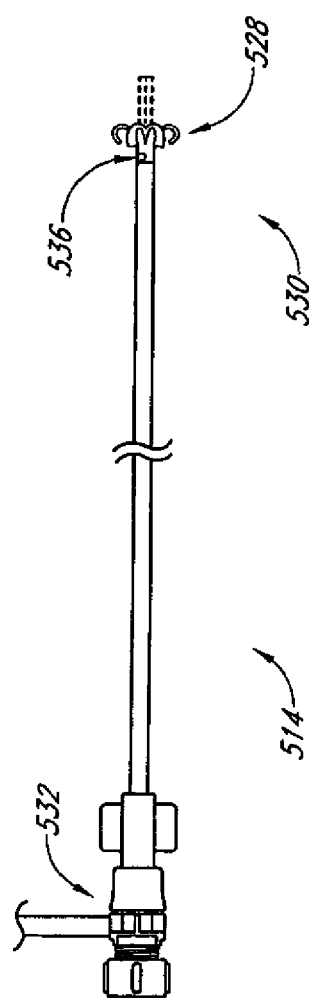
FIG. 35 is a schematic view of a recapture sheath used in the system of FIG. 32.

The loading collar 510 preferably is located over a portion of the peel-away sheath 512 and a portion of the recapture sheath 514 with its proximal end being located over the peel-away sheath 512 at its distal end loaded over recapture sheath 514. The loading collar 510 preferably accommodates loading a collapsed implant 304 into the peel-away sheath 512 as described below. As shown in FIGS. 33 and 34, the loading collar 510 preferably comprises a first end portion 518 adapted to receive and extend over a collapsed implant 304, and a second end portion 520 configured to guide the collapsed implant 304 into the peel-away sheath 512. The loading collar 510 preferably is made of stainless steel.

To assemble the delivery system, the axially movable core 312 and control line 328 preferably are fed into the multi-lumen shaft 540 of the deployment catheter 516. The multi-lumen shaft 540 preferably is then coupled with components of the deployment handle 538 and the injection port components 546, 548. The peel-away sheath 512 and the loading collar 510 preferably are slid onto the recapture sheath 514, and the recapture sheath 514 is slid onto the deployment catheter 516. The implant 304 preferably is then loaded on an end of the axially movable core 312 and coupled with the control line 328. In one embodiment, the implant 304 is loaded on an end of the axially movable core 312 by screwing the axially movable core 312 into the slider nut 402 of the slider assembly 400. The control knob 542 and outer casing of the deployment handle 538 preferably are then coupled with the system.

The deployment system 300 preferably is used in connection with a delivery sheath 504 to advance the implant 304 for deployment in a patient. As shown in FIGS. 30 and 38A-38C, the delivery sheath 504 is a tubular device that in one embodiment can be advanced over a guidewire (not shown) for accessing the LAA 502 of a patient. Delivery sheath 504 in one embodiment has a permanent bend 594, as shown in the views of FIGS. 38A and 38B. A hemostasis valve 596 is provided at the proximal end of transseptal sheath. A fluid injection port 598 is also provided at the proximal end to deliver fluid such as contrast media through the transseptal sheath. Systems and methods for implanting the device 304 in the LAA 502 are described further below.

In one embodiment, the system and method preferably allows for access and assessment of the LAA 502. A guidewire (not shown) preferably is used to access the superior or inferior vena cava through groin access. For example, a delivery sheath 504 preferably is advanced over the guidewire and into the superior vena cava. The guidewire preferably is removed and replaced with a transseptal needle (not shown). The delivery sheath 504 preferably is retracted inferiorly so that the bend 594 in delivery sheath 504 directs the distal tip of the delivery sheath 504 toward the fossa ovalis. The needle preferably is advanced to puncture the fossa ovalis. The delivery sheath 504 preferably is advanced to establish access to the LAA 502 and the needle preferably is retracted. Further details or disclosure are provided in copending U.S. patent application Ser. Nos. 09/435,562 and 10/033,371, the entireties of which are hereby incorporated by reference. In one embodiment, the implant 304 can be deployed within the LAA 502 as an adjunct to surgical heart procedures, as described below. The delivery sheath 504 for establishing access to the LAA 502 can be generally straight and can have a length less than the length of the delivery sheath 504 which is advanced through the superior or inferior vena cava.

After properly preparing a delivery sheath 504 for LAA 502 access, the size of the neck diameter and morphology of the LAA 502 preferably is determined by advancing the delivery sheath 504 to the distal portion of the LAA 502 and injecting contrast media to obtain an initial left atrial appendogram. The neck diameter preferably is measured approximately 5 mm in from the ostium of the LAA 502 at end diastole.

In one embodiment, the system and method preferably allows for selection and preparation of a deployment system 300. A deployment system 300 preferably comprises an implant 304 of an appropriate size for placement in a patient. Initially, the implant 304 preferably is in an expanded configuration, with axially moveable core 312 engaging slider assembly 400, as described above. The recapture sheath 514 preferably is positioned so it covers and supports the flexible segment 558 of the delivery system 500, wherein the flexible catheter section 562 of deployment catheter 302 and flexible core section 564 of axially moveable core 312 are aligned. The Touhy-Borst valve 532 preferably is tightened over the deployment catheter 516 to prevent relative movement between recapture sheath 514 and deployment catheter 516. The loading collar 510 and peel-away sheath 512 preferably are positioned so they are at the base of the recapture flares 528, proximal thereto.

The delivery system 500 preferably is loaded by rotating the control knob 542 counterclockwise until the implant 304 is fully collapsed. Preferably, at least a portion of the control line 328 is coupled with the control knob 542 such that rotation of the control knob 542 in the counterclockwise direction retracts at least a portion of the control line 328. Retraction of the control line 328 preferably places tension on the proximal hub 324 of the implant 304, because a portion of the control line 328 preferably is coupled with the proximal hub 324 by a pin 329. While the distal portion of the axially moveable core 312 engages slider assembly 400 and applies a distal force to distal hub 314 of the implant 304, tension in the control line 328 preferably causes the proximal hub 324 of the implant 304 to move proximally relative the axially moveable core 312, thereby collapsing the implant 304.

The diameter of the implant 304 preferably is reduced to approximately ⅓.sup.rd or less of its original diameter when collapsed. The loading collar 510 and peel-away sheath 512 are then advanced distally over the flares 528 and implant 304 until the distal tip of the implant 304 is aligned with the distal end of the peel-away sheath 512 and the distal end of the loading collar is about 1.5 cm from the distal tip of the implant At this point, the flares 528 partially cover the implant. The loading collar 510 preferably is removed and discarded.

With the implant 304 partially within the recapture sheath 514 and retracted within the peel-away sheath 512, the entire system preferably is flushed with sterile heparinized saline after attaching stopcocks to the recapture sheath injection port 588, the proximal injection port 546 and distal injection port 548 of the delivery system 500. The recapture sheath 514 and the Touhy-Borst valve 532 are first thoroughly flushed through port 588. Then the distal injection port 548 and the proximal injection port 546 of the deployment handle 538 are preferably flushed through. The distal injection port 548 is in fluid communication with lumen 426 of axially moveable core 312, and proximal injection port 546 is in fluid communication with injection lumens 554 of multilumen shaft 540. The delivery sheath 504 placement preferably is reconfirmed using fluoroscopy and contrast media injection.

The delivery system 500, as described above, with implant 304 inserted therein, preferably is then inserted into the proximal end of the delivery sheath 504. To avoid introducing air into the delivery sheath 504 during insertion of the delivery system 500, a continual, slow flush of sterile heparinized saline preferably is applied through the proximal injection port 546 of the deployment handle 538 to the distal end of the deployment catheter 516 until the tip of the peel-away sheath 512 has been inserted into, and stops in, the hemostatic valve of the delivery sheath 504. Preferably, the distal tip of the peel-away sheath 512 is inserted approximately 5 mm relative to the proximal end of the delivery sheath 504.

Under fluoroscopy, the recapture sheath 514 and deployment catheter 516 preferably are advanced, relative to the peel-away sheath 512, approximately 20-30 cm from the proximal end of the transseptal sheath, and the system 500 preferably is evaluated for trapped air. The peel-away sheath 512 is preferably not advanced into the delivery sheath 504 due to the hemostasis valve 596 blocking its passage. If air is present in the system 500, it may be removed by aspirating through the distal injection port 548, recapture sheath injection port 588, or proximal injection port 546. If air cannot be aspirated, the deployment catheter 516 and recapture sheath 514 preferably are moved proximally and the delivery system 500 preferably is removed from the delivery sheath 504. All air preferably is aspirated and the flushing/introduction procedure preferably is repeated.

The peel-away sheath 512 preferably is manually slid proximally to the proximal end 534 of the recapture sheath 514. The Touhy-Borst valve 532 preferably is loosened and the deployment catheter 516 preferably is advanced distally relative to the recapture sheath 514 until the deployment handle 538 is within about 2 cm of the Touhy-Borst valve 532 of the recapture sheath 514. This causes the implant 304 to be advanced distally within the delivery sheath 504 such that the recapture sheath 514 no longer covers the implant 304 or the flexible section 558. The Touhy-Borst valve 532 preferably is tightened to secure the deployment catheter 516 to fix relative movement between the deployment catheter 516 and recapture sheath 514.

Under fluoroscopy, the implant 304 preferably is advanced to the tip of the delivery sheath 504 by distal movement of the delivery catheter 302. The distal hub 314 of implant 304 preferably is aligned with a delivery sheathtip radiopaque marker 590. Under fluoroscopy, the sheath 504 positioning within the LAA 502 preferably is confirmed with a distal contrast media injection.

The position of the implant 304 preferably is maintained by holding the deployment handle 538 stable. The delivery sheath 504 preferably is withdrawn proximally until its tip radiopaque marker 590 is aligned with the distal end of the deployment catheter flexible segment 558. This preferably exposes the implant 304.

Under fluoroscopy, the implant 304 preferably is expanded by rotating the control knob 542 clockwise until it stops. Rotating the control knob 542 preferably releases tension on the control line 328, preferably allowing the implant 304 to expand. The implant 304 preferably is self-expanding. After expansion, any tension on the LAA 502 preferably is removed by carefully retracting the deployment handle 538 under fluoroscopy until the radiopaque marker 586 on the axially movable core 312 moves proximally approximately 1-2 mm in the guide tube 320. The position of the implant 304 relative the LAA 502 preferably is not altered because the axially movable core 312 preferably is coupled with the slider assembly 400 allowing for relative movement between the implant 304 and the axially movable core 312. The slider assembly 400 preferably allows for the distal portion of the axially movable core 312 to be slightly retracted proximally from the distal hub 314 of the implant 304, thereby removing any axial tension that may be acting on the implant 304 through the axially movable core 312. The radiopaque marker 586 preferably is about 1-2 mm proximal from the implant 304 distal hub 314, and the delivery sheath 592 tip preferably is about 2-3 mm proximal from the implant proximal hub 324, thereby indicating a neutral position.

Under fluoroscopy, the expanded diameter (.O slashed. in FIG. 30) of the implant 304 preferably is measured in at least two views to assess the position of the implant within the LAA 502. The measured implant diameter .O slashed. preferably is compared to the maximum expanded diameter.

Preferably, the labeled proximal and distal injection ports 546, 548 of the deployment handle 538 shown in FIG. 32, correlate with the proximal and distal contrast media injections. The proximal contrast media injections are delivered through the delivery catheter lumen 554 to a location proximal to the implant 304. The distal contrast media injections are delivered through the axially movable core 312 to a location distal to the implant 304. Proximal contrast media injections preferably are completed in two views. If the injection rate is insufficient, the recapture sheath injection port 588 may be used independently or in conjunction with the proximal injection port 546 to deliver fluid to a location proximal to the implant 304.

If satisfactory results are seen, any transverse tension on the LAA 502 preferably is released by exposing the flexible segment 558 of the delivery system 500. The flexible catheter section 562 and the flexible core section 564 preferably are linearly co-located to cooperate as the flexible segment 558 of the delivery system 500. This preferably is accomplished by retracting the delivery sheath 504 proximally approximately 2 cm to expose the flexible segment. By exposing the flexible segment 558, the flexible segment 558 preferably will flex to allow the implant 304 to sit within the LAA 502 free from transverse forces that may be created, for example, by contractions of the heart acting against the delivery sheath 504 or deployment catheter 516.

Once the flexible segment 558 is exposed, distal contrast media injections preferably are completed in at least two views to verify proper positioning of the implant 304. A flush of saline preferably is used as needed between injections to clear the contrast media from the LAA 502. Following the contrast media injections, the delivery sheath 504 preferably is advanced distally to cover the flexible segment 558.

If implant 304 position or results are sub-optimal, the implant 304 preferably may be collapsed and repositioned in the LAA 502. To achieve this, under fluoroscopy, the deployment handle 538 preferably is advanced distally to place the radiopaque marker 586 of the axially moveable core 312 at the distal hub 314 of the implant 304. The distal end of the delivery sheath 504 preferably is aligned with the distal end of the flexible segment 558. The control knob 542 preferably is rotated until the implant 304 has been collapsed to approximately ⅓.sup.rd or less of its expanded diameter. The control knob 542 preferably acts on the control line 328 to place tension on the proximal hub 324 of the implant 304, pulling the proximal hub 324 of the implant 304 proximally relative the distal hub 314 of the implant 304 to collapse the implant 304. The implant 304 preferably can be repositioned and re-expanded.

The stability of the implant 304 preferably is verified in several views. Stability tests preferably are preformed in the following manner. A contrast media filled syringe preferably is connected to the distal injection port 548 of the deployment handle 538. Under fluoroscopy, at least about a 10 mm gap between the tip of the delivery sheath 504 and the proximal hub 222 of the implant 304 is preferably confirmed.

The stability of the implant 304 in the LAA 502 preferably is evaluated using fluoroscopy and echocardiography. The recapture sheath Touhy-Borst valve 532 preferably is loosened. Then the deployment handle 538 preferably is alternately retracted and advanced about 5-10 mm while maintaining the position of the delivery sheath 504 and simultaneously injecting contrast media through the distal injection port 548. This tests how well the implant is held within the LAA 502.

If the implant stability tests are unacceptable, the implant 304 preferably may be collapsed and repositioned as described above. If repositioning the implant 304 does not achieve an acceptable result, the implant 304 preferably may be collapsed and recaptured as described further below.

The implant 304 preferably meets the following acceptance criteria, associated with the assessment techniques listed below, prior to being released. The assessment techniques to be evaluated preferably include 1) residual compression; 2) implant location; 3) anchor engagement; 4) seal quality; and 5) stability. For residual compression, the implant diameter .O slashed., as measured by fluoroscopic imaging, preferably is less than the maximum expanded diameter of the implant 304. For implant location, the proximal sealing surface of the implant 304 preferably is positioned between the LAA 502 ostium and sources of thrombus formation (pectinates, secondary lobes, etc.) (preferably imaged in at least two views). For anchor engagement, the implant frame 506 preferably is positioned within the LAA 502 so as to completely engage a middle row of anchors 195 in an LAA 502 wall (preferably imaged in at least two views). For seal quality, the contrast injections preferably show leakage rated no worse than mild (preferably defined as a flow of contrast media, well defined, and filling one-third of the LAA 502 during a proximal injection over a period of up to about five ventricular beats, preferably imaged in at least two views). For stability, there preferably is no migration or movement of the implant 304 relative to the LAA 502 wall as a result of the Stability Test.

If implant recapture is necessary, because a different size implant 304 is necessary or desired, or if acceptable positioning or sealing cannot be achieved, the implant 304 preferably is fully collapsed as described above. Once the implant 304 is collapsed, the locking collar 522 of the peel away sheath 512 preferably is unlocked. The peel-away portion 524 of the peel-away sheath 512 preferably is split up to the reinforced section 526 and removed. The reinforced section 526 of the peel-away sheath 512 preferably is slid proximally to the hub of the recapture sheath 514. The Touhy-Borst valve 532 on the proximal end of the recapture sheath 514 preferably is slightly loosened to allow smooth movement of the sheath 514 over deployment catheter 516 without allowing air to enter past the Touhy-Borst valve 532 seal. By removing the peel-away portion 524 of peel-away sheath 512, the recapture sheath 514 can now be advanced further distally relative to the transseptal sheath.

While holding the deployment catheter 516 and delivery sheath 504 in place, the recapture sheath 514 preferably is advanced distally into the delivery sheath 504 until a half marker band 536 on the recapture sheath 514 is aligned with a full marker band 590 on the delivery sheath 504. This preferably exposes the recapture flares 528 outside the transseptal sheath.

The collapsed implant 304 preferably is retracted into the recapture sheath 514 by simultaneously pulling the deployment handle 538 and maintaining the position of the recapture sheath 514 until approximately half the implant 304 is seated in the recapture sheath 514. The Touhy-Borst valve 532 on the recapture sheath 514 preferably is tightened over the deployment catheter 516. The recapture sheath 514 and implant 304 preferably are retracted into the delivery sheath 504 by pulling on the recapture sheath 514 while maintaining the position of the delivery sheath 504, preferably maintaining left atrial access. The recapture flares 528 of the recapture sheath 514 preferably cover at least some of the anchor elements 195 on the implant 304 as the implant is retracted proximally into the delivery sheath 504. Further details are described above with respect to FIGS. 20A-20C.

If the implant's position and function are acceptable, and implant recapture is not necessary, the implant 304 preferably is released from the delivery system 500. Under fluoroscopy, the delivery sheath 504 preferably is advanced to the proximal hub 324 of the implant 304 for support. The release knob 544 on the proximal end of the deployment handle 538 preferably is rotated to release the implant 304. Rotating the release knob 544 preferably causes a threaded portion 584 of the distal shaft 578 of the axially movable core 312 to rotate with respect to the slider assembly 400 such that the threaded section 584 preferably is decoupled from the slider assembly 400. Under fluoroscopy, after the axially movable core 312 is decoupled from the implant 304, the release knob 544 preferably is retracted until the distal end 578 of the axially movable core 312 is at least about 2 cm within the delivery sheath 504.

Under fluoroscopy, while assuring that transseptal access is maintained, the delivery system 500 preferably is retracted and removed through the delivery sheath 504. Under fluoroscopy, the delivery sheath 504 position preferably is verified to be approximately 1 cm away from the face of the implant 304. Contrast injections, fluoroscopy and/or echocardiography preferably may be used to confirm proper positioning and delivery of the implant 304 and containment of the LAA 502. The delivery sheath 504 preferably is withdrawn.

In addition to the aforementioned techniques, an implant as described above can be delivered, e.g., using conventional transthoracic surgical, minimally invasive, or port access approaches. Delivery can be made or done in conjunction with surgical procedures. Implant 304, for example, can be used in conjunction with various surgical heart procedures related to the heart (e.g., mitral valve repair) or surgical procedures in the region surrounding the heart. The delivery system 500 and delivery sheath 504 can be used to locate and deploy the implant 304 in order to prevent the passage of embolic material from the LAA, such that thrombus remains contained in the LAA 502. Thrombus remains contained in the LAA 502 because the implant 304 inhibits thrombus within the LAA 502 from passing through the orifice of the LAA 502 and into the patient's blood stream. Additionally, the deployed implant 304 located in the LAA 502 can provide a smooth, non-thrombogenic surface facing the left atrium. Preferably, the smooth, non-thrombogenic surface facing the left atrium will not promote blood clots to form proximate to the LAA 502. Access to the heart may be provided by surgical procedures in order to deploy the implant 304 in the LAA 502. That is, the implant 304 can be deployed as an adjunct to surgical procedures. Access to the left atrium is provided in one embodiment by obtaining a left atrium access path. The delivery sheath 504 can be located along the left atrium access path to define a delivery path. The delivery system 500 can be used to deliver the implant 304 along the delivery path to a position for deployment. The implant 304 located in the position for deployment can be deployed to block the LAA 502. There are many methods of delivering and deploying the implant 304 as described in further detail below.

In particular, access to the heart of a patient can be provided by various techniques and procedures so that implant 304 can delivered and deployed in the heart. For example, minimally invasive surgery techniques, laparoscopic procedures and/or open surgical procedures can provide the left atrium access path to the heart. In one embodiment, access to the LAA can be provided by access through the chest of the patient, and may include, without limitation, conventional transthoracic surgical approaches, open and semi-open heart procedures, laparoscopic, and port access techniques. Such surgical access and procedures preferably will utilize conventional surgical instruments for accessing the heart and performing surgical procedures on the heart, for example, retractors, rib spreaders, trocars, laparoscopic instruments, forceps, scissors, shears, rongeurs, clip appliers, staplers, sutures, needle holders, bulldogs, clamps, elevators, cauterizing instruments or substances, electrosurgical pens, suction apparatuses, approximators, and/or the like. The implant can be conveniently deployed as an adjunct to a surgical heart procedure, such that the implant can be delivered at the LAA without performing additional complicated procedures for gaining access to the LAA. As used herein the phrase "surgical heart procedure" is a broad phrase and is used in accordance with its ordinary meaning and may include, without limitation, open procedures, semi-open procedures, laparoscopic procedures, open heart surgery and may include procedures for replacing and/or repairing portions of the heart. In one non-limiting exemplifying embodiment, surgical heart procedures include treatment of the heart, such as aortic valve repair, mitral valve repair, pulmonary valve repair, and/or replacement of a heart valve (e.g., a diseased aortic, mitral, or pulmonary valve) with an artificial valve or prosthesis. The known conventional surgical instruments for accessing the heart and performing surgical procedures on the heart can be used in combination with instruments used for these heart treatments. For example, sizing rings, balloons, calipers, gages, and the like can be employed to match an implant/device (such as artificial valve or prosthesis) to an anatomical structure of the heart.

Many times, the access techniques and procedures can be performed by the surgeon and/or a robotic device, such as robotic systems used for performing minimally invasive heart surgery. Those skilled in the art recognize that there are many different ways the heart can be accessed.

In one embodiment, the access to the left atrium can be obtained by creating a left atrium access path. The left atrium access path is a path the can be used to locate the delivery sheath into a patient's body for implant 304 delivery. The left atrium access path can be obtained before, during, or after another surgical heart procedure (e.g., mitral valve repair), which many times can provide the left atrium access path. The left atrium access path can be sized to allow the passing of the delivery sheath 504 along the left atrium access path without injuring the patient. The techniques and procedures for obtaining the left atrium access path can be performed by the surgeon and/or a robotic device.

The left atrium access path can be disposed in various locations in the patient's body. For example, the left atrium access path can be located within the pulmonary vein and to the left atrium. In another embodiment, the left atrium access path can be located outside of the heart and through the wall of the left atrium and into the left atrium. In another embodiment, the left atrium access path is located within the right atrium through a transseptal puncture and passes into the left atrium. In another embodiment, the left atrium access path is located through an opening, for example obtained during an open heart procedure, in the wall of left atrium and into the left atrium. Those skilled in the art recognize that the left atrium access path can be located in various other positions.

The delivery sheath 504 can be positioned along the left atrium access path and can define a delivery path for the delivery of the implant 304. The delivery path is disposed within and along the delivery sheath 504. The delivery sheath 504 is sized to permit the implant 304 to pass along the delivery path through the delivery sheath 504 and out of a distal end 702 of the delivery sheath 504 (as shown in FIG.

30). The delivery sheath 504 can be configured for particular left atrium access paths, which are described herein. The delivery sheath 504, of course, can be used with the delivery system 500 and 300, as described above.

Figure 40:
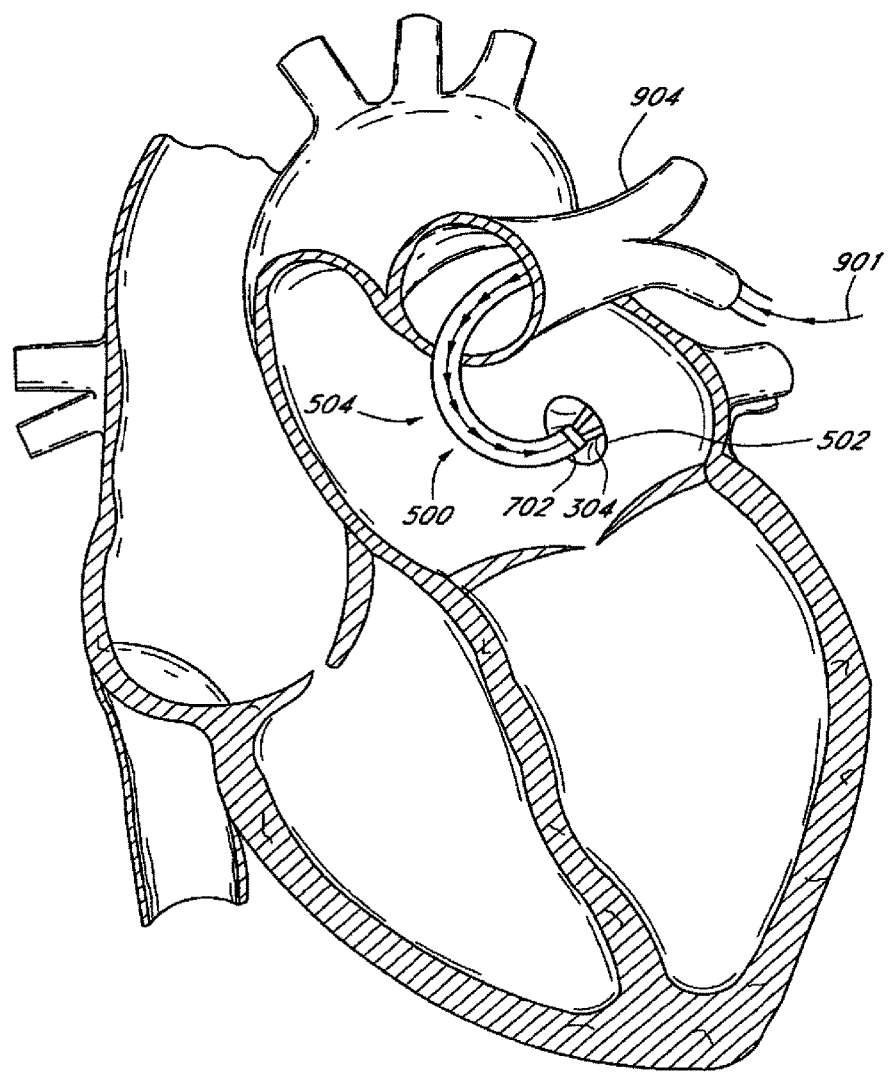
FIG. 40 is a view of a heart and a delivery sheath located along the pulmonary vein.

In the illustrated embodiment of FIG. 40, the implant 304 can be delivered along a delivery path 901 that passes through the pulmonary vein 904 and through the left atrium to the LAA 502, e.g., the distal end 702 of the delivery sheath 504 can be positioned for delivery and deployment of the implant 304. The delivery path 901 can be positioned by inserting the distal end 702 of the delivery sheath 504 into the pulmonary vein 904 and advancing the distal end 702 of the delivery sheath 504 along the pulmonary vein 904 towards the wall of the left atrium. The sheath 504 can be delivered to the pulmonary vein, for example, in a surgical heart procedure, such as in conventional open procedure through the chest of a patient, or in a laparoscopic approach through the chest using trocars and other instruments to direct the delivery sheath 504 to the pulmonary vein. The distal end 702 of the delivery sheath 504 can pass through the chamber of the left atrium such that the distal end 702 of the delivery sheath 504 is proximate to the orifice of the LAA 502. The implant 304 can be delivered through the delivery sheath 504 and along the delivery path 901 as indicated by the arrows. Thus, the delivery sheath 504 defines the delivery path 901 that passes through the pulmonary vein 904, the chamber of the left atrium, and is used to deliver the implant 304 to the LAA 502. Delivery and deployment of the implant 304 can be accomplished using the techniques as described above, or other suitable techniques. In some non-limiting exemplifying embodiments, the delivery sheath 504 has length that is greater than about 15 cm. In some non-limiting exemplifying embodiments, the delivery sheath 504 has a length of about 50 cm or less, and even more preferably about 45 cm or less, about 40 cm or less, about 35 cm or less, about 30 cm or less, about 25 cm or less, about 20 cm or less, about 15 cm or more, or even ranges encompassing such lengths. The delivery sheath 504 can have a length suitable for allowing the surgeon to easily position the delivery sheath 504 through the pulmonary vein (or along other delivery paths described below). For example, in an open procedure, one hand of the surgeon can position the delivery sheath 504 in the heart and the other hand of the surgeon can hold and position the proximal end of delivery sheath 504 outside of chest cavity. Thus, a person can manually position the delivery sheath 504 to deliver the implant into the LAA. Many times, conventional sheaths are long and therefore awkward to stabilize and may be difficult to position both ends of the conventional sheath. Alternatively, the delivery sheath 504 can be positioned by a robotic system, multiple surgeons, and/or other suitable means for positioning.

Figure 41:
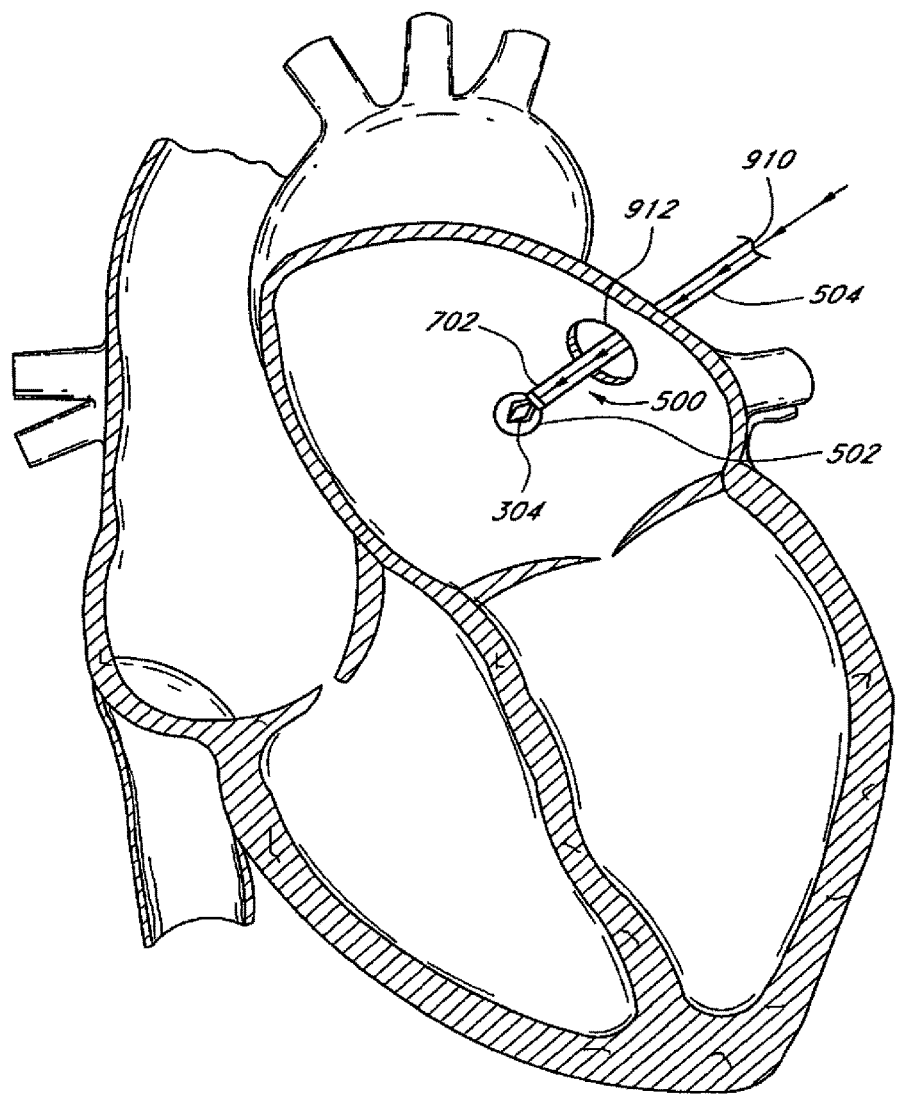
FIG. 41 is a view of a heart and a delivery sheath through an opening of the left atrium.

In the illustrated embodiment of FIG. 41, the implant 304 can be delivered along a delivery path 910 that passes directly through an opening 912 in the wall of the left atrium. In some embodiments, the opening 912 is formed in an outer wall 913 of the left atrium. The outer wall 913 forms a portion of the outer surface 915 of the heart. The opening 912 is preferably spaced from the LAA 502 so that the delivery sheath 504 can be easily positioned near the LAA 502. For example, the opening 912 can be spaced from the orifice of the LAA 502 by a distance of about 1 to 10 cm, more preferably about 5 cm. However, the opening 912 can be formed at any point along the outer wall 913. For example, the opening 912 can be formed in the wall of the LAA 502. The opening 912 is configured and sized to receive the delivery sheath 504. In some exemplifying non-limiting embodiments, the cross sectional area of the delivery sheath 504 is equal to or more than about 30% of the area of the opening 912. The cross-sectional area of the delivery sheath 504 can be equal to or more than 40%, 50%, 60%, 70%, 80%, 90%, and ranges encompassing such percentages of the area of the opening 912. Thus, the delivery sheath 504 can be conveniently inserted through the opening 912 and maneuvered within the left atrium.

The illustrated delivery path can be positioned by passing the distal end 702 of the delivery sheath 504, which is located outside of the heart, through the wall 913 of the left atrium and into the chamber of the left atrium. It will be appreciated that the sheath 504 may be steered or turned to the desired location. The delivery sheath preferably has a length suitable for accessing the opening 912 and the LAA 502 from outside the heart and outside the patient, more preferably about 80 cm or less, and even more preferably about 70 cm or less, about 50 cm or less, about 30 cm or less, about 10 cm or less, or even ranges encompassing these lengths. As discussed above, the surgeon can easily position the delivery sheath 504. The delivery sheath 504 is distally advanced to a position for deployment, such that the distal end 702 of the delivery sheath 504 is proximate to the orifice of the LAA 502. The implant 304 can be delivered through the delivery sheath 504 and along the delivery path 910 as indicated by the arrows. Thus, the delivery sheath 504 defines the delivery path that passes directly through the wall of the left atrium and is used to deliver the implant 304 to the LAA 502.

Figure 42:
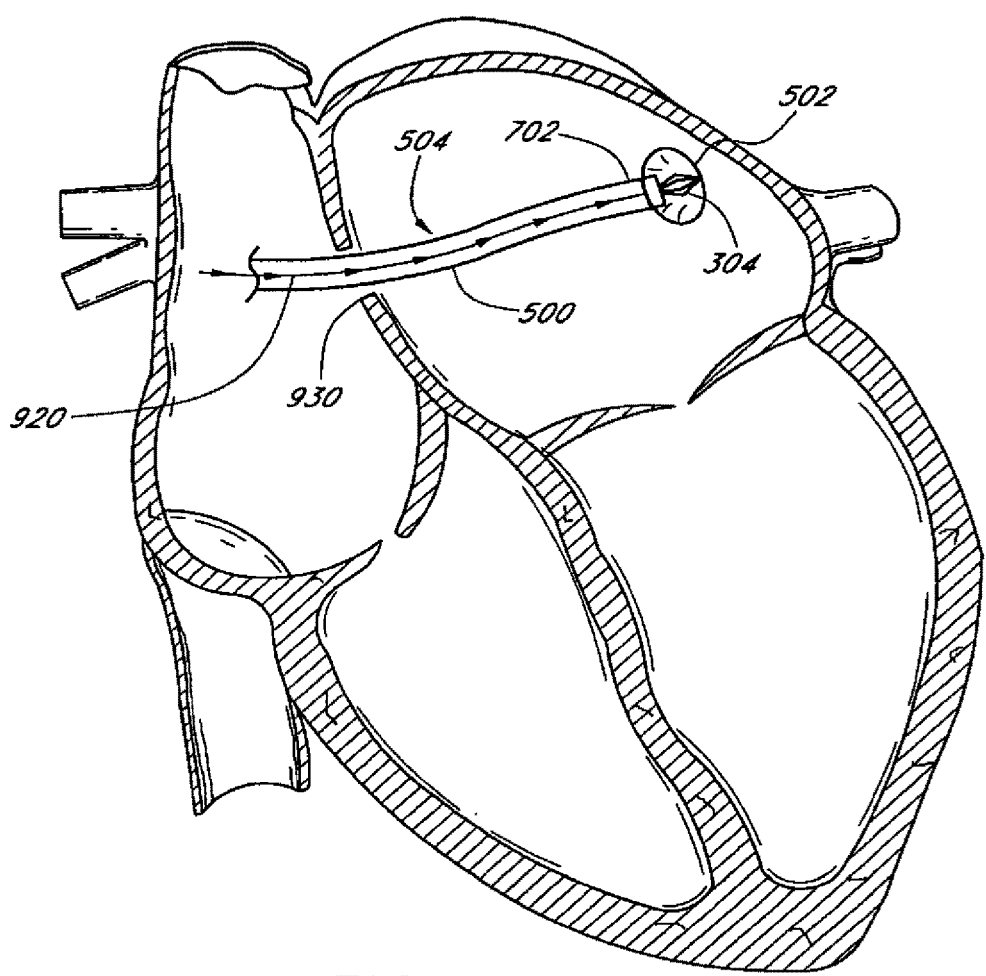
FIG. 42 is a view of the heart and a delivery sheath located within the right atrium and passing through a transseptal puncture.

In the illustrated embodiment of FIG. 42, the implant 304 can be delivered along a delivery path 920 that passes through the right atrium, a transseptal puncture 930, and the left atrium. The delivery path can be positioned by passing the distal end 702 of the delivery sheath 504 through the right atrium and towards the transseptal puncture 930. The transseptal puncture is sized and located to allow the distal end 702 of the delivery sheath 504 to pass through the transseptal puncture 930 and into the left atrium. The distal end 702 of the delivery sheath 504 is moved proximate to the orifice of the LAA 502 for the delivery and deployment of implant 304 by distally advancing the delivery sheath 504 through the right atrium and the transseptal puncture 930. The implant 304 can be delivered through the delivery sheath 504 and along the delivery path 920 as indicated by the arrows. Thus, the delivery sheath 504 defines a delivery path that passes through the right atrium, the transseptal puncture 930, and the left atrium. Access can be gained to the right atrium, for example, through the superior vena cava (as discussed above) or through the inferior vena cava. Access to the right atrium through the inferior vena cava can be obtained by advancing the delivery sheath 504 over the guidewire disposed within the inferior vena cava and the right atrium. Thus, the delivery sheath 504 can define a delivery path 920 that passes through the superior or inferior vena cava, the right atrium, and the transseptal puncture 930 and into the left atrium. Alternatively, the delivery path can comprise a pre-existing septal defect such as a hole (an atrial septal defect) or a tunnel (a patent foramen ovale).

As discussed above, the delivery sheath 504 can have various configurations that facilitate the delivery and deployment of the implant 304. For example, the delivery sheath 504 used for defining the delivery path through the pulmonary vein and the left atrium may have different shape and size than the delivery sheath 504 used for defining a delivery path directly through the wall of the left atrium. In particular, the length of the delivery sheath 504, which is used by passing the delivery sheath 504 through the pulmonary vein, may be different than the length of the delivery sheath 504, which is used by passing the delivery sheath 504 through the wall of the left atrium. Thus, the configuration of the delivery sheath 504 can ensure that the implant 304 can be delivered to the proper location in the heart even though a plurality of left atrium access paths can be used to deliver the implant 304 to the LAA 502. The delivery sheath 504 can have various cross sectional profiles, curves, shapes and sizes to ensure that the implant 304 can be properly delivered and deployed. For example, a distal portion of the delivery sheath 504 can be configured to deliver the implant 304 within the LAA 502. Preferably, the distal portion of the delivery sheath 504 can be configured (e.g., having pre-shaped or permanent curves) in order to locate the distal end 702 of the delivery sheath 504 within the LAA 502. The curvature of the distal end 702 of delivery sheath 504 can be similar to the curvature of the LAA 502 such that the distal end 702 can be distally advanced within the LAA 502. Further, the distal portion of the delivery sheath 504 can be an atraumatic soft-tip to prevent injury to the patient.

Figure 39:
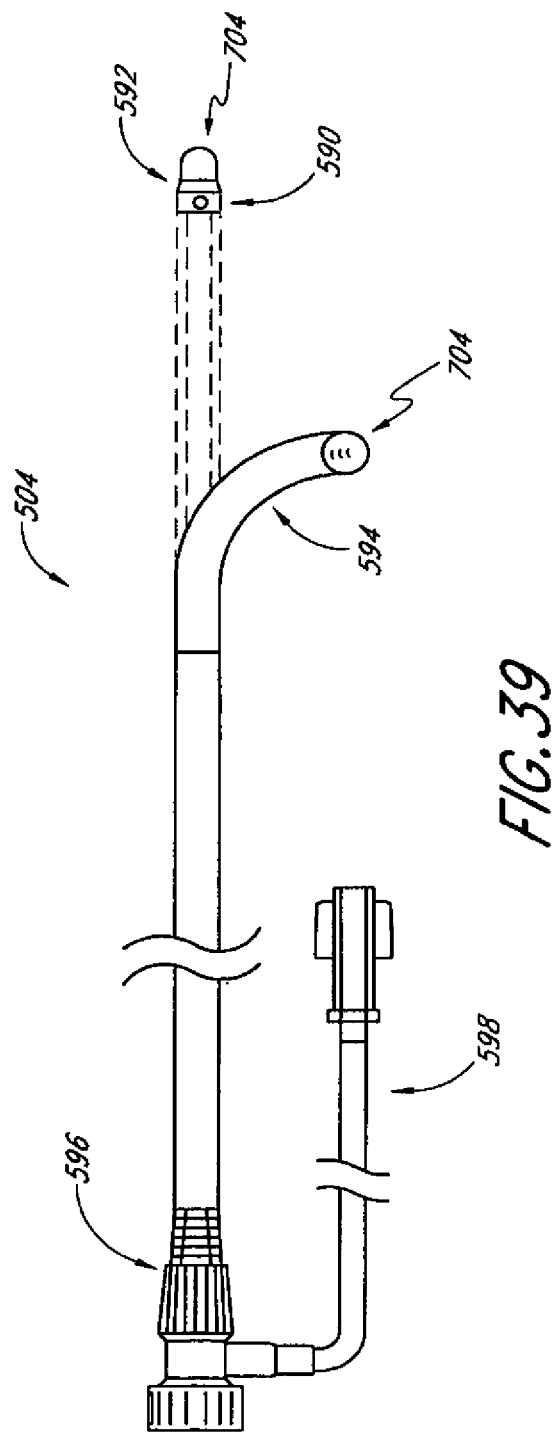
FIG. 39 is a schematic view of a delivery sheath and a transition catheter used in combination with the system of FIG. 32.

As shown in FIG. 39, a transition catheter or member 704 can be used with the delivery sheath 504 for easy handling and preventing injuries. The transition catheter 704 can be disposed within the delivery sheath 504 so that distal end 702 of the delivery sheath 504 is proximate to the distal end of the transition catheter 704. While the transition catheter 704 is disposed within the delivery sheath 504, the delivery sheath 504 can be put into the patient to define the delivery path for the implant 304. In one embodiment, the distal end of the transition catheter 704 can be a smooth, round top. The smooth, round top can prevent damage to the distal end 702 of the delivery sheath 504, for example, by providing structural support to the distal end 702 of the delivery sheath 504. Additionally, the smooth, round top can prevent injury to the patient by providing an atraumatic surface that contacts the patient thereby preventing contact between the distal end 702. After the delivery sheath 504 is properly located, the transition catheter 704 can be removed from the delivery sheath 504. Then the implant 304 can be inserted into the sheath 504 and delivered, as described above.

In one embodiment, the delivery sheath 504 can be advanced over a guidewire, not shown, for accessing the LAA 502 of a patient. For example, the guidewire can be disposed directly through the wall of the left atrium, e.g., along a left atrium access path through the wall of the left atrium. The delivery sheath 504 can be advanced over the guidewire and directly through the wall of the left atrium and towards the LAA 502. Additionally, the positioning of the delivery sheath 504 can be aided by various techniques, such as direct visualization from the exterior surface of the heart, visualization through the use of echocardiography (e.g., Intracardiac Echo or Transsesophogeal Echo), visualization through optics including through thoracoscopes, or through the use of X-Ray fluoroscopy. These techniques can aid the surgeon to properly advance and locate the delivery sheath 504.

After the delivery sheath 504 is in the desired position, the implant 304 can be deployed as described above. Generally, once the delivery sheath 504 is in deployment position, the delivery catheter 360 can be inserted into the delivery sheath 504. The delivery catheter has an appropriate length corresponding to the length of the delivery sheath, as selected for a desired access technique. For example, in a procedure through the wall of the left atrium or in an open procedure, as described herein, the delivery catheter, like the delivery sheath, may have a length of about 110 cm or less, and even more preferably about 80 cm or less, about 50 cm or less, about 30 cm or less, or even about 20 cm or less. In some embodiments, the delivery catheter has a length that is slightly greater than the delivery sheath. For example, the delivery catheter can have a length that is about 10 cm to about 30 cm greater than the length of the delivery sheath. For example, the delivery catheter can have a length that is about 10 cm greater than the length of the delivery sheath, about 15 cm greater than the length of the delivery sheath, about 20 cm greater than the length of the delivery sheath, about 25 cm greater than the length of the delivery sheath, about 30 cm greater than the length of the delivery sheath, and ranges encompassing these lengths. The implant 304 is collapsed and then the loading collar 510 and the peel-away sheath 512 are advanced distally over the flares 528 and the implant 304 until the distal tip of the implant 304 is aligned with the distal end of the peel-away sheath 512 and the distal end of the loading collar 510. The loading collar 510 can then be removed resulting in the collapsed implant 304 located partially within the recapture sheath 514 and retracted within the peel-away sheath 512, and the entire system is flushed.

The implant 304 is inserted in the delivery sheath 504 and is advanced through the delivery sheath 504 by distal movement of the delivery catheter 360. The implant 304 is aligned and positioned for deployment. Preferably, the implant 304 can maintain proper position by holding the deployment handle 538 in a particular position. The delivery sheath 504 can move proximally until the implant 304 is exposed. The surgeon can adjust the position of the implant 304 by collapsing the implant 304 and repositioning the implant 304, and the repositioned implant 304 can be re-expanded. The implant 304 can be released from the delivery system 500 after the implant 304 is properly positioned because recapture may not be necessary. The delivery system 500 preferably is retracted and removed through the delivery sheath 504. There are various techniques (e.g., contrast injections, fluoroscopy, thoracoscopy, and/or echocardiography) to confirm proper positioning and delivery of the implant 304 and containment of thrombus within the LAA 502. The delivery sheath 504 preferably is withdrawn along the left atrium access path.

Thus, the delivery system 500 can be configured and sized to locate and deploy the implant 304 in the LAA 502 as an adjunct to many surgical procedures which may or may not be related to the LAA 502. Depending on the surgical procedure, one of the various embodiments of the delivery system 500 may be more conveniently used than other embodiments of the delivery system 500 to deploy the implant 304.

Figure 41A:
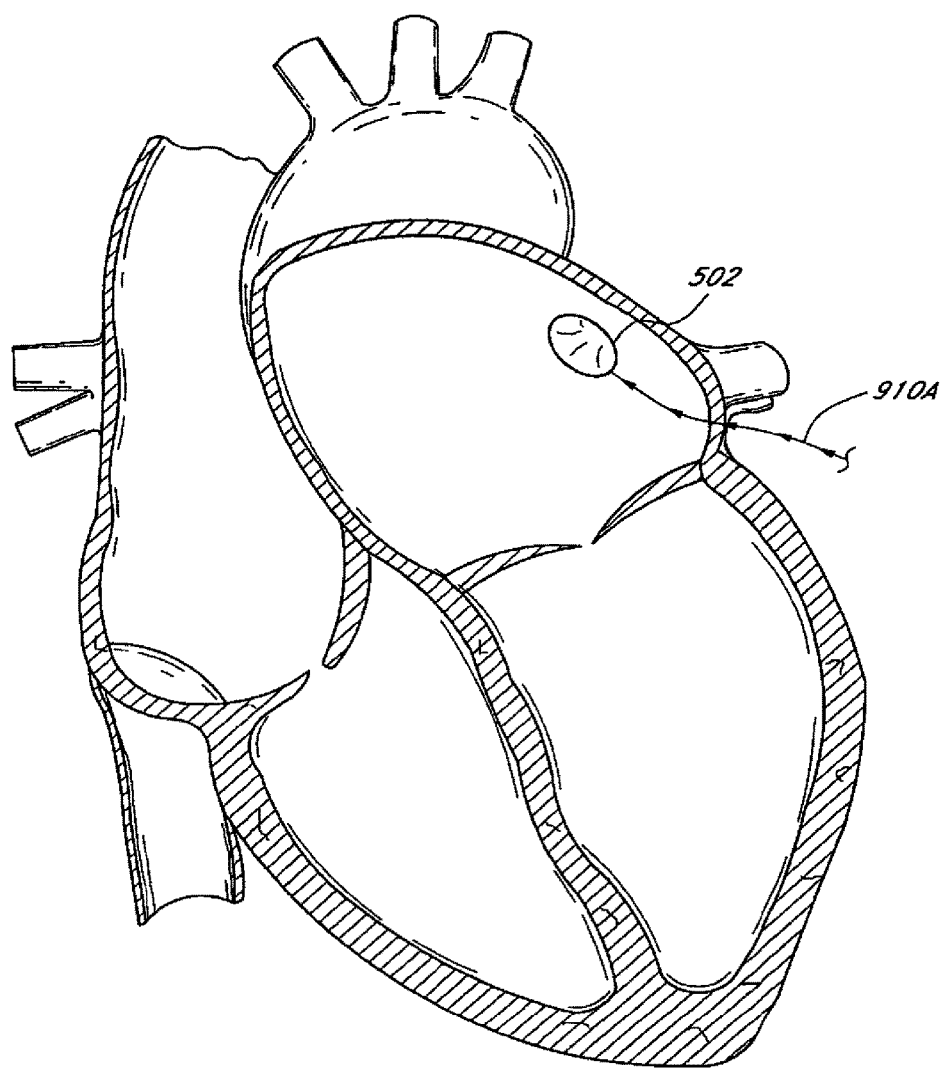
FIG. 41A is a view of an open heart and a delivery path.

In the illustrated embodiment of FIG. 41A, the implant 304 can be delivered along a delivery path 910A that passes through an open left atrium. A surgical procedure, such as open heart valve surgery, provides the open left atrium for convenient access to the LAA 502. The surgical procedure can form an opening in the chest of a patient suitable for open heart procedures. For example, the opening in the chest can be formed by a sternotomy incision. In one embodiment, the delivery path 910A can be positioned by passing the distal end 702 of the delivery sheath 504 through the opening in the left atrium obtained for open heart surgery. The delivery sheath 504 in this embodiment may have a length of about 80 cm or less, about 70 cm or less, about 50 cm or less, about 30 cm or less, or even about 10 cm or less. In one embodiment, the delivery sheath has a length of about 1 to 10 cm. As discussed above, the surgeon can easily manually position the delivery sheath 504. Thus, the delivery system 500 can be used to locate and deploy the implant 304 to occlude the LAA 502. During open heart surgery, the delivery system 500 can be used without the recapture sheath 514 because of the accessibility of the LAA 502 and convenience of deploying the implant 304. Those skilled in the art recognize that various catheters (e.g., delivery sheath 504 and/or recapture sheath 514) can be used with the delivery system 500. If the delivery sheath 504 is used during open heart surgery, the delivery sheath 504 is preferably generally straight and has a length less than the length of the delivery sheath 504 used, e.g., for implant 304 delivery through the femoral vein. Similarly, the length of the delivery system 500 used for delivering the implant 304 along the delivery path 910A is preferably less than the length of the delivery system 500 used to deliver the implant 304 through the femoral vein.

Figure 43:
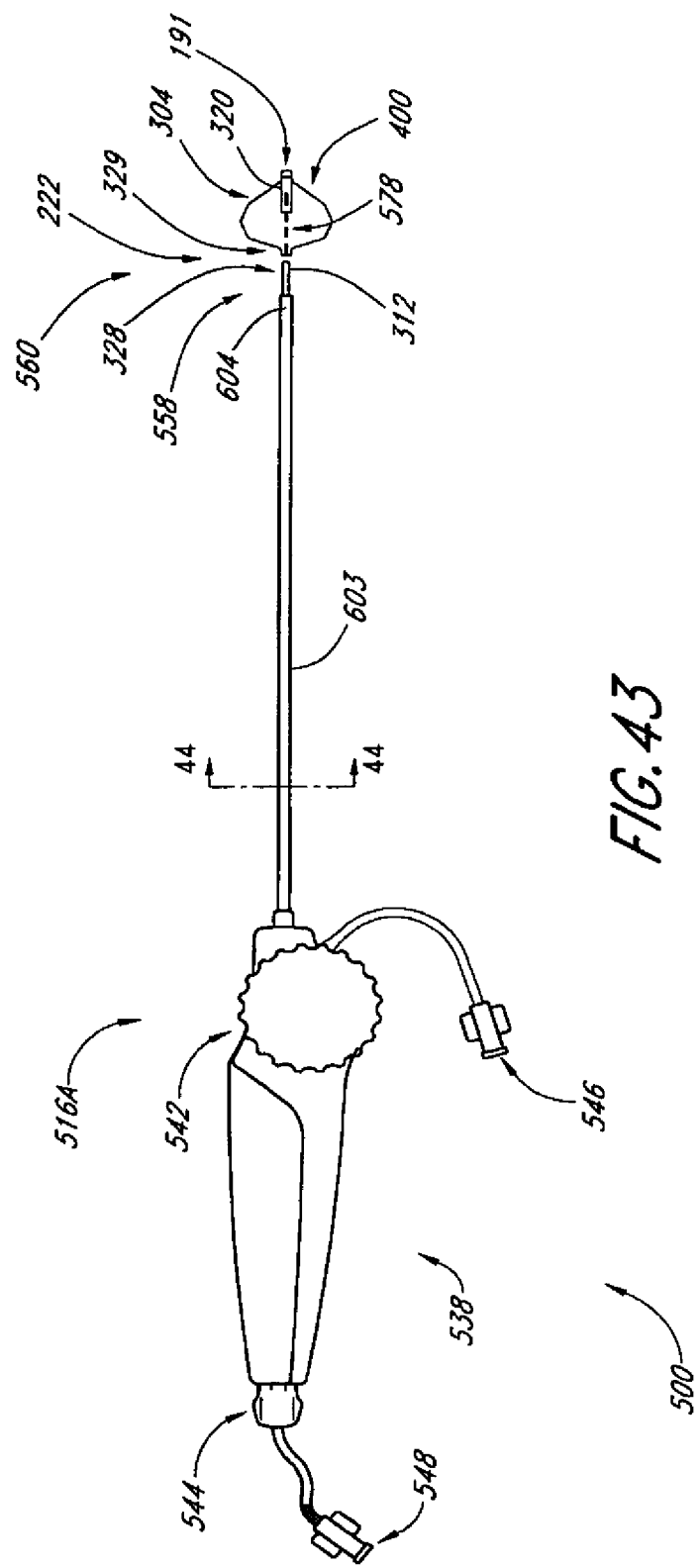
FIG. 43 a schematic view of a delivery system attached to an implantable containment device in accordance with another embodiment.
Figure 44:
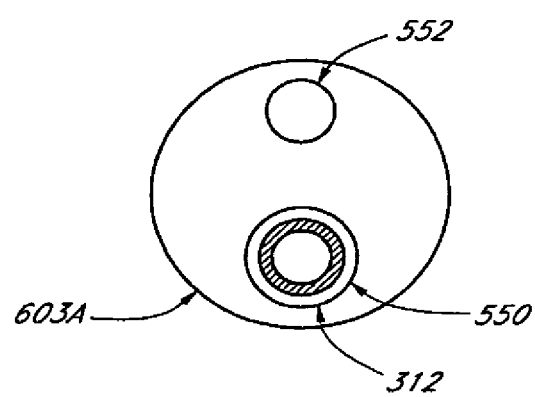
FIG. 44 is a cross sectional view of a deployment catheter as shown in FIG. 43, taken along cut line 44-44.

In one embodiment, a deployment catheter 516A (shown in FIG. 43) is used in conjunction with open heart surgery. In one embodiment, the deployment catheter 516A is used without a delivery sheath. The deployment catheter 516A has the deployment handle 538 connected to a shaft 603. The implant 304 is located near a distal end 605 of the shaft 603. The core 312 extends axially throughout the length of the shaft 603 and can be attached at its distal end to the implant 304. The pull wire or control line 328 extends proximally throughout the length of the shaft 603 to the deployment handle 538. The shaft 603 can be sized and configured so that the implant 304 can be easily located and deployed within the LAA 502. In one embodiment, for example, shaft 603 has a length in the range of about 5 cm to 15 cm, more preferably in the range of about 9 cm to 11 cm. It will be appreciated that the shaft 603 may have any suitable length for access the LAA in an open procedure, such as about 80 cm or less, about 70 cm or less, about 50 cm or less, or about 30 cm or less. The shaft 603 can be a multi-lumen shaft, similar to the shaft 540 shown in FIG. 32A. The shaft 603 preferably comprises the core lumen 550 for holding the axially moveable core 312, the control line lumen 552 and two proximal injection lumens 554 in communication with proximal injection port 546. The control line 328 preferably extends through the control line lumen 552 and preferably couples to the proximal hub 324 of the implant 304 to the deployment handle control knob 542, allowing for implant 304 expansion and collapse. Thus, during open heart surgery, for example, the implant 304 can be passed directly into the left atrium of the open heart and along the delivery path 910A and into the LAA 502. Implant 304 is collapsed, preferably before it is passed through the left atrium and into the LAA 502, by rotating the control knob 542 counter-clockwise until the implant 304 is fully collapsed. The counterclockwise motion of the control knob 542 retracts at least a portion of the control line 328 and places tension on the proximal hub 324 of the implant 304. While the distal portion of the axially moveable core 312 engages slider assembly 400 and applies a distal force to the distal hub 314 of the implant 304, tension in the control line 328 preferably causes the proximal hub 324 of the implant 304 to move proximally relative to the axially moveable core 312, thereby collapsing the implant 304. In one embodiment, the deployment catheter 516A comprises a multi-lumen shaft 603A (shown in FIGS. 44 and 45 without the control line 328) comprising the core lumen 550 for holding the axially moveable core 312 and the control line lumen 552. Although not illustrated, the deployment catheter 516A can be used with a delivery sheath 504 to aid in the delivery and deployment of the implant 304.

As shown in FIG. 45, an insertion tool 538A comprises the shaft 603A connected to a handle 610 having a lever or trigger 612. The trigger 612 can be moved towards the handle 610 thereby causing the implant 304 to collapse. In one embodiment, the control line 328 is coupled to the trigger 612 such that movement of the trigger 612 towards the handle 610 retracts at least a portion of the control line 328, thereby placing tension on the proximal hub 324 of the implant 304. The tension in the control line 328 causes the proximal hub 324 of the implant 304 to move proximally relative to the axially moveable core 312, thereby collapsing the implant 304. As tension on the pull wire 328 is reduced by moving the trigger 612 away from the handle 610, the implant 304 assumes its expanded diameter configuration by bending under its own bias. Advantageously, the insertion tool 538A can facilitate proper placement of the implant 304, and the grip 310 can be shaped to conveniently fit the hand of a user. In one embodiment, for example, shaft 603A has a length in the range of about 5 cm to 15 cm, more preferably in the range of about 9 cm to 11 cm, so that the implant 304 can be easily located and deployed in the LAA 502. Those skilled in the art recognize that the various catheters (e.g., delivery sheath 504 and/or recapture sheath 514) can be used with the delivery system 500 shown in FIG. 45.

The implant 304 can also be manually deployed in the LAA 502, preferably during open heart surgery. Thus, the implant 304 can be positioned and deployed within the LAA 502 without the use of a delivery system. For example, the surgeon can manually hold the implant 304 and pass the implant 304 into the opened heart, through the left atrium, and into the LAA 502. The surgeon can manually apply an inward radial force to the frame 14 to collapse the implant 304 for convenient positioning at the desired site. After the implant 304 is placed within the LAA 502, the implant 304 can assume its expanded configuration by bending under its own bias. Of course, to move the implant 304 into the LAA 502, the surgeon can provide a distal force on the proximal hub 324 of the implant 304 in the direction of the LAA 502. For example, because of the open access to the left atrium during open heart surgery, the surgeon's thumb can be conveniently used to push on the proximal hub 324 of the implant 304 to move the implant 304 into the LAA 502, even though the implant 304 engages with the wall of the LAA 502 because of the implant 304 biasing to the expanded configuration. The surgeon can manually apply an inward radial force to the implant 304 to collapse the implant 304 for convenient repositioning or removal of the implant 304.

As illustrated in the partial cross-sectional view of FIG. 46 and FIG. 47, in another embodiment of a delivery system a delivery sheath 1002 surrounds the implant 304 and a portion of a push rod 1010. The sheath 1002 has a sheath wall 1003 defining an inner surface 1008 that engages with the implant 304 to keep the implant 304 in the collapsed position. The push rod 1010 has a distal end 1012 that can contact the proximal hub 324 of implant 304. When the push rod 1010 is moved in the distal direction the distal end 1012 contacts and causes the implant 304 to move in the distal direction. Those skilled in the art recognize that the distal end 1012 may or may not be coupled to the proximal hub 324. When the implant 304 moves out of the sheath 1002, the implant 304 can expand and assume its expanded diameter configuration by bending under its own bias. Preferably, the implant 304 is passed through the sheath 1002 and deployed in the LAA 502 as an adjunct to open heart surgery. For example, during open heart surgery, the surgeon can hold and move the proximal end 1013 of the push rod 1010 in the distal direction. The push rod 1010 and implant 304 move together in the distal direction towards a distal end 1004 of the sheath 1002. As the implant 304 moves out of an opening 1005 of the sheath 1002, the implant 304 can expand under its own bias. Preferably, the distal end 1004 of the sheath 1002 is located proximate to the opening of the LAA 502 so that the implant 304 expands within the LAA 502 upon exiting the sheath 1002. After the implant 304 is expanded in the LAA 502, the sheath 1002 and the push rod 1010 can be removed from the open heart. Of course, the surgeon can adjust the position of the implant 304 within the LAA 502. For example, as discussed above, the surgeon can manually provide a distal or proximal force on the proximal hub 324 to move the implant 304 relative to the LAA 502.

To inhibit migration of the implant 304 out of the LAA 502, the implant 304 can have barbs or anchors 195 that face proximally as described above. The anchors 195 can engage with adjacent tissue to retain the implant 304 in its implanted position and can limit relative movement between the tissue and the implant 304. Further, after the implant 304 is deployed, various techniques can be performed to ensure that the implant 304 is properly located in the LAA 502. For example, the left atrium or LAA may change shape or expand after the implant 304 is deployed. The orifice of the LAA 502 can be sutured while the implant 304 is within the LAA 502 to further fix the implant 304 into the LAA 502.

It will be appreciated that the delivery systems for the implant 304 described above can be used in combination with conventional instruments used in open surgical procedures or other procedures performed through the chest of a patient and any procedures that are being performed as an adjunct with the delivery of the implant 304 to the LAA. For example, when the implant is to be delivered through the chest, one embodiment of the invention includes a delivery sheath or catheter as described above, an implant sized and configured to prevent passage of embolic material from the left atrial appendage, and means or instruments for providing surgical access through the chest of the patient or for performing surgical procedures on the heart, e.g., retractors, rib spreaders, forceps, scissors, shears, rongeurs, clip appliers, staplers, sutures, needle holders, bulldogs, clamps, elevators, cauterizing instruments or substances, electrosurgical pens, suction apparatus, approximators, and/or the like. When the implant is to be delivered through an outer wall of the left atrium, another embodiment of the invention includes a delivery sheath or catheter as described above, an implant sized and configured to prevent passage of embolic material from the left atrial appendage, and means or instruments for providing access through the left atrium wall, e.g., trocars, port instruments, and the like. When the implant is to be delivered as an adjunct to another surgical procedure, another embodiment of the invention includes a delivery sheath or catheter as described above, an implant sized and configured to prevent passage of embolic material from the left atrial appendage, and means for performing surgical heart procedures, e.g., conventional surgical instruments (such as those described herein) for accessing the heart and performing surgical procedures on the heart. Thus, conventional surgical instruments can be used in conjunction with the delivery of the implant, e.g., when the implant is delivered through the atrial wall of the heart, through the wall of LAA, etc.

Optionally, various procedures and instruments can be used in conjunction with the delivery of the implant, especially if the implant is delivered as an adjunct to an open surgical procedure or other surgical heart procedure. For example, one or more verres needles, trocars, cannulas, insufflators, laparoscopes, light sources, video monitors, forceps, scissors, clip appliers, sutures, needle holders, clamps, retractors, elevators, morcellators, cauterizing instruments or substances, electrosurgical cutting or grasping instruments, suction apparatuses, approximators, and/or the like can be used before, during, and/or after the surgical procedures and/or delivery of the implant in the LAA.

Throughout this application the terms implant and occlusion device have been used. One of ordinary skill in the art will appreciate that all of the disclosures herein are applicable to a wide variety of structures that include both implants that may or may not also be occlusion devices. Routine experimentation will demonstrate those limited circumstances under which certain disclosures and combinations thereof are not beneficial.

Further details regarding left atrial appendages devices and related methods are disclosed in U.S. Pat. No. 6,152,144, titled "Method and Device for Left Atrial Appendage Occlusion," filed Nov. 6, 1998, U.S. patent application Ser. No. 09/435,562, filed Nov. 8, 1999, U.S. patent application Ser. No. 10/033,371, titled "Adjustable Left Atrial Appendage Occlusion Device," filed Oct. 19, 2001. The entirety of each of these is hereby incorporated by reference in their entirety.

While particular forms of the invention have been described, it will be apparent that various modifications can be made without departing from the spirit and scope of the invention. Accordingly, it is not intended that the invention be limited, except as by the appended claims.

What is claimed is:

1. A system for deploying a medical implant, comprising:
a delivery catheter having a lumen extending therethrough;
an elongate shaft slidably disposed within the lumen of the delivery catheter; and
an expandable implant including a proximal tubular portion and a distal tubular portion discontinuous with the proximal tubular portion;
wherein the distal tubular portion extends at least partially within an interior of the implant,
wherein the distal tubular portion includes a slot forming an opening extending from an interior surface of the distal tubular portion through a wall thereof to an exterior surface of the distal tubular portion.

2. The system of claim 1, wherein the implant is actuatable from a collapsed delivery configuration to an expanded operational configuration.

3. The system of claim 2, wherein a distal end of the elongate shaft extends through the proximal tubular portion and into the distal tubular portion in the collapsed delivery configuration.

4. The system of claim 3, further including a coupling mechanism configured to releasably couple the implant to the elongate shaft.

5. The system of claim 4, wherein the implant is non-rotatably coupled to the elongate shaft.

6. The system of claim 3, further including a pull wire disposed within the lumen of the delivery sheath alongside the elongate shaft, the pull wire releasably connected to the proximal tubular portion by a releasable lock including a pin oriented laterally through the proximal tubular portion.

7. The system of claim 6, wherein the pull wire includes first and second ends disposed adjacent a proximal end of the delivery sheath, and a portion of the pull wire extends over the pin to form a loop portion, the elongate shaft extending through the loop portion.

8. The system of claim 7, wherein proximal tension on the pull wire with the elongate shaft disposed within the distal tubular portion maintains the implant in the collapsed delivery configuration.

9. The system of claim 8, wherein axial withdrawal of the distal end of the elongate shaft through the loop portion releases the pull wire from the proximal tubular portion.

10. The system of claim 3, wherein the implant is self-biased toward the expanded operational configuration.

11. The system of claim 10, wherein the elongate shaft has a column strength that exceeds an axial force exerted on the distal end of the elongate shaft by a distal end of the implant in the collapsed delivery configuration.

12. The system of claim 1, wherein the elongate shaft includes a lumen extending longitudinally therethrough; and
   wherein the coupling mechanism includes a side port disposed in a wall of the elongate shaft, a bending plug disposed within the elongate shaft adjacent the side port, and a locking member slidably disposed within the lumen of the elongate shaft.

13. The system of claim 12, wherein the locking member extends axially within the lumen of the elongate shaft, through the side port, and through the slot, thereby coupling the implant to the elongate sheath.

14. The system of claim 13, wherein axial retraction of the locking member through the slot and the side port releases the implant from the elongate shaft without relative rotation between the implant and the elongate shaft.

15. The system of claim 1, further including a handle disposed on a proximal end of the delivery catheter.

16. The system of claim 15, wherein a proximal end of the elongate shaft is attached to a control element on the handle.

* * * * *